(12) United States Patent
Lencer et al.

(10) Patent No.: US 10,806,793 B2
(45) Date of Patent: Oct. 20, 2020

(54) MUCOSAL DELIVERY OF THERAPEUTIC MOLECULES, PROTEINS, OR PARTICLES COUPLED TO CERAMIDE LIPIDS

(71) Applicant: Children's Medical Center Corporation, Boston, MA (US)

(72) Inventors: Wayne I. Lencer, Jamaica Plain, MA (US); Daniel J F Chinnapen, Quincy, MA (US); Randy Mrsny, Los Altos Hills, CA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 15/817,661

(22) Filed: Nov. 20, 2017

(65) Prior Publication Data

US 2018/0133332 A1   May 17, 2018
US 2018/0333499 A9   Nov. 22, 2018

Related U.S. Application Data

(60) Continuation of application No. 15/255,595, filed on Sep. 2, 2016, which is a division of application No. 13/062,638, filed as application No. PCT/US2009/004986 on Sep. 4, 2009, now Pat. No. 9,457,097.

(60) Provisional application No. 61/191,468, filed on Sep. 8, 2008.

(51) Int. Cl.
| | |
|---|---|
| *A61K 47/54* | (2017.01) |
| *A61K 47/61* | (2017.01) |
| *A61K 31/4164* | (2006.01) |
| *A61K 38/26* | (2006.01) |
| *A61K 39/15* | (2006.01) |
| *C12N 7/00* | (2006.01) |

(52) U.S. Cl.
CPC ........ *A61K 47/549* (2017.08); *A61K 31/4164* (2013.01); *A61K 38/26* (2013.01); *A61K 39/15* (2013.01); *A61K 47/543* (2017.08); *A61K 47/544* (2017.08); *A61K 47/61* (2017.08); *C12N 7/00* (2013.01); *C12N 2720/12322* (2013.01); *C12N 2720/12334* (2013.01)

(58) Field of Classification Search
CPC ..... A61K 47/549; A61K 47/544; A61K 47/61
USPC ......................................................... 514/23
See application file for complete search history.

(56) References Cited

U.S. PATENT DOCUMENTS

| | | | |
|---|---|---|---|
| 4,610,868 A | 9/1986 | Fountain et al. | |
| 5,366,963 A * | 11/1994 | Ladisch | A61K 31/70 424/450 |
| 5,846,951 A * | 12/1998 | Gregoriadis | A61K 9/1271 514/54 |
| 5,965,519 A | 10/1999 | Yatvin et al. | |
| 6,193,997 B1 | 2/2001 | Modi | |
| 9,457,097 B2 | 10/2016 | Lencer et al. | |
| 2003/0114415 A1 | 6/2003 | Wurtman et al. | |
| 2005/0281772 A1 | 12/2005 | Bromley et al. | |
| 2006/0052316 A1 | 3/2006 | Porcelli | |
| 2007/0231344 A1 | 10/2007 | Leadbetter et al. | |
| 2008/0299168 A1* | 12/2008 | Dadey | A61K 9/0024 424/423 |
| 2012/0252727 A1 | 10/2012 | Lencer et al. | |
| 2012/0277158 A1 | 11/2012 | Castaigne et al. | |
| 2014/0171372 A1 | 6/2014 | Lalezari et al. | |
| 2016/0266097 A1 | 9/2016 | Gagnon | |
| 2017/0095563 A1 | 4/2017 | Lencer et al. | |

FOREIGN PATENT DOCUMENTS

| | | |
|---|---|---|
| EP | 1972349 A1 | 9/2008 |
| WO | WO 94/01138 A1 | 1/1994 |
| WO | WO 99/15201 A1 | 4/1999 |
| WO | WO 99/43356 A1 | 9/1999 |
| WO | WO 03/106474 A2 | 12/2003 |
| WO | WO 08/111916 A1 | 9/2008 |
| WO | WO 2016/118697 A9 | 7/2016 |

OTHER PUBLICATIONS

Gao et al. Potentiation of Cationic Liposome-Mediated Gene Delivery by Polycations. Biochemistry 1996, 35, 1027-1036. (Year: 1996).*
Backhed et al., Host-bacterial mutualism in the human intestine. Science. Mar. 25, 2005;307(5717):1915-20.
Bagai et al., Reconstituted Sendai virus envelopes as biological carriers: dual role of F protein in binding and fusion with liver cells. Biochim Biophys Acta. Oct. 10, 1993;1152(1):15-25.
Brown, Lipid rafts, detergent-resistant membranes, and raft targeting signals. Physiology (Bethesda). Dec. 2006;21:430-9.
Chigorno et al., Formation of a cytosolic ganglioside-protein complex following administration of photoreactive ganglioside GM1 to human fibroblasts in culture. FEBS Lett. Apr. 24, 1990;263(2):329-31.
Dickinson et al., Bidirectional FcRn-dependent IgG transport in a polarized human intestinal epithelial cell line. J Clin Invest. Oct. 1999;104(7):903-11.
Dickinson et al., Ca2+-dependent calmodulin binding to FcRn affects immunoglobulin G transport in the transcytotic pathway. Mol Biol Cell. Jan. 2008;19(1):414-23. Epub Nov. 14, 2007.
Doyle et al., Glucagon-like peptide-1. Recent Prog Horm Res. 2001;56:377-99.
Franchini et al., Synthesis of a fluorescent sulfatide for the study of CD1 antigen binding properties. Eur J Org Chem. Dec. 2004;2004(23):4755-61.
Kieffer et al., The glucagon-like peptides. Endocr Rev. Dec. 1999;20(6):876-913.

(Continued)

*Primary Examiner* — Yih-Horng Shiao
(74) *Attorney, Agent, or Firm* — Wolf, Greenfield & Sacks, P.C.

(57) ABSTRACT

Described herein are compositions and methods useful for allowing for the absorption (passage) of agents of interest, such as therapeutic agents, across epithelial and mucosal barriers and/or into certain subcellular compartments of the cell, such as the recycling endosome (RE), Golgi, and the endoplasmic reticulum (ER).

19 Claims, 46 Drawing Sheets

(56) References Cited

OTHER PUBLICATIONS

Ledeen et al., The multi-tasked life of GM1 ganglioside, a true factotum of nature. Trends Biochem Sci. Jul. 2015;40(7):407-18. doi: 10.1016/j.tibs.2015.04.005. Epub May 26, 2015.

Lencer et al., The intracellular voyage of cholera toxin: going retro. Trends Biochem Sci. Dec. 2003;28(12):639-45.

Lencer et al., Transcytosis of cholera toxin subunits across model human intestinal epithelia. Proc Natl Acad Sci U S A. Oct. 24, 1995;92(22):10094-8.

Maxfield et al., Endocytic recycling. Nat Rev Mol Cell Biol. Feb. 2004;5(2):121-32.

Mukherjee et al., Endocytic sorting of lipid analogues differing solely in the chemistry of their hydrophobic tails. J Cell Biol. Mar. 22, 1999;144(6):1271-84.

Mukherjee et al., Role of membrane organization and membrane domains in endocytic lipid trafficking. Traffic. Mar. 2000;1(3):203-11.

Orskov et al., Biological effects and metabolic rates of glucagonlike peptide-1 7-36 amide and glucagonlike peptide-1 7-37 in healthy subjects are indistinguishable. Diabetes. May 1993;42(5):658-61.

Panasiewicz et al., Preparation of Alexa Fluor 350-conjugated nonradioactive or 3H-labeled GM1 ganglioside derivatives with different ceramides. Anal Biochem. Feb. 1, 2009;385(1):168-70. Epub Oct. 21, 2008.

Rakoff-Nahoum et al., Innate immune recognition of the indigenous microbial flora. Mucosal Immunol. Nov. 2008;1 Suppl 1:S10-4. doi: 10.1038/mi.2008.49.

Rockendorf et al., Synthesis of a fluorescent ganglioside GM1 derivative and screening of a synthetic peptide library fir GM1 binding sequence motifs. Bioconjugate Chemistry. 2003; 18:573-578.

Shang et al., Toll-like receptor signaling in small intestinal epithelium promotes B-cell recruitment and IgA production in lamina propria. Gastroenterology. Aug. 2008;135(2):529-38. doi: 10.1053/j.gastro.2008.04.020. Epub Apr. 22, 2008.

Simons et al., Model systems, lipid rafts, and cell membranes. Annu Rev Biophys Biomol Struct. 2004;33:269-95.

Simons et al., Cholesterol, lipid rafts, and disease. J Clin Invest. Sep. 2002;110(5):597-603.

Sonnino et al., Preparation of GM1 ganglioside molecular species having homogeneous fatty acid and long chain base moieties. J Lipid Res. Feb. 1985;26(2):248-57.

Spiekermann et al., Receptor-mediated immunoglobulin G transport across mucosal barriers in adult life: functional expression of FcRn in the mammalian lung. J Exp Med. Aug. 5, 2002;196(3):303-10.

Stover et al., Liposomal delivery enhances short-chain ceramide-induced apoptosis of breast cancer cells. J Pharmacol Exp Ther. Nov. 2003;307(2):468-75. Epub Sep. 15, 2003.

Sturm et al., Structure-function studies on positions 17, 18, and 21 replacement analogues of glucagon: the importance of charged residues and salt bridges in glucagon biological activity. J Med Chem. Jul. 16, 1998;41(15):2693-700.

Tsai et al., Protein disulfide isomerase acts as a redox-dependent chaperone to unfold cholera toxin. Cell. Mar. 23, 2001;104(6):937-48.

Van Genderen et al., Differential targeting of glucosylceramide and galactosylceramide analogues after synthesis but not during transcytosis in Madin-Darby canine kidney cells. J Cell Biol. Nov. 1995;131(3):645-54.

Vavrova et al., Synthetic ceramide analogues as skin permeation enhancers: structure-activity relationships. Bioorganic & Medicinal Chemistry. 2003;11:5381-5390.

Xiao et al., Biological activities of glucagon-like peptide-1 analogues in vitro and in vivo. Biochemistry. Mar. 6, 2001;40(9):2860-9.

U.S. Appl. No. 15/255,595, filed Sep. 2, 2016, Lencer et al.

PCT/US18/57787, Jan. 25, 2019, International Search Report and Written Opinion.

Pohl et al., Rapid transmembrane diffusion of ceramide and dihydroceramide spin-labelled analogues in the liquid ordered phase. Mol Membr Biol. Apr. 2009;26(3):194-204.

* cited by examiner

C12:0-Alexa-GM1

C16:1-Alexa-GM1

C16:0-Alexa-GM1

C20:0-Alexa-GM1

C12-GM1

C18-GM1

```
  1 mksiyfvagl fvmlvqgswq rslqdteeks rsfsasqadp lsdpdqmned krhsqgtfts 61 dyskyldsrr agdfvqwlmn tkrnrnniak rhdeferhae gtftsdvssy leggaakefi
                                              ^

121 awlvkgr grrdfpeevaive elgrrhadgs fsdemntild niaardfinw liqtkitdrk
    ^ ^
```

When applied together, the two ceramides are sorted differentially

MUCOSAL DELIVERY OF THERAPEUTIC MOLECULES, PROTEINS, OR PARTICLES COUPLED TO CERAMIDE LIPIDS

CROSS REFERENCE TO RELATED APPLICATIONS

This application is a continuation of U.S. application Ser. No. 15/255,595, filed Sep. 2, 2016, which is a divisional of U.S. application Ser. No. 13/062,638, filed Nov. 8, 2011, now U.S. Pat. No. 9,457,097, which is a national stage filing under 35 U.S.C. § 371 of international application PCT/US2009/004986 designating the United States of America, filed Sep. 4, 2009, which claims the benefit under 35 USC § 119(e) of U.S. Provisional Application No. 61/191,468, filed Sep. 8, 2008, the disclosures of each of which are incorporated by reference herein in their entirety.

FUNDING

This invention was made with government support under grant DK48106 awarded by the National Institutes of Health. The government has certain rights in the invention.

BACKGROUND OF INVENTION

Drug permeability and half-life are some of the limiting factors in the development of new therapeutics. It would be beneficial to have improved approaches to enhancing drug availability, introducing drugs into cells and lengthening their half-lives.

SUMMARY OF INVENTION

Described herein are compositions and methods useful for allowing for the absorption (passage) of agents of interest, such as therapeutic agents, across epithelial and mucosal barriers and/or into certain subcellular compartments of the cell, such as the recycling endosome (RE), Golgi, and the endoplasmic reticulum (ER). In the subject compositions and methods, an agent, such as a therapeutic agent, is coupled with or attached to a ceramide of the correct structure, as described herein. As also described herein, the fatty acid structure of ceramides has been shown to direct their trafficking and the subject compositions and methods can be used to harness intracellular trafficking in order to prolong the half-life of agents of interest (e.g., therapeutic agents) and/or to deliver agents of interest across epithelial mucosal barriers. The technology will be useful for administering them parenterally (e.g., by administering subcutaneously, intramuscularly, by inhalation or by intravenous injection, topically to mucosal or other epithelial surfaces) or enterally/nonparenterally.

In one embodiment, the invention relates to a delivery vehicle comprising a glycosphingolipid and an agent to be delivered, wherein the glycosphingolipid comprises a ceramide that comprises (a) a short chain fatty acid (C4-C12) or (b) a long chain fatty acid (C14-C28) comprising at least one cis double bond between two carbon atoms (between two adjacent carbon atoms) and the agent to be delivered is attached to the oligosaccharide of the glycosphingolipid. In specific embodiments, the short chain fatty acid (C4-C12) includes no double bonds between its carbon atoms. In alternative embodiments, the short chain fatty acid (C4-C12) comprises a (one, one or more, at least one) cis double bond between its carbon atoms.

In specific embodiments, the fatty acid of the delivery vehicle is (a) a C12 fatty acid (which can be C12 with no double bonds or C12 comprising a (one, one or more, at least one) cis double bond), such as C12 with one double bond (designated C12:1)) or (b) a C16 fatty acid comprising a (one, one or more, at least one) cis double bond, such as C16 with one double bond (designated C16:1). The glycosphingolipid of the vehicle may be selected from the group consisting of neutral glycosphingolipids, such as globosides or acidic glycosphingolipids, such as gangliosides. The ganglioside of the vehicle comprises a (one, one or more, at least one) sialic acid and, in a specific embodiment, includes only one sialic acid. In a specific embodiment, the ganglioside of the vehicle is monosialotetrahexosylganglioside (GM1).

The agent of interest of the delivery vehicle is, for example, a protein, peptide, nucleic acid, carbohydrate (e.g., polysaccharide), lipid, glycoprotein, and any combinations thereof. Synthetic organic and inorganic drugs that can exert a biological effect when administered to a subject are also included. The agent of interest may be a therapeutic agent, such as an anti-inflammatory agent, a vaccine antigen, an anti-cancer drug or chemotherapeutic drug, a clotting factor, a hormone, a cytokine, a chemokine, a matrix matallopro-tease, or a small bioactive molecule such as adenosine, a steroid, a cytokine, an antibiotic, or a drug for the treatment of cardiovascular disease, an infectious disease, an autoimmune disease, allergy, a blood disorder, a metabolic disorder or a skin disease. In addition, glycosphingolipids attached to antigen can be administered as a vaccine and/or to stimulate an individual's response to a vaccine. An antigen is selected from the group consisting of: an antigen that is characteristic of a pathogen, an antigen that is characteristic of an autoimmune disease, an antigen that is characteristic of an allergen, an antigen that is characteristic of a tumor and an antigen that serves as an adjuvant (e.g., TLR agonists, such as TLR ligands). The vaccine antigen comprises cells, viruses and/or any component thereof. In some embodiments, the glycosphingolipid-antigen complex serves as an adjuvant and is administered sufficiently close in time with a vaccine (simultaneously or sequentially) to stimulate an individual's response to the vaccine.

In a further embodiment, the invention relates to a glycosphingolipid-therapeutic agent complex comprising a glycosphingolipid attached to a therapeutic agent, wherein the glycosphingolipid comprises a ceramide that comprises (a) a short chain fatty acid (C4-C12) or (b) a long chain fatty acid (C14-C28) comprising at least one cis double bond between two carbon atoms and the therapeutic agent to be delivered is attached to the oligosaccharide of the ganglioside. In specific embodiments, the short chain fatty acid (C4-C12) includes no double bonds between its carbon atoms. In alternative embodiments, the short chain fatty acid (C4-C12) comprises a (one, one or more, at least one) cis double bond between its carbon atoms.

In specific embodiments, the fatty acid of the glycosphingolipid-therapeutic agent complex is (a) a C12 fatty acid (which can be C12 with no double bonds or C12 comprising a (one, one or more, at least one) cis double bond), such as C12 with one double bond (designated C12:1) or (b) a C16 fatty acid comprising a (one, one or more, at least one) cis double bond, such as C16 with one double bond (designated C16:1). The glycosphingolipid of the complex may be selected from the group consisting of neutral glycosphingolipids, such as globosides or acidic glycosphingolipids, such as gangliosides. The ganglioside of the ganglioside-therapeutic agent complex comprises a (one, one or more, at least one) sialic acid and, in a specific embodiment, includes only one sialic acid. In a specific embodiment, the ganglioside of the complex is monosialotetrahexosylganglioside (GM1). The therapeutic agent is, for example, a protein, peptide, nucleic acid, carbohydrate (e.g., polysaccharide), lipid, glycoprotein, and any combinations thereof. Synthetic organic and inorganic drugs that can exert a biological effect when administered to a subject are also included. In addition, glycosphingolipids attached to antigen can be administered as a vaccine and/or to stimulate an individual's response to a vaccine. An antigen is selected from the group consisting of: an antigen that is characteristic of a pathogen, an antigen that is characteristic of an autoimmune disease, an antigen that is characteristic of an allergen, an antigen that is characteristic of a tumor and an antigen that serves as an adjuvant (e.g., TLR agonists, such as TLR ligands). The vaccine antigen comprises cells, viruses and/or any component thereof. In some embodiments, the glycosphingolipid-antigen complex serves as an adjuvant and is administered sufficiently close in time with a vaccine (simultaneously or sequentially) to stimulate an individual's response to the vaccine. The therapeutic agent is, for example, an anti-inflammatory agent, a vaccine antigen, an anti-cancer drug or chemotherapeutic drug, a clotting factor, a hormone, a steroid, a cytokine, an antibiotic, or a drug for the treatment of cardiovascular disease, an infectious disease, an autoimmune disease, allergy, a blood disorder, a metabolic disorder or a skin disease.

In another embodiment, the glycosphingolipid-therapeutic agent complex comprises a glycosphingolipid attached to a therapeutic agent, wherein the fatty acid of the ceramide comprises (a) 4-12 carbon atoms or (b)14-28 carbon atoms with at least one cis double bond between two carbon atoms and wherein the therapeutic agent is attached to the oligosaccharide of the glycosphingolipid. The 4-12 carbon atom fatty acid component can be a fatty acid with no double bonds between carbon atoms. In alternative embodiments, the short chain fatty acid (C4-C12) comprises a (one, one or more, at least one) cis double bond between its carbon atoms.

In specific embodiments, the fatty acid is a C12 fatty acid with no double bonds between carbon atoms (C12:0) or a C16 fatty acid comprising a (at least one, one or more, one) cis double bond and, in a specific embodiment, a C16 fatty acid with one cis double bond (designated C16:1). The glycosphingolipid of the complex may be selected from the group consisting of neutral glycosphingolipids, such as globosides or acidic glycosphingolipids, such as gangliosides. The ganglioside of the ganglioside-therapeutic agent complex comprises a (one, one or more, at least one) sialic acid and, in a specific embodiment, includes only one sialic acid. In a specific embodiment, the ganglioside of the complex is monosialotetrahexosylganglioside (GM1). The therapeutic agent is, for example, a protein, peptide, nucleic acid, carbohydrate (e.g., polysaccharide), lipid, glycoprotein, and any combinations thereof. Synthetic organic and inorganic drugs that can exert a biological effect when administered to a subject are also included. In addition, glycosphingolipids attached to antigen can be administered as a vaccine and/or to stimulate an individual's response to a vaccine. An antigen is selected from the group consisting of: an antigen that is characteristic of a pathogen, an antigen that is characteristic of an autoimmune disease, an antigen that is characteristic of an allergen, an antigen that is characteristic of a tumor and an antigen that serves as an adjuvant (e.g., TLR agonists, such as TLR ligands). The vaccine antigen comprises cells, viruses and/or any component thereof. In some embodiments, the glycosphingolipid-antigen complex serves as an adjuvant and is administered sufficiently close in time with a vaccine (simultaneously or sequentially) to stimulate an individual's response to the vaccine. The therapeutic agent is, for example, an anti-inflammatory agent, a vaccine antigen, an anti-cancer drug or chemotherapeutic drug, a clotting factor, a hormone, a steroid, a cytokine, an antibiotic, or a drug for the treatment of cardiovascular disease, an infectious disease, an autoimmune disease, allergy, a blood disorder, a metabolic disorder or a skin disease.

In a further embodiment, described hereinis a ganglioside-therapeutic agent complex, wherein the ganglioside comprises a ceramide that comprises (a) a short chain (C4-C12) fatty acid or (b) a long chain (C14-C28) fatty acid comprising a (one, one or more, at least one) cis double bond and the therapeutic agent is attached to the oligosaccharide of the ganglioside. The short chain (4-12 carbon atom) fatty acid component can be a fatty acid with no double bonds between carbon atoms. In specific embodiments, the fatty acid is a C12 fatty acid with no double bonds between carbon atoms (C12:0) or a C16 fatty acid comprising a cis double bond and, in a specific embodiment, a C16 fatty acid with one cis double bond (designated C16:1). The ganglioside of the ganglioside-therapeutic agent complex comprises a (one, one or more, at least one) sialic acid and, in a specific embodiment, includes only one sialic acid. In a specific embodiment, the ganglioside of the complex is monosialotetrahexosylganglioside (GM1). The therapeutic agent is, for example, a protein, peptide, nucleic acid, carbohydrate (e.g., polysaccharide), lipid, glycoprotein, and any combinations thereof. Synthetic organic and inorganic drugs that can exert a biological effect when administered to a subject are also included. In addition, glycosphingolipids attached to antigen can be administered as a vaccine and/or to stimulate an individual's response to a vaccine. An antigen is selected from the group consisting of: an antigen that is characteristic of a pathogen, an antigen that is characteristic of an autoimmune disease, an antigen that is characteristic of an allergen, an antigen that is characteristic of a tumor and an antigen that serves as an adjuvant (e.g., TLR agonists, such as TLR ligands). The vaccine antigen comprises cells, viruses and/or any component thereof. In some embodiments, the glycosphingolipid-antigen complex serves as an adjuvant and is administered sufficiently close in time with a vaccine (simultaneously or sequentially) to stimulate an individual's response to the vaccine. The therapeutic agent is, for example, an anti-inflammatory agent, a vaccine antigen, an anti-cancer drug or chemotherapeutic drug, a clotting factor, a hormone, a steroid, a cytokine, an antibiotic, or a drug for the treatment of cardiovascular disease, an infectious disease, an autoimmune disease, allergy, a blood disorder, a metabolic disorder or a skin disease.

In a further embodiment, the invention relates to a ganglioside-therapeutic agent complex comprising monosialotetrahexosylganglioside (GM1) attached to a therapeutic agent, wherein the fatty acid component of the ceramide comprises (a) 4-12 carbon atoms with no double bonds between carbon atoms or (b) 14-28 carbon atoms comprising at least one cis double bond between two carbon atoms and the therapeutic agent is attached to the oligosaccharide of monosialotetrahexosylganglioside (GM1). In specific embodiments, the short chain fatty acid (C4-C12) includes no double bonds between its carbon atoms. In alternative embodiments, the short chain fatty acid (C4-C12) comprises a (one, one or more, at least one) cis double bond between its carbon atoms.

In specific embodiments, the fatty acid of the ganglioside-therapeutic agent complex is (a) a C12 fatty acid (which can be C12 with no double bonds or C12 comprising a (one, one or more, at least one) cis double bond), such as C12 with one double bond (designated C12:1)) or (b) a C16 fatty acid comprising a (one, one or more, at least one) cis double bond, such as C16 with one double bond (designated C16:1). The therapeutic agent is, for example, a protein, peptide, nucleic acid, carbohydrate (e.g., polysaccharide), lipid, glycoprotein, and any combination thereof. Synthetic organic and inorganic drugs that can exert a biological effect when administered to a subject are also included. In addition, glycosphingolipids attached to antigen can be administered as a vaccine and/or to stimulate an individual's response to a vaccine. An antigen is selected from the group consisting of: an antigen that is characteristic of a pathogen, an antigen that is characteristic of an autoimmune disease, an antigen that is characteristic of an allergen, an antigen that is characteristic of a tumor and an antigen that serves as an adjuvant (e.g., TLR agonists, such as TLR ligands). The vaccine antigen comprises cells, viruses and/or any component thereof. In some embodiments, the glycosphingolipid-antigen complex serves as an adjuvant and is administered sufficiently close in time with a vaccine (simultaneously or sequentially) to stimulate an individual's response to the vaccine. The therapeutic agent is, for example, an anti-inflammatory agent, a vaccine antigen, an anti-cancer drug or chemotherapeutic drug, a clotting factor, a hormone, a steroid, a cytokine, an antibiotic, or a drug for the treatment of cardiovascular disease, an infectious disease, an autoimmune disease, allergy, a blood disorder, a metabolic disorder or a skin disease. In a further embodiment, the agent attached to the oligosaccharide of GM1 is a hydrophilic charged group, such as a strong hydrophilic charged group. In one embodiment, this group is flurorophore (e.g., ALEXA, e.g., ALEXA568).

Another embodiment of the invention relates to compositions described herein, such as compositions comprising (a) a delivery vehicle as described herein and (b) a pharmaceutically acceptable carrier. Other compositions comprise (a) a ganglioside-therapeutic agent complex and (b) a pharmaceutically acceptable carrier.

The present invention also relates to methods of delivering an agent, such as a therapeutic agent, into cells/across a mucosal surface. In one embodiment, the method comprises contacting a delivery vehicle described herein with the cells/the mucosal surface, under conditions appropriate for uptake of the agent of interest, alone or attached to the delivery vehicle into the cell or its absorption across the mucosal surface, resulting in delivery of the agent of interest, alone or in conjunction with the delivery vehicle. In some instances, the agent of interest is released from the delivery vehicle and enters the cells or crosses the mucosal surface (not attached to the delivery vehicle). In some instances, the delivery vehicle does so.

In another embodiment, the method is a method of delivering a therapeutic agent across/allowing absorption of a therapeutic agent across mucosal surfaces or other epithelial surfaces, comprising contacting a ganglioside-therapeutic agent complex described herein with the mucosal surface, under conditions appropriate for passage of the therapeutic agent, alone or in attached to the ganglioside-therapeutic agent complex, across mucosal surfaces. In some instances, the therapeutic agent is released from the complex and enters the cells or crosses the mucosal surface (not attached to the ganglioside-therapeutic agent complex). In some instances, the ganglioside-therapeutic agent complex does so.

In further embodiments, the method is a method of delivering an agent into cells/across a mucosal surface in an individual, comprising administering to the individual a delivery vehicle described herein comprising a ganglioside and an agent to be delivered or a composition comprising such a vehicle described herein and a pharmaceutically acceptable carrier.

In further embodiments, the method is a method of delivering a therapeutic agent into cells/across a mucosal surface in an individual, comprising administering to the individual a ganglioside-therapeutic agent complex described herein or a composition described herein comprising (a) a ganglioside-therapeutic agent complex and (b) a pharmaceutically acceptable carrier.

In each of the embodiments, whether a delivery vehicle-agent of interest or a ganglioside-therapeutic agent complex or a composition comprising either is administered, administration can be enteral/nonparenteral or parenteral.

In another embodiment, the invention relates to a method of enhancing/increasing the half life of a therapeutic agent in an individual, comprising administering to the individual a delivery vehicle comprising a ganglioside and an agent to be delivered, wherein the agent is a therapeutic agent or a ganglioside-therapeutic agent complex described herein. In specific embodiments, a composition comprising a delivery vehicle or a ganglioside-therapeutic agent complex is administered to the individual. In each of the embodiments, whether a delivery vehicle-agent of interest, a ganglioside-therapeutic agent complex or a composition comprising either is administered, it can be administered enterally/nonparenterally or parenterally.

In another embodiment, the invention relates to a method of treating a disease or condition in an individual in need thereof, comprising administering an effective amount of a delivery vehicle comprising a ganglioside and an agent to be delivered, wherein the agent is a therapeutic agent or a ganglioside-therapeutic agent complex to the individual, wherein an effective amount is an amount sufficient to ameliorate/reduce the extent to which the disease or condition occurs in the individual. In specific embodiments, a composition comprising a delivery vehicle or a ganglioside-therapeutic agent complex is administered to the individual. In each of the embodiments, whether a delivery vehicle-agent of interest, a ganglioside-therapeutic agent complex or a composition comprising either is administered, it can be administered enterally/nonparenterally or parenterally.

The significance of the instant invention is particularly evident in the area of drug delivery and development. It addresses two major problems in the field: macromolecular transport across mucosal barriers and drug half-life. Most protein therapeutics cannot be absorbed across mucosal surfaces (such as the intestine) rendering them clinically ineffective by oral administration and restricted to parenteral forms of drug delivery. This technology overcomes these problems. Further, the technology offers a way to target therapeutic molecules to mucosal surfaces by local (topical) administration, making it possible to treat mucosal diseases, such as inflammatory bowel disease, without systemic toxicities

BRIEF DESCRIPTION OF THE FIGURES

FIGS. 1A—C12:0, FIG. 1B—C16:1, FIG. 1C—C16:0 and FIG. 1D—C20:0.

Figure 15:
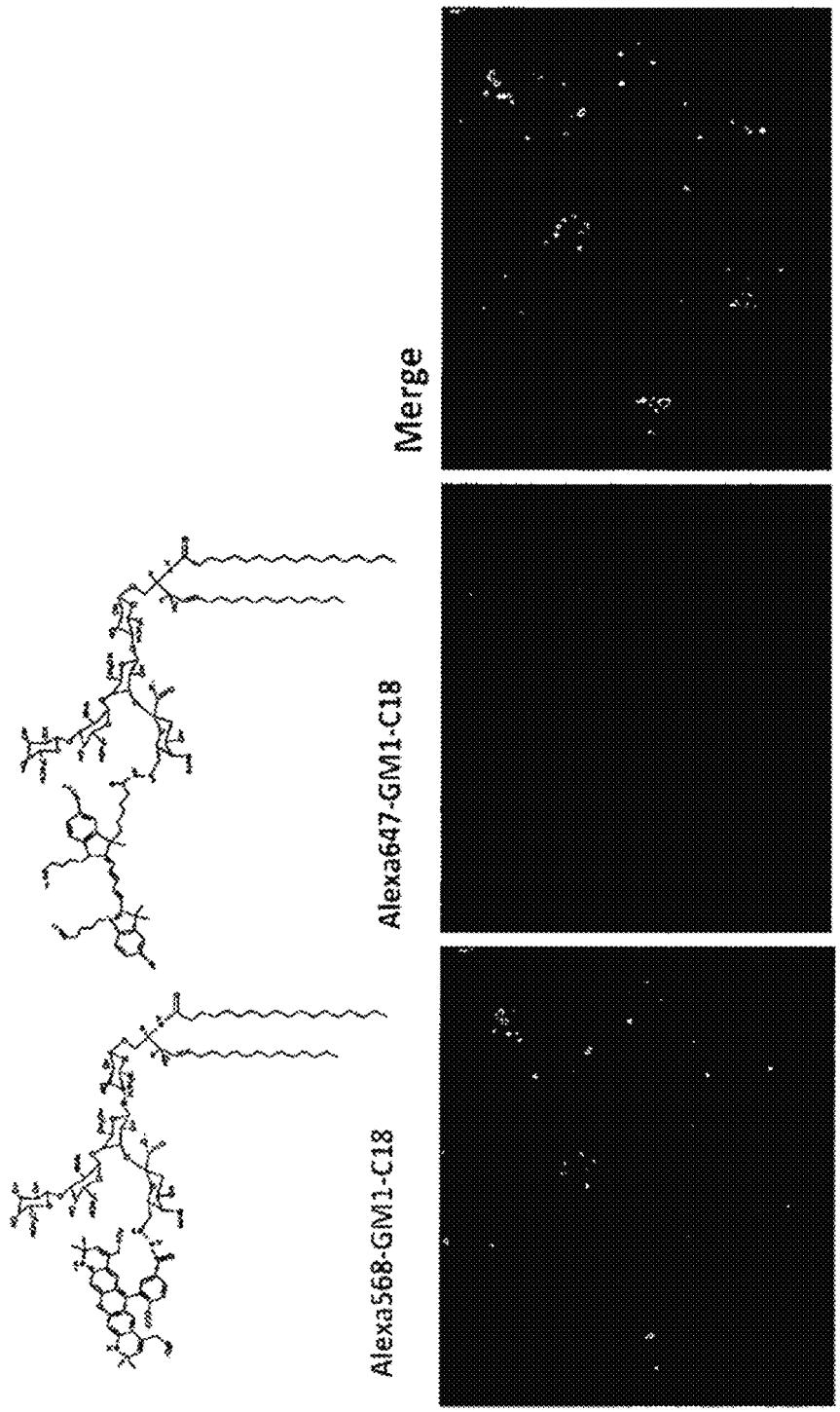

The results shown in FIG. 15 demonstrate that the two Alexa flurophore head groups, Alexa568 and Alexa 647, do not affect GM1 distribution at steady state.

Figure 16:
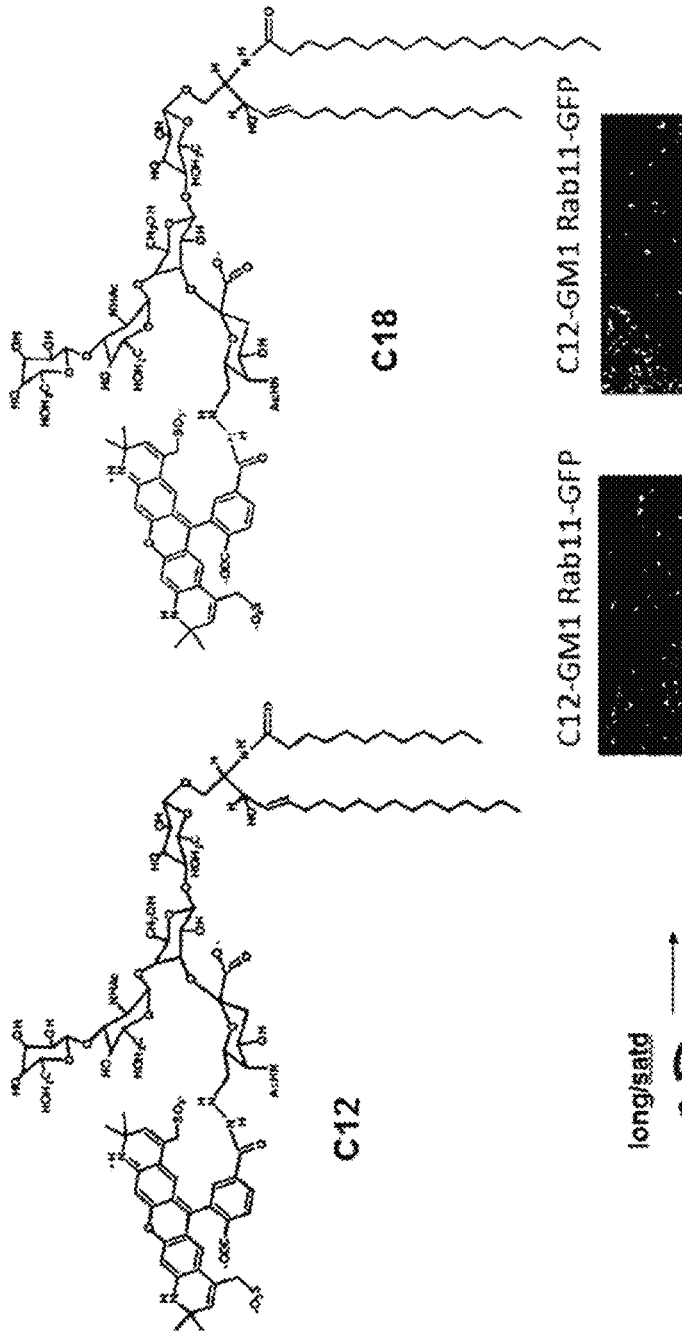

In FIG. 16, live A431 human epithelial cells were loaded with GM1 isoforms. Tubule formation was observed with short chain (C12) GM1(left), whereas no tubule formation is seen with long chain C18 GM1 and is found in lysosomal puncta (right). This is evidence that the short chain can enter into sorting tubules that sort the lipid away from the degradative pathway.

Figure 17:
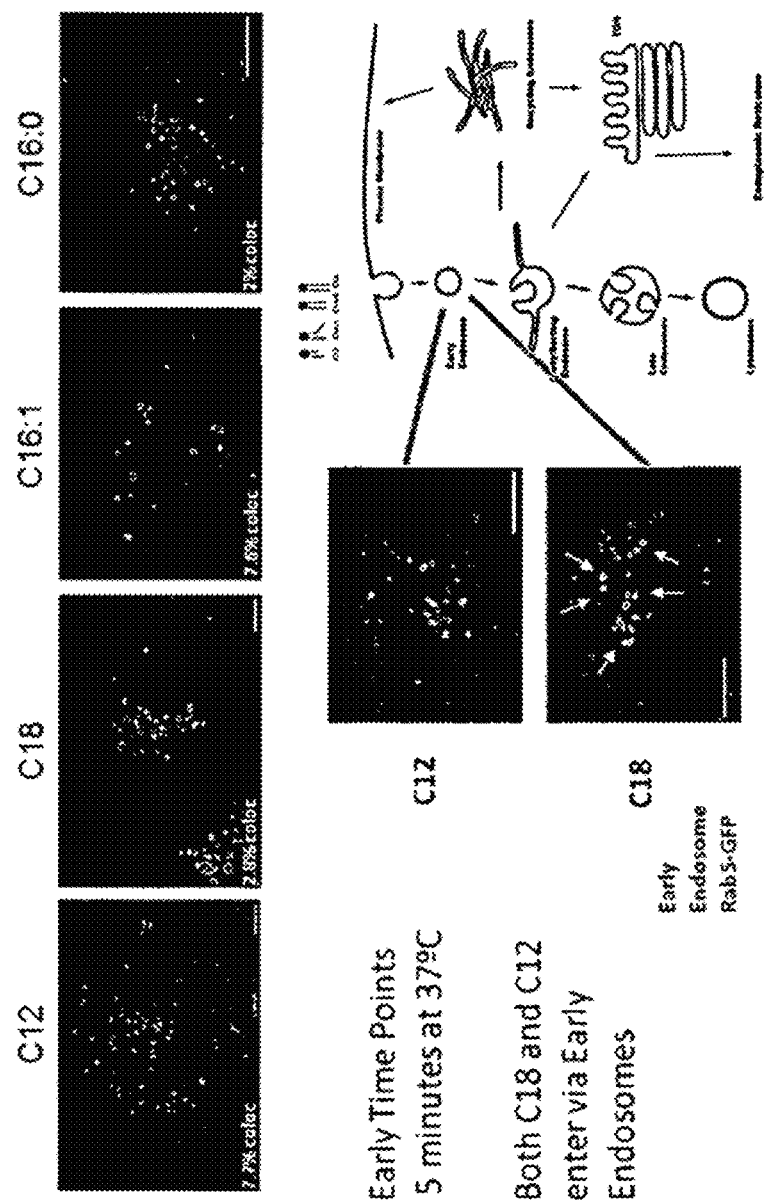
Figure 17:
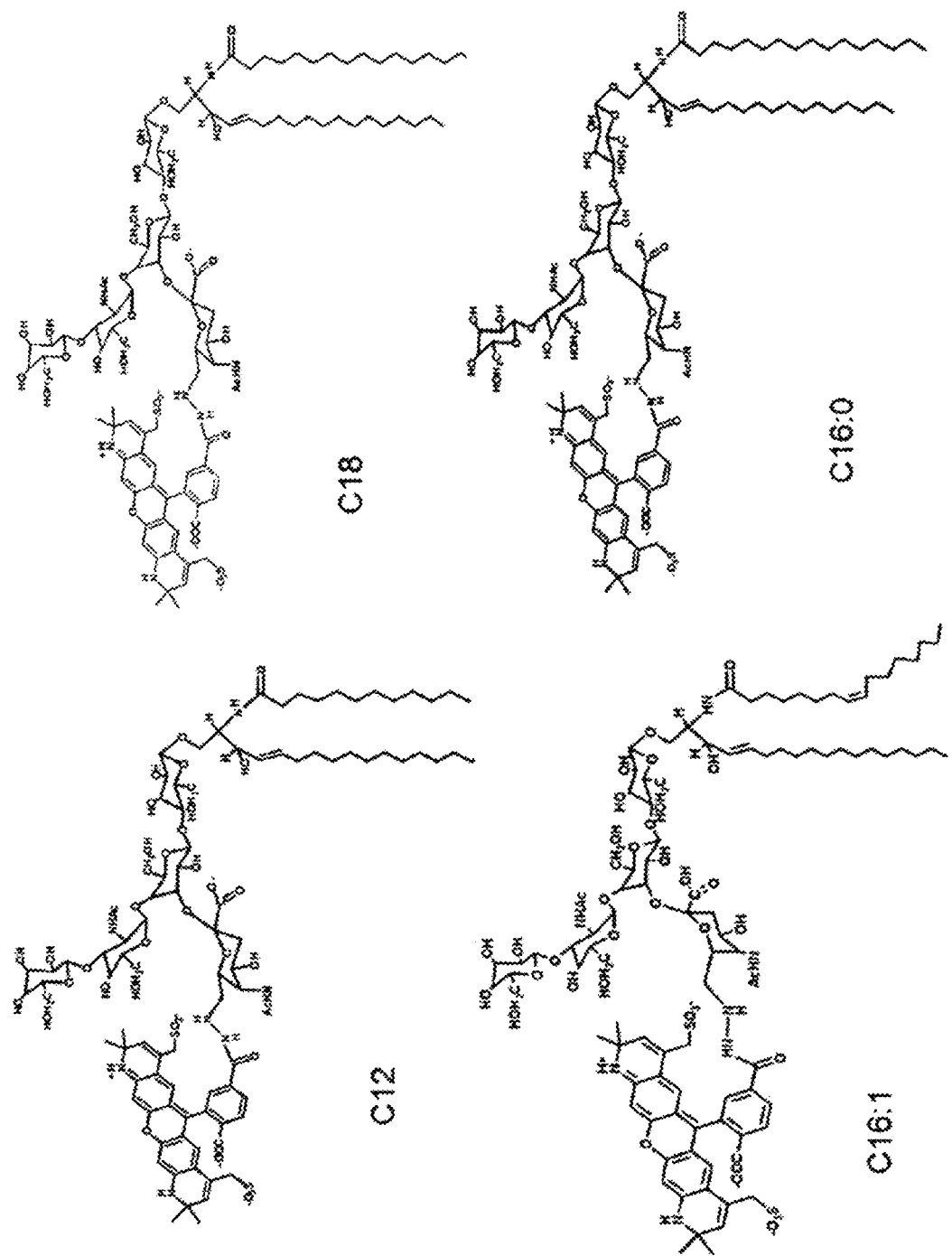

The results shown in FIG. 17 demonstrate that both C12 and C18 ceramides enter the early endosomes.

Figure 18:
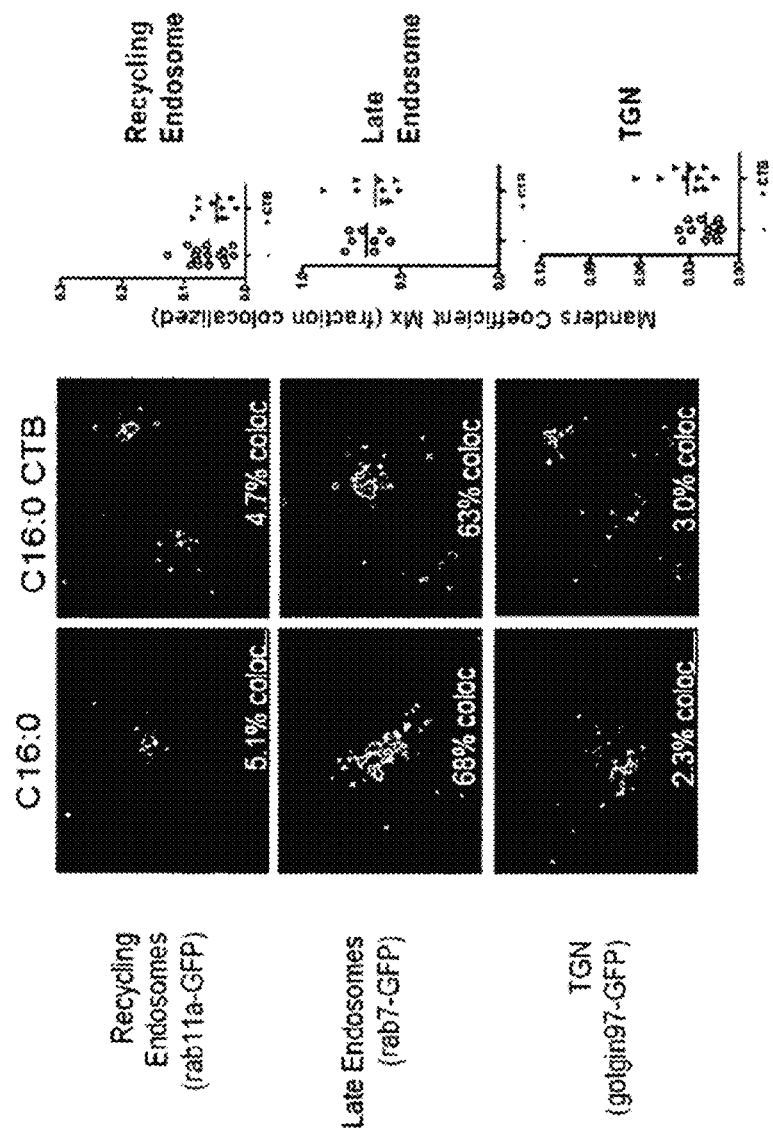
Figure 18:
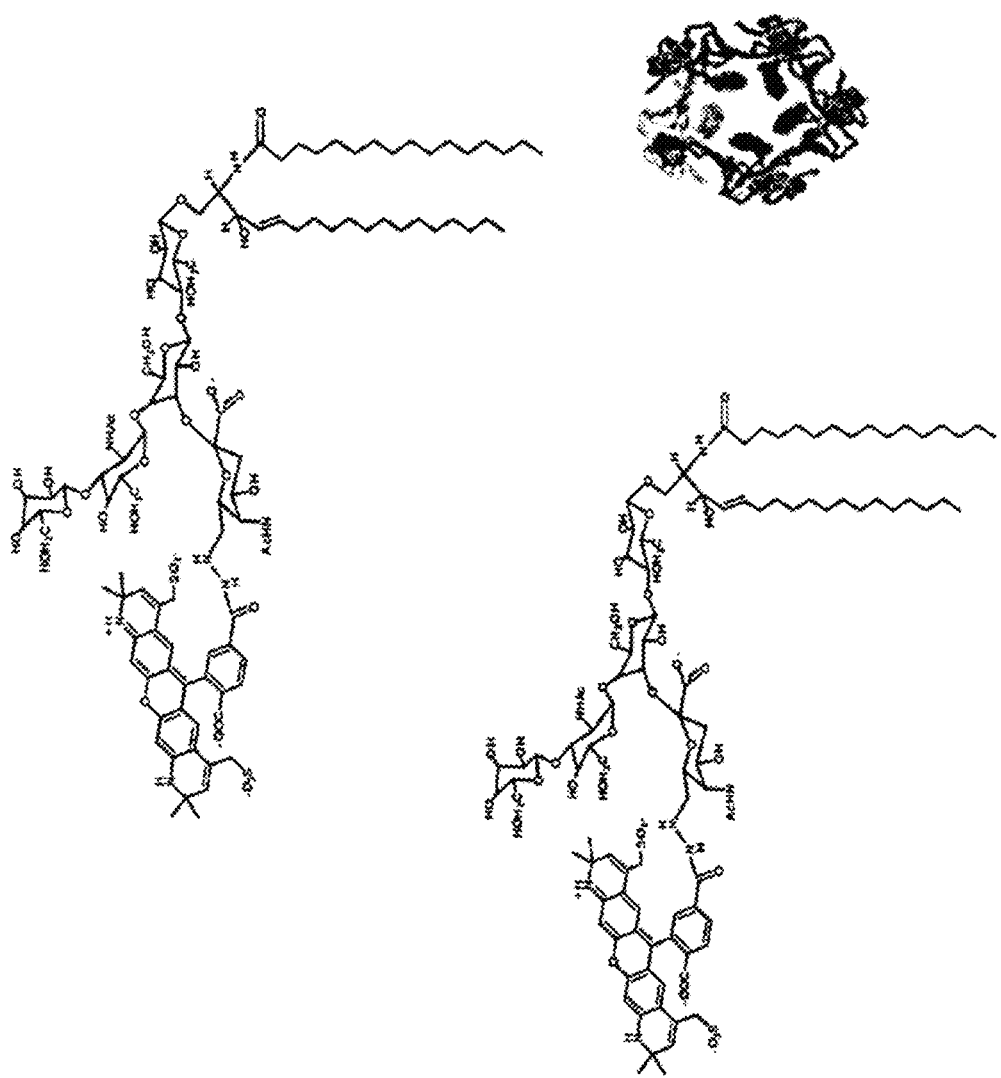

FIG. 18 shows that crosslinking GM1 with cholera toxin does not affect long chain ceramide trafficking.

Figure 19:
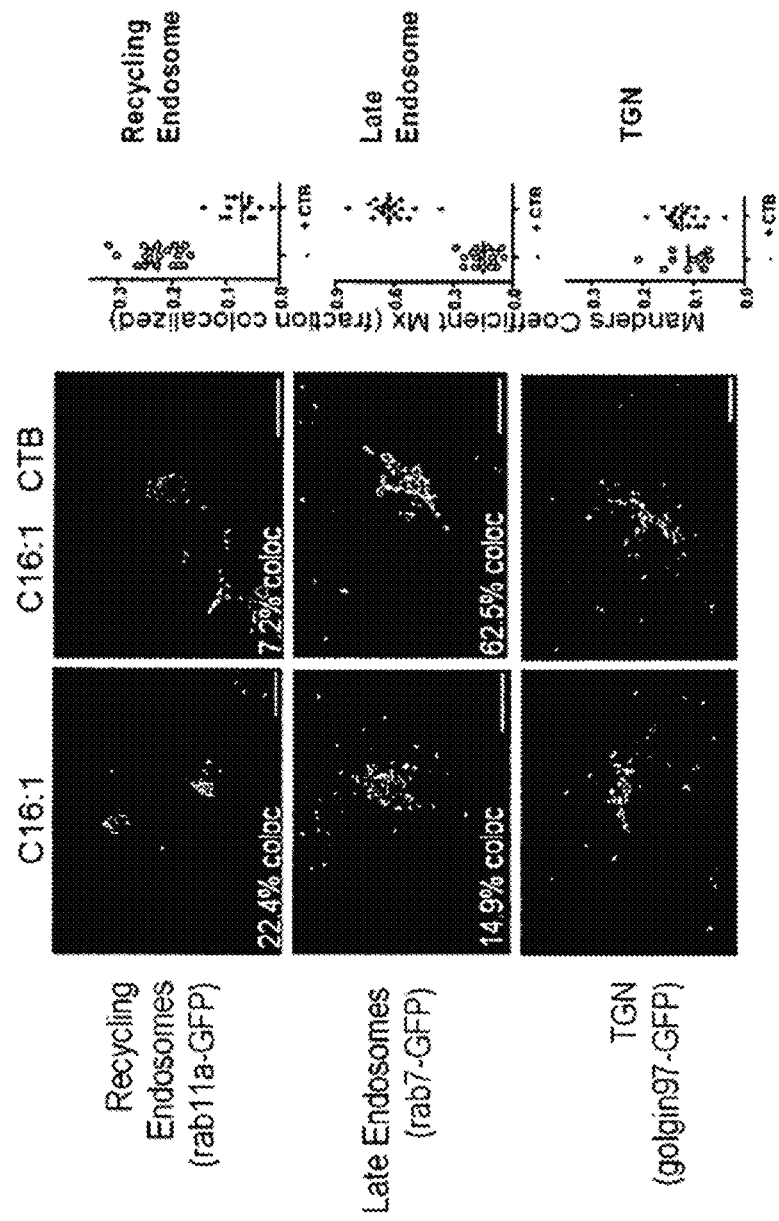
Figure 19:
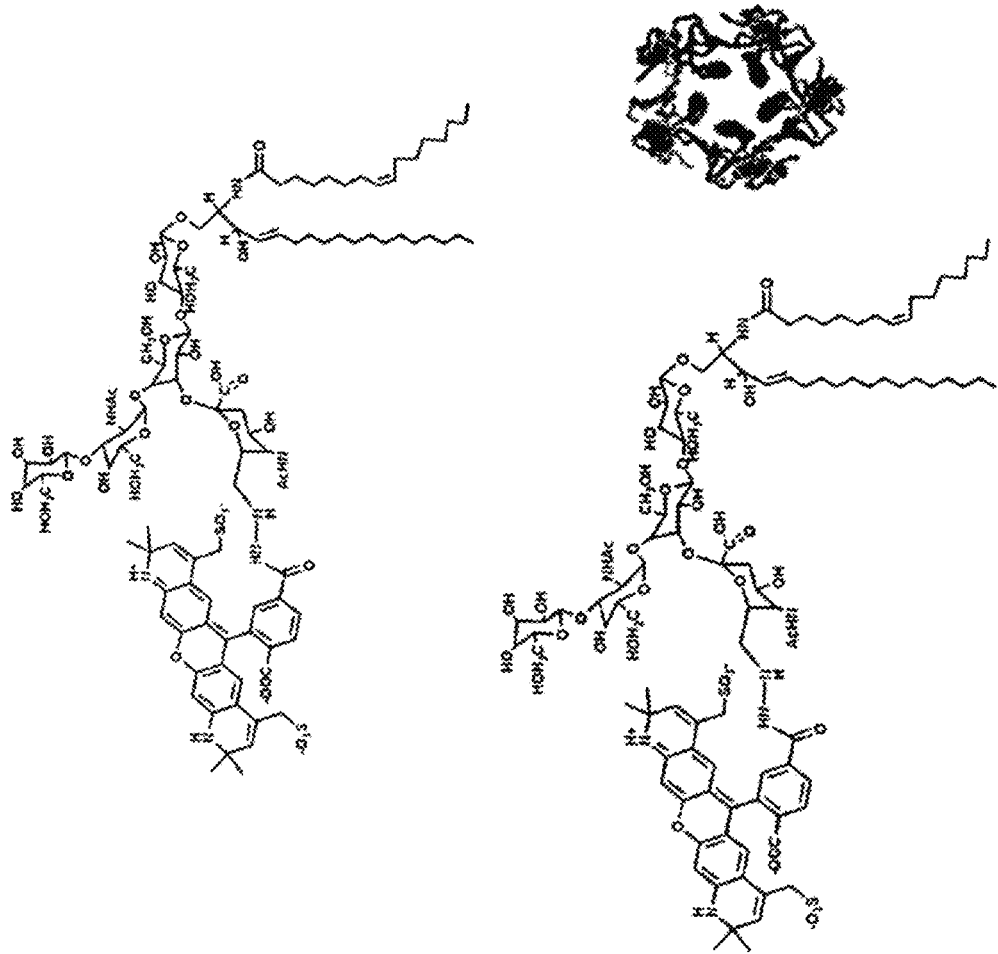

FIG. 19 shows that cross-linking GM1 with cholera toxin redistributes the "kinked" ceramides from RE to LE, while trafficking to the TGN is unchanged. The toxin was applied to cells loaded with the unsaturated chain ceramides (right panels) and compared them to controls (left panels). Clustering the unsaturated ceramides shifted trafficking out of the recycling pathway (compare left and right top panels) and into the late endosome (middle panels). Transport to the TGN, however, was not affected (bottom panels).

Figure 20:
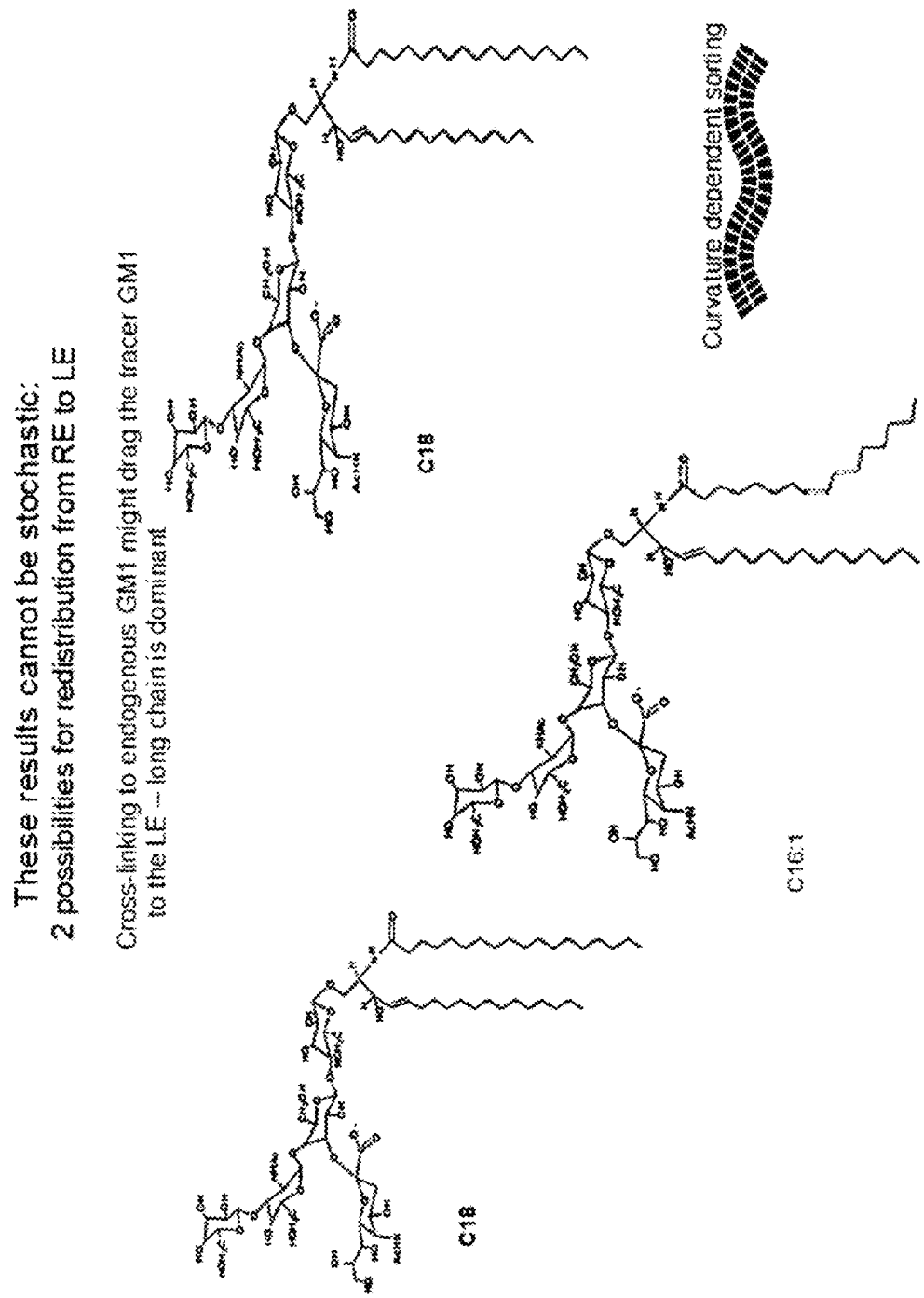
Figure 20:
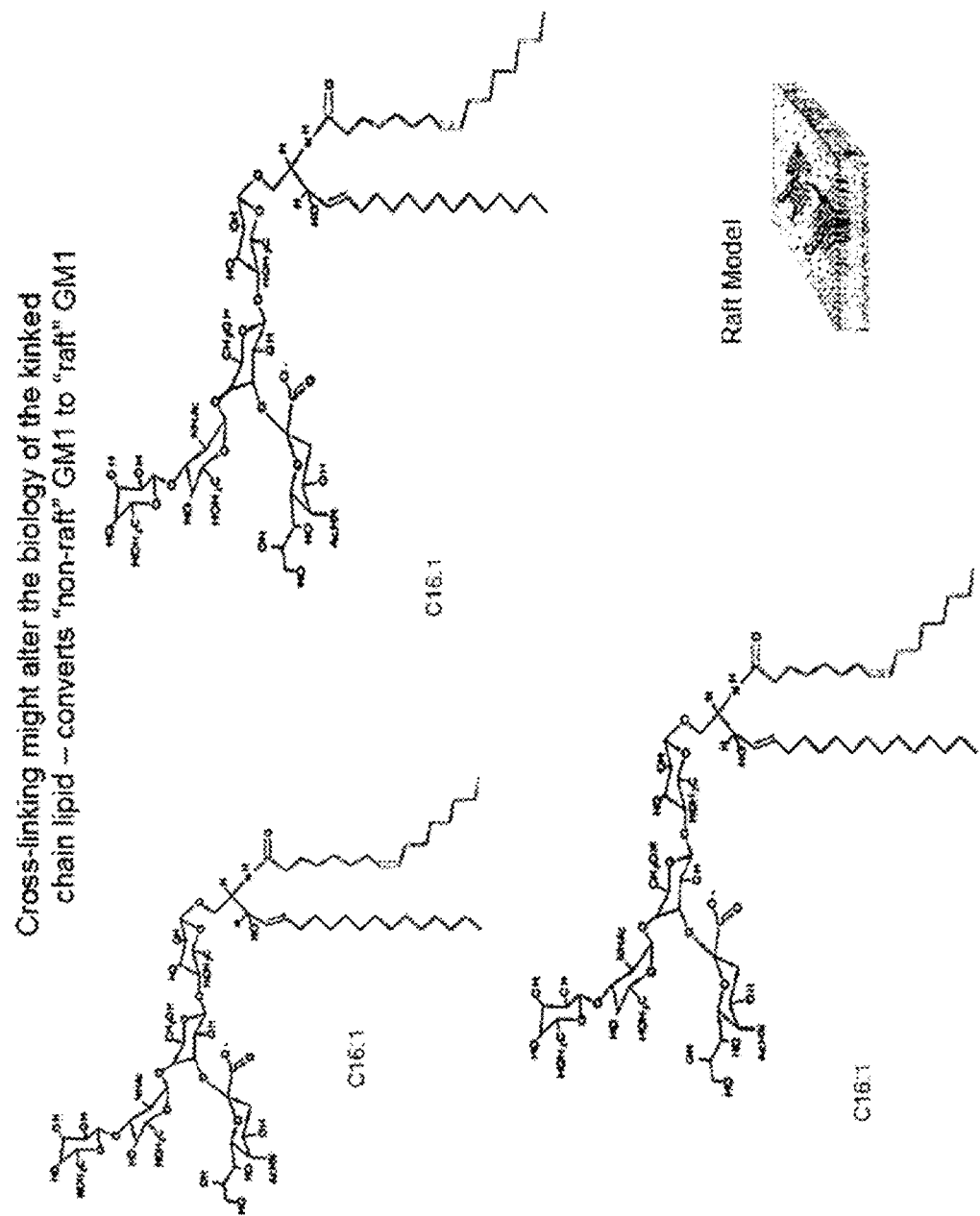

FIG. 20 show that the results cannot be stachastic. There are 2 possibilities: One is that the toxin cross-links both tracer and endogenous gangliosides, with the bulk of endogenous ceramide chains being long chain and acting dominantly. The other is that clustering the unsaturated chain ceramides alters the biology of the lipids—so that microdomains are formed and trafficking is diverted to the LE.

Figure 21:
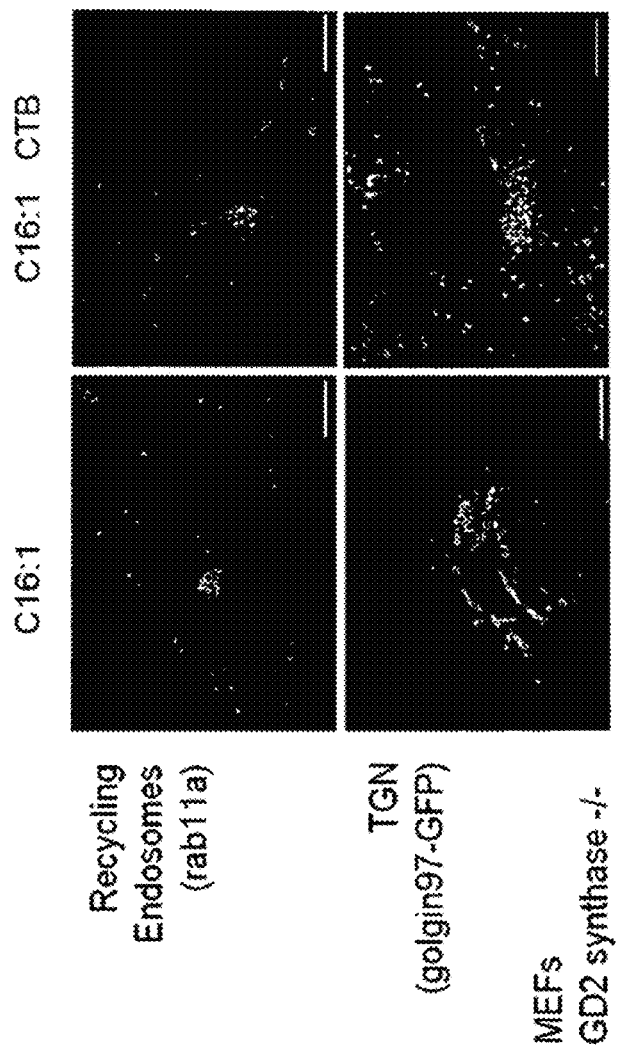
Figure 21:
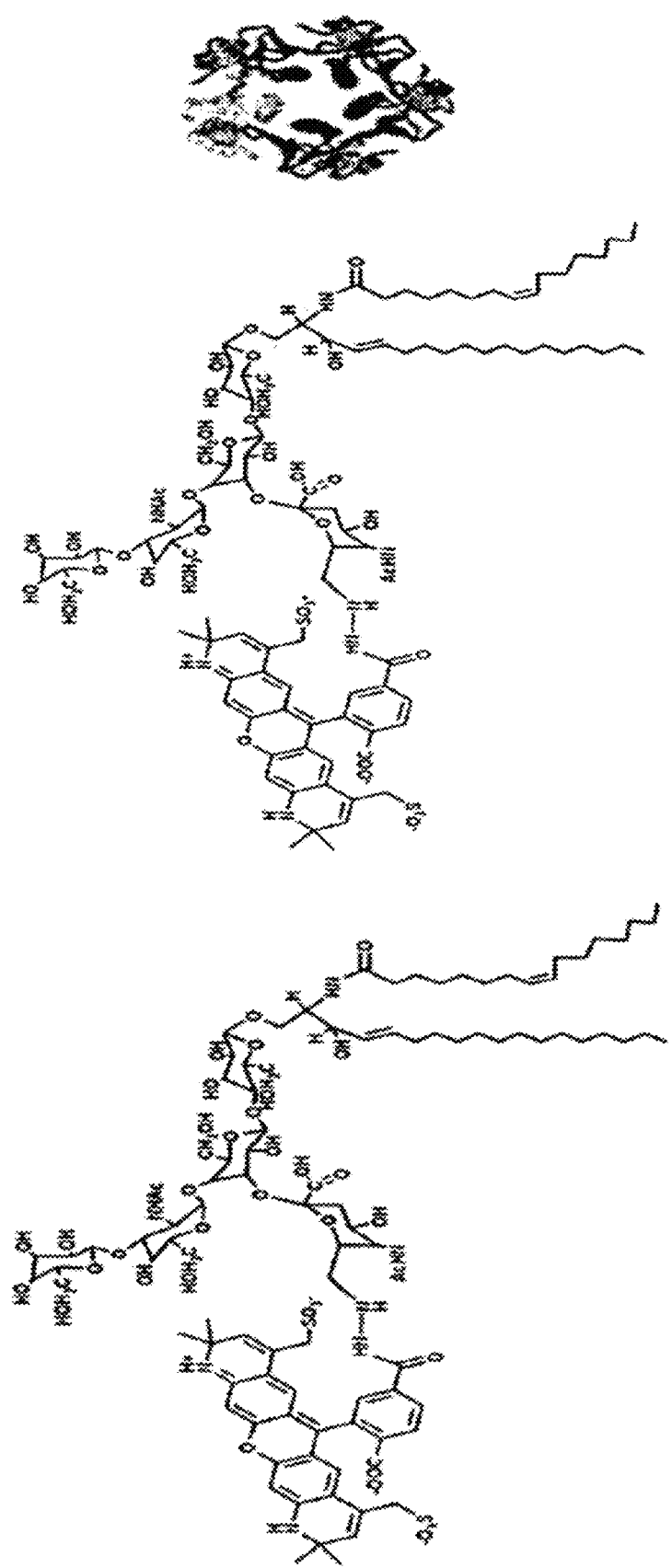

FIG. 21 shows that in cells lacking GM1—cross-linking the "kinked" ceramide (right panels) has no effect on trafficking to the RE or TGN (compare with controls in the left panels). Mouse Embryonic Fibroblasts lacking gangliosides altogether (cells derived from the GD2 synthase KO mouse) were used.

Figure 22:
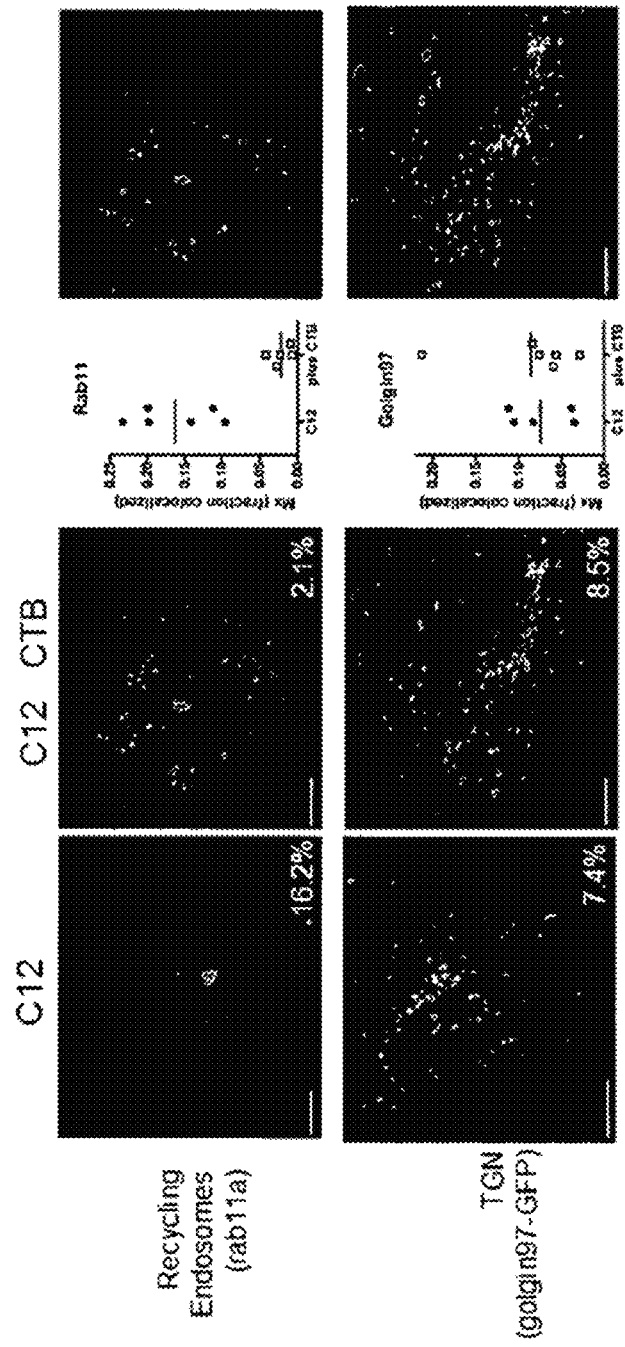
Figure 22:
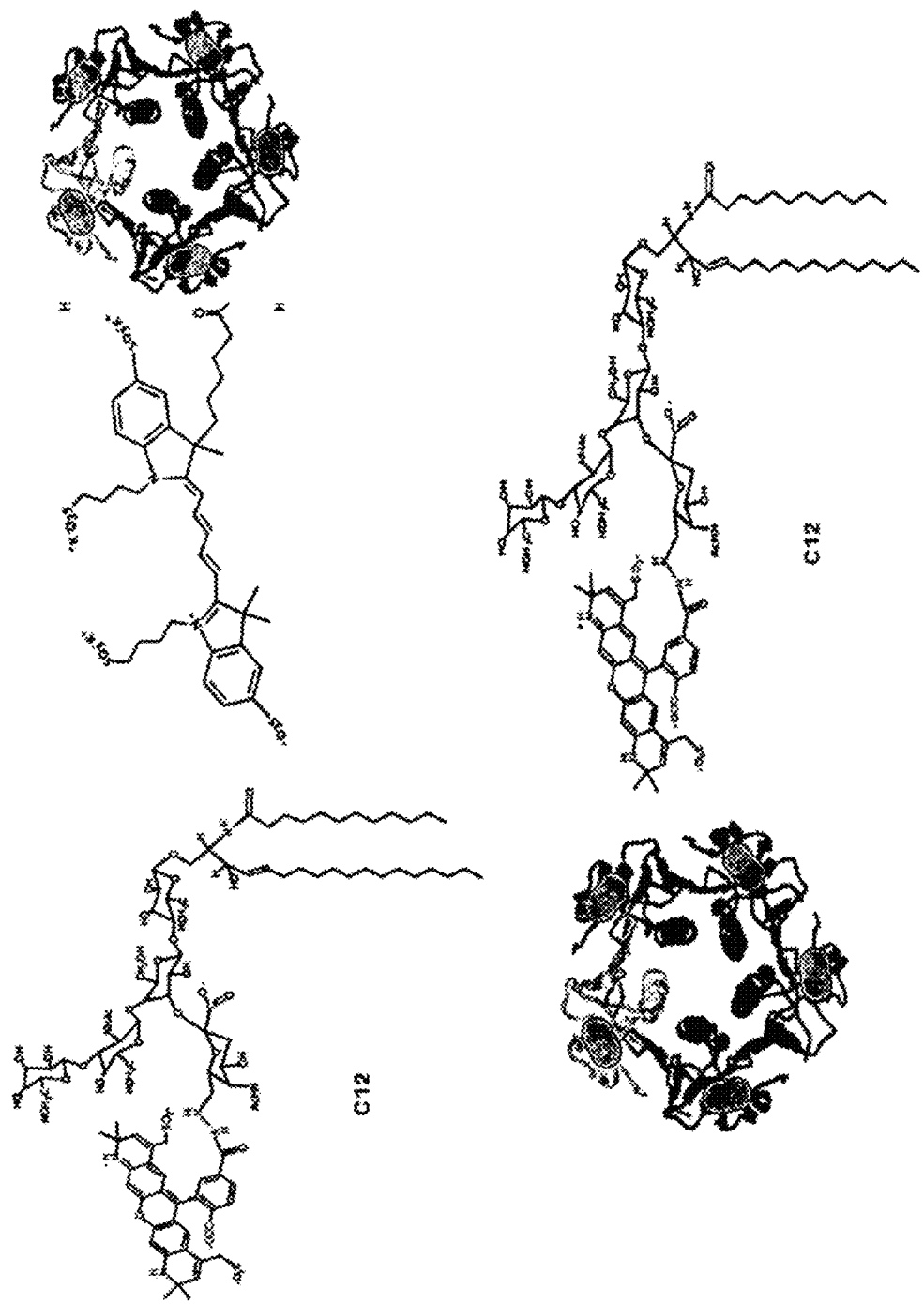

FIG. 22 shows that in cells lacking GM1—short chain C12-GM1 is diverted away from RE after CTB cross-linking-but trafficking to TGN is "rescued."

Figure 23:
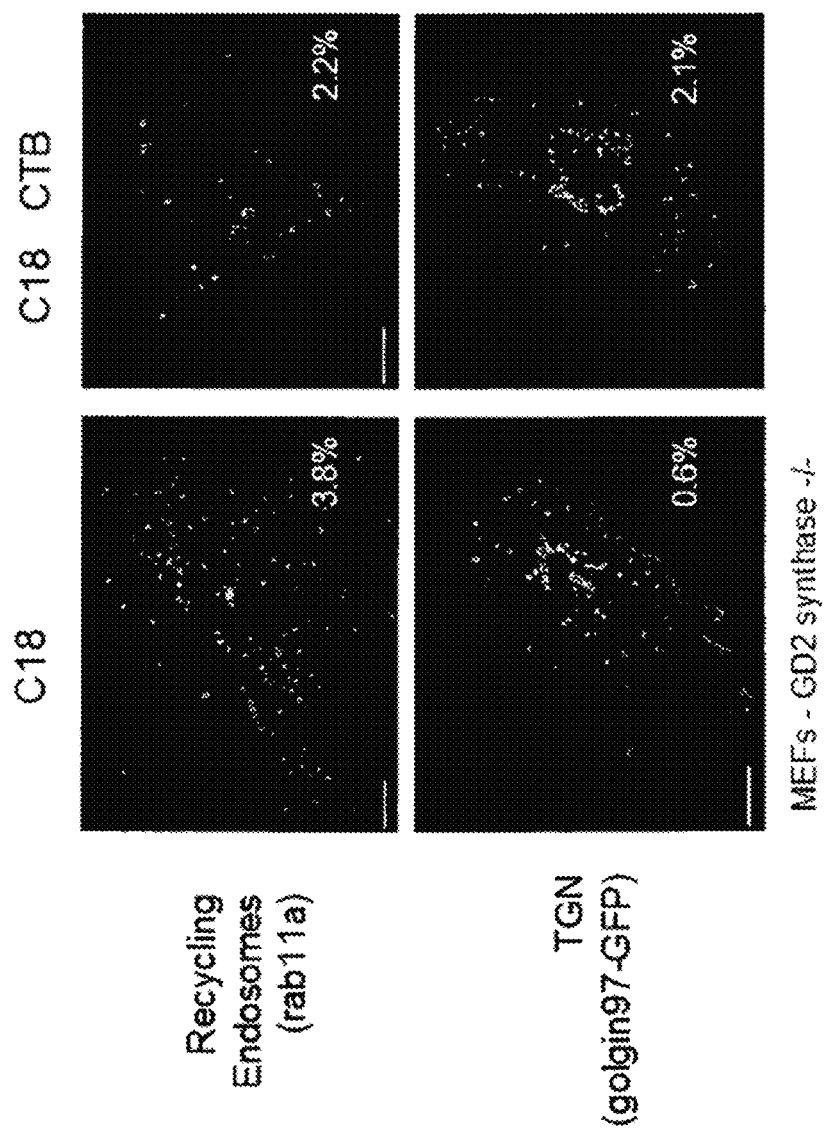
Figure 23:
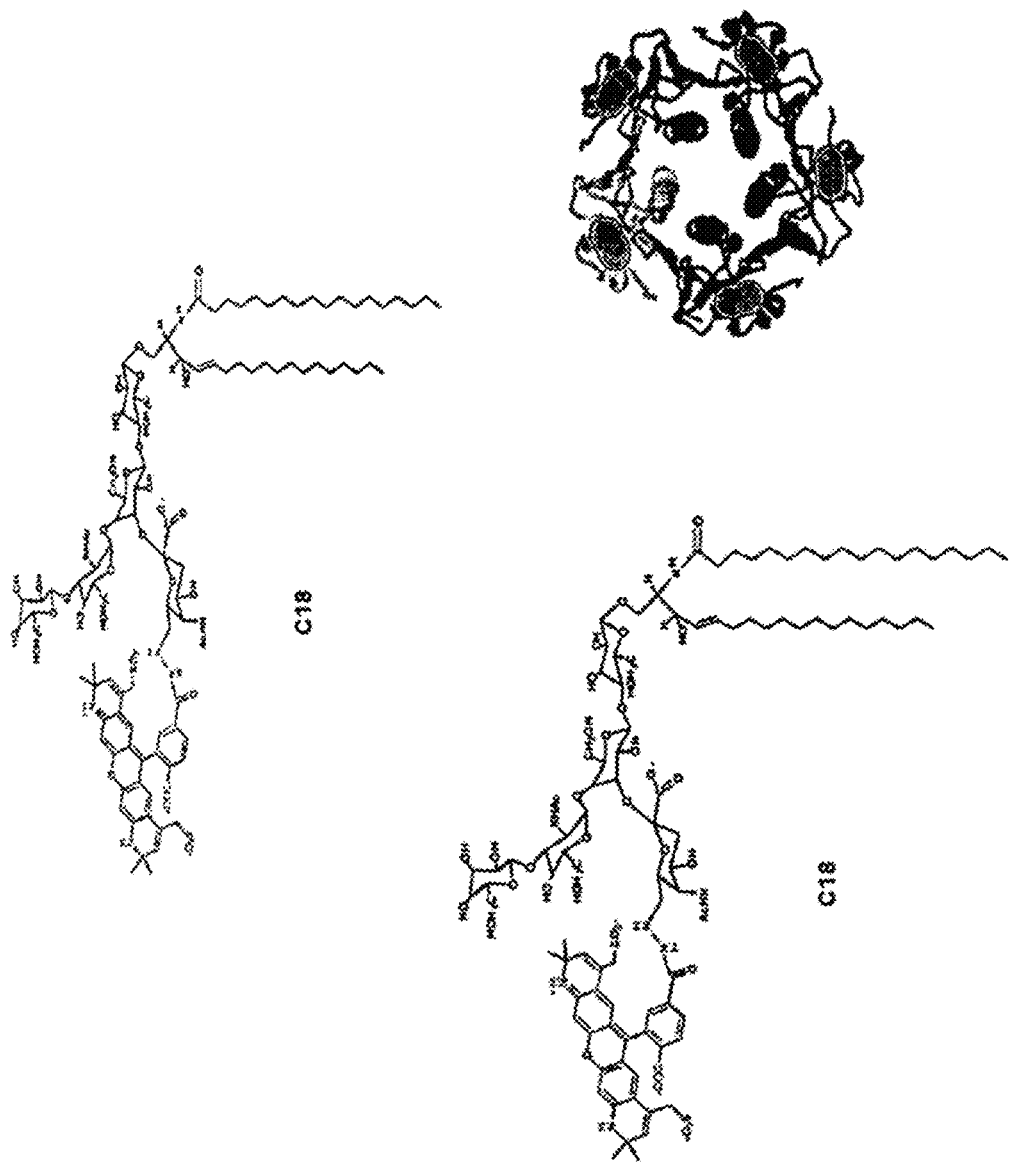

FIG. 23 shows that cross-linking to long chain GM1 has no effect. The long chain ceramide sorts away from the RE or TGN in MEFs.

Figure 24:
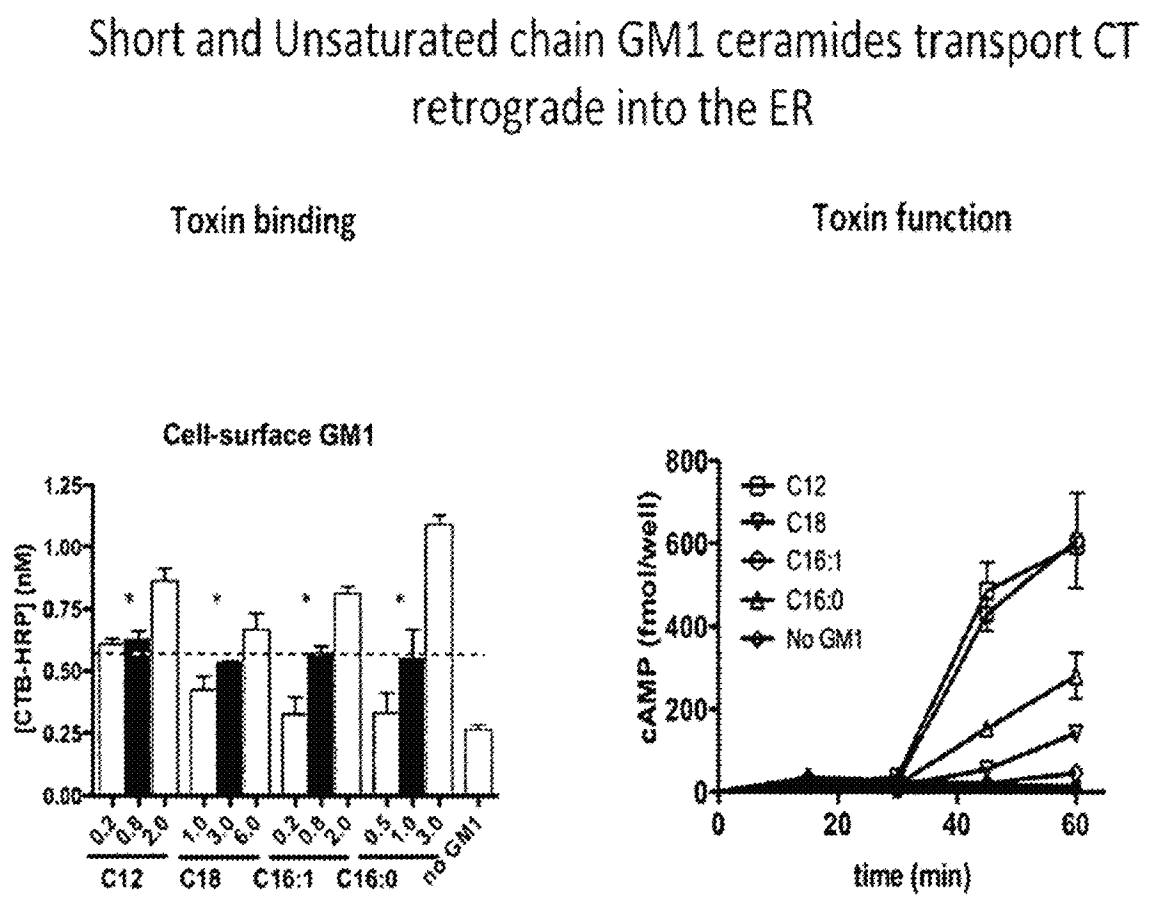

FIG. 24 shows that when GM1 of different structures are loaded onto the cell surface at equal amounts (concentrations in black bars on left graph), and cholera toxin is added to cells, the C12 and C16:1 GM1 lipids sort the toxin more efficiently than the long chains i.e., causes more toxicity at shorter times as assayed by measurement of cAMP levels (right graph).

Figure 25:
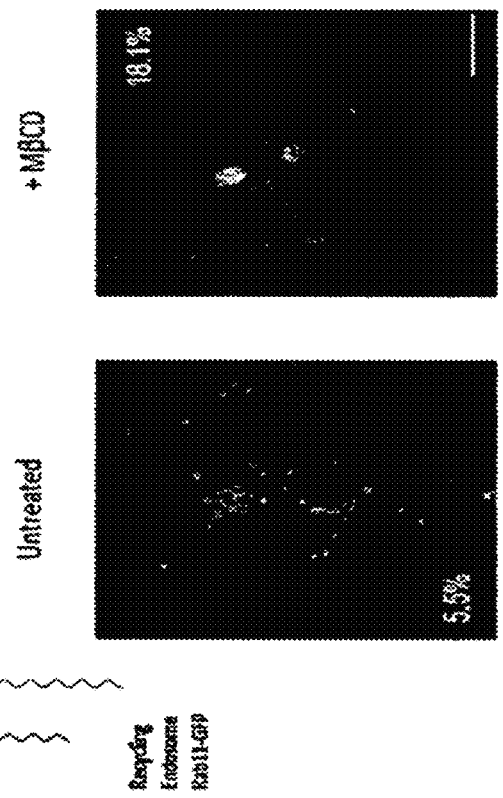
Figure 25:
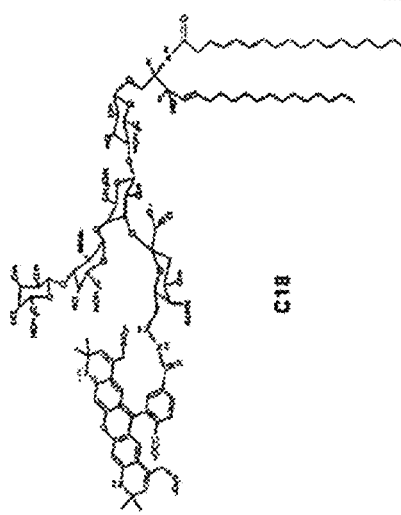

FIG. 25 shows results which demonstrate the critical point behavior: long chain C18 GM1 traffics to the RE (and PM) in cholesterol depleted A431 cells.

Figure 26:
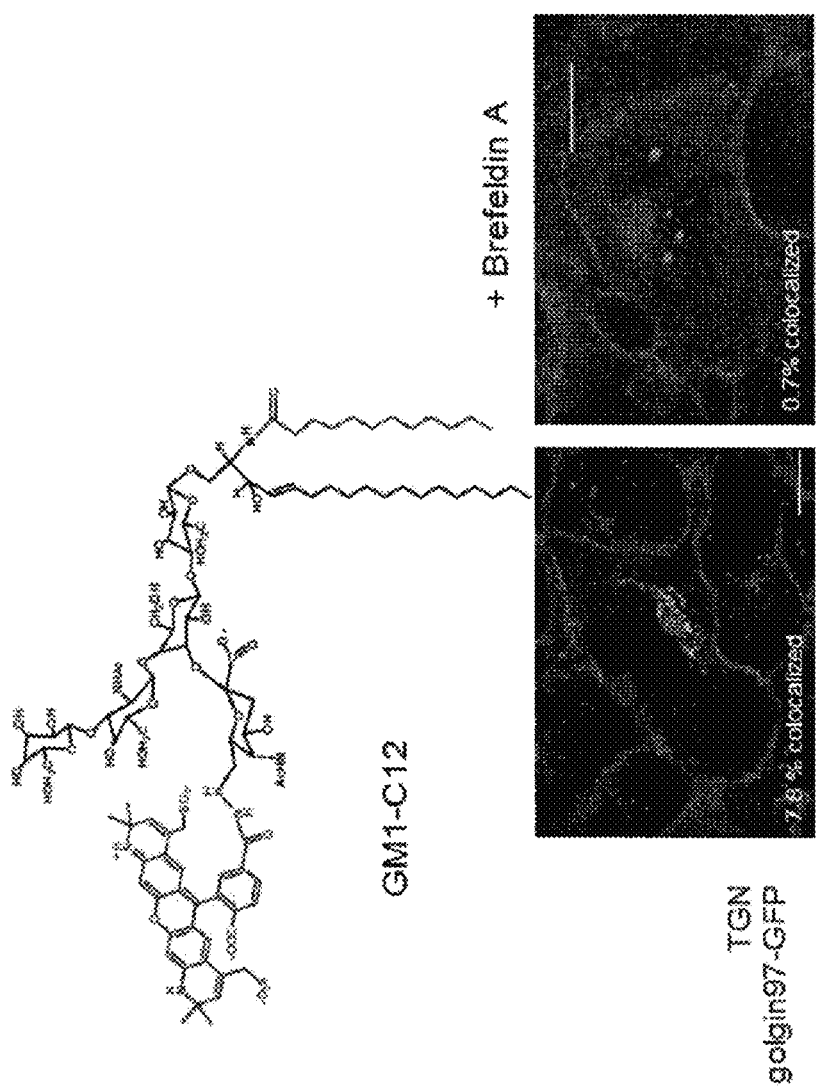

FIG. 26 shows that application of Brefeldin-1 inhibits C12-GM1 transport to the TGN.

Figure 27:
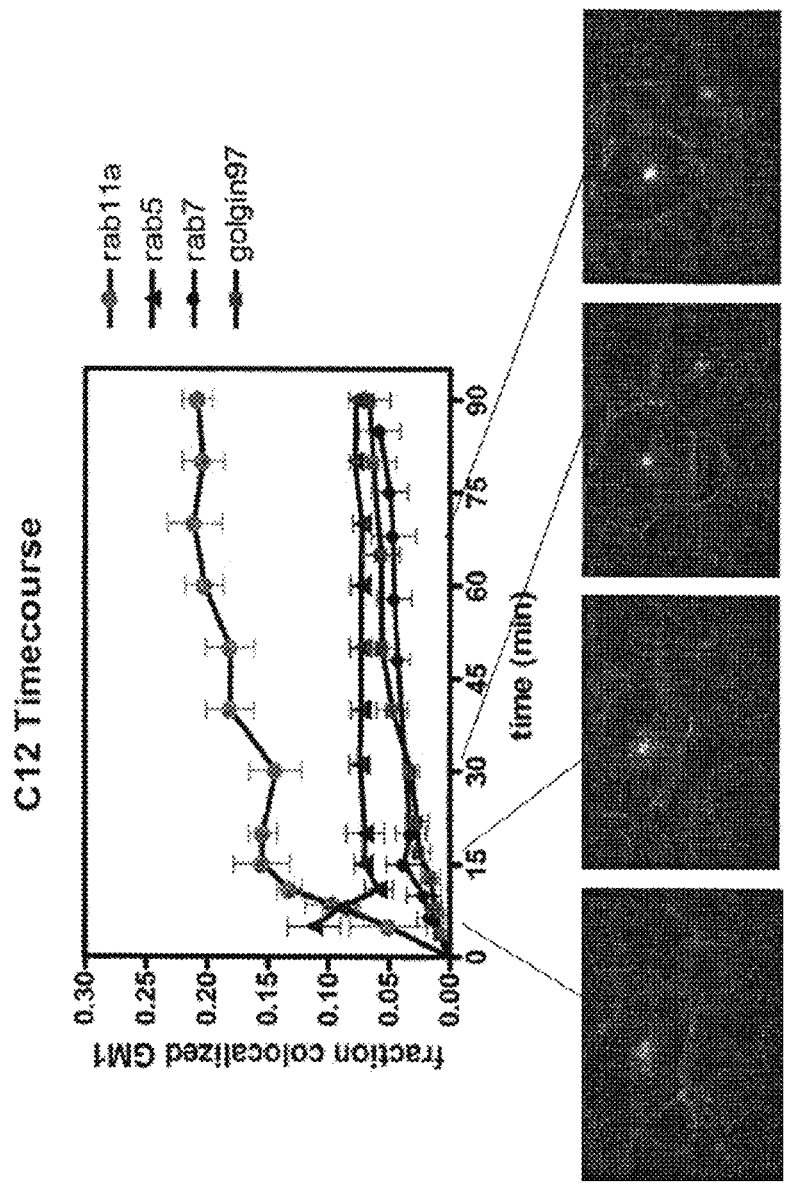

FIG. 27 is a graphical representation of the imaging time course of C12-GM1 trafficking.

Figure 28:
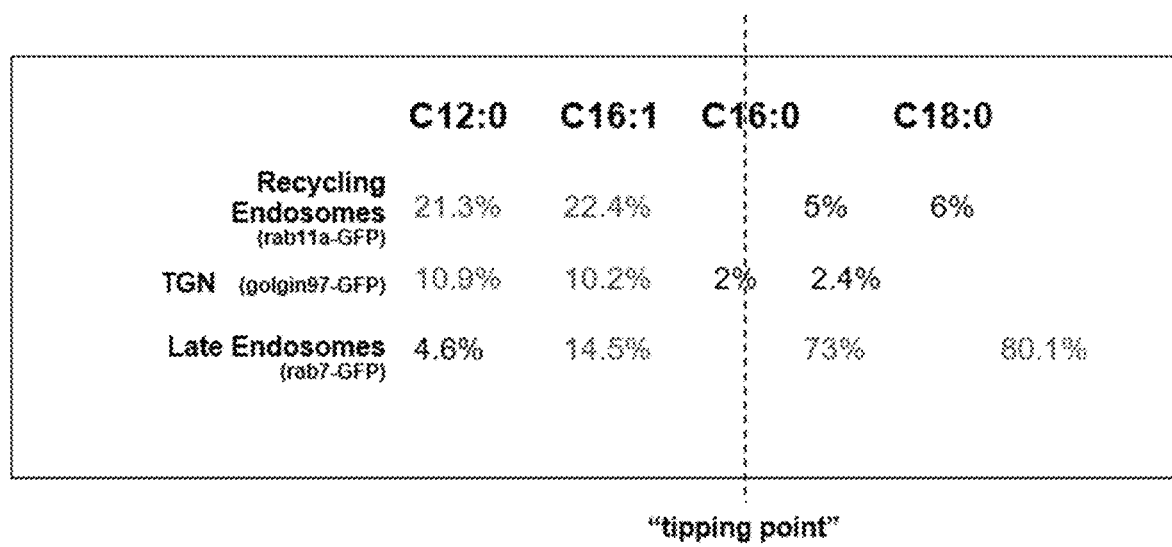

FIG. 28 shows localization of ceramides.

DETAILED DESCRIPTION

Sorting of proteins and lipids to various intracellular compartments of eukaryotic cells depends on movement of membranes through the secretory and endocytic pathways by vesicular carriers. Membrane domains exit from one compartment by budding into smaller transport vesicles or tubules. Both events require the formation of sharp bends in the donor membrane so as to form the transport carriers. Specialized proteins assemble on the cytoplasmic surface of the donor compartment (membrane "coats") to initiate such curvature. Clathrin-coated vesicles typify these structures. The budded vesicles or tubules are then targeted to the acceptor compartment, where they are induced to fuse by assembly of other protein complexes.

Proteins typically move within these transport pathways according to multiple and hierarchically ordered sorting determinants structurally encoded within the protein itself or within the structure of an associated receptor or chaperone. Protein sorting is highly efficient and specific, typified, for example, by E-cadherin, Na/K-ATPase, or some of the beta-integrins, which are strictly expressed on the basolateral membrane of polarized epithelial cells, or the chaperone Bip, which is targeted to the ER lumen.

In contrast to proteins, the sorting of lipids is not as absolute. The mechanisms that regulate differential lipid transport through the intracellular trafficking pathways remain undefined. One major idea in the field is that lipid structure dictates sorting into various compartments by permitting or restricting the lipid's movement across the highly dynamic and sharp curves and bends of budding vesicles and tubules (Maxfield and McGraw, 2004; Mukherjee and Maxfield, 2000; Mukherjee et al., 1999). Another biologically credible idea is the lipid raft hypothesis (Brown, 2006; Simons and Ehehalt, 2002; Simons and Vaz, 2004), which proposes the self-assembly of small domains containing specific lipids such as gangliosides and proteins with regulated biologic functions, including especially trafficking and signal transduction.

Gangliosides, such as monosialotetrahexosylganglioside (GM1), are comprised of two major domains: a sialic acid-containing oligosaccharide head group linked to one or more sialic acids that protrudes from the cell membrane into the extra-cellular space and the hydrophobic ceramide lipid tail that anchors the molecule to the membrane. Ceramides are composed of a sphingosine chain (almost always C18:1; nomenclature is carbon chain length: number of double bonds) coupled by amide linkage to a fatty acid. Native ceramides in human cells show heterogeneity in the structure of the fatty acid, most typically by length of the carbon chain and degree of saturation. (The number of carbon-carbon double bonds). Most naturally-occurring unsaturated fatty acids occur in the cis configuration, in which the hydrogen atoms are on the same side of the double bond. This causes the hydrocarbon chain of the fatty acid to bend, thereby introducing a "kink" in the fatty acid. Increasing the number of cis double bonds in a fatty acid increases the extent to which it is curved (its kinkiness) and restricts its conformational freedom and flexibility.

GM1, the "prototypic" member of gangliosides, is the lipid receptor for cholera toxin, which typifies the biology for all other AB5-subunit toxins (*Shigella, E. coli, Pertussis*) and some viruses (SV40 and the human Polyoma viruses) (Lencer and Tsai, 2003). GM1 is the vehicle that carries the toxin all the way from the plasma membrane (PM) of the host cell to the endoplasmic reticulum (ER). Once inside the ER, the ER chaperone protein disulfide isomerase unfolds a portion of the toxin for retro-translocation to the cytosol, where the peptide acts to induce toxicity (Lencer and Tsai, 2003; Tsai et al., 2001). GM1 also carries the toxin across polarized epithelial cells by transcytosis, thus providing a pathway for the bacterial protein to breech mucosal barriers (Lencer et al., 1995). The two pathways, one retrograde from PM to ER, and the other transcytotic, diverge in their intracellular itinerary at the early sorting endosome (Lencer and Saslowsky, unpublished data).

As described herein, Applicants have shown that the fatty acid structure of the ceramide domain of a ganglioside dictates the intracellular trafficking of the lipid. As also described herein, ceramide isoforms comprising short chain fatty acids or fatty acids, such as long chain fatty acids, with at least one cis double bond localize to the recycling endosome and trans Golgi and ceramide isoforms comprising saturated long fatty acid chain are directed to the lysosomal pathways of cultured human epithelial cells. The invention described herein relates, in one aspect, to novel glycosphingolipid-therapeutic agent complexes. A complex comprises a glycosphingolipid comprising a ceramide of specific structure joined to a therapeutic agent to harness intracellular trafficking and, thus, increase the half-life of the therapeutic agent (by avoiding lysosomal transport) and/or to deliver such therapeutic agent across mucosal barriers (by transcytosis).

Glycosphingolipids minimally comprise a monosaccharide attached directly to a ceramide. In some embodiments, the glycosphingolipid comprises neutral globosides, such as globotriaosyl ceramide ($Gb_3$). In other embodiments, the glycosphingolipids comprises acidic gangliosides, such as monosialotetrahexosylganglioside (GM1). In specific embodiments, a ganglioside-therapeutic agent/moiety complex, also referred to as a glyco-ceramide-therapeutic agent complex, comprises a ceramide that comprises (a) a short chain fatty acid (C4-C12) or (b) a long chain fatty acid (C14-C28) comprising a cis double bond and a therapeutic agent that is attached (coupled) to the oligosaccharide (also referred to as the oligosaccharide head group) of the ganglioside (glyco-ceramide). The short-chain fatty acid of the ceramide can contain no double bonds between carbon atoms or can comprise a (one, at least one, one or more) cis double bond. The cis double bond may be present between any two consecutive carbon atoms; its presence causes the hydrocarbon chain of the fatty acid to bend, resulting in a "kink" in the fatty acid and a conformation that results in intracellular trafficking as described herein. In some embodiments, the cis double bond is present between carbon atoms 8 and 9. In other embodiments, in the short chain fatty acid, the cis double bond is present between two other consecutive carbon atoms (e.g., 1 and 2; 2 and 3; 3 and 4; 4 and 5; 5 and 6; 6 and 7; 7 and 8; 9 and 10; 10 and 11; or 11 and 12. In the long chain fatty acid, the cis double bond is present between two other consecutive carbon atoms (e.g., 1 and 2; 2 and 3; 3 and 4; 4 and 5; 5 and 6; 6 and 7; 7 and 8; 9 and 10; 10 and 11; 11 and 12; 12 and 13; 13 and 14; 14 and 15; 15 and 16; 16 and 17; 17 and 18; 18 and 19; 19 and 20; 20 and 21; 21 and 22; 23 and 24; 24 and 25; 25 and 26; 26 and 27 or 27 and 28). In all instances, the short chain or long chain fatty acid can contain more than one double bond.

The therapeutic agent may be attached to the oligosaccharide of the ceramide by any physiochemical means, including, but not limited to, hydrophobic interaction, covalent interaction, hydrogen bond interaction, or ionic interactions. The nature of the preferred bonding will depend, among other things, upon the mode of administration and the pharmaceutical carriers used to deliver the complex to the desired target site. "Linker groups" may be designed to facilitate the attachment of therapeutic agent to the oligosaccharide of the ceramide, or to facilitate, influence, modulate or regulate the release of the agent at the desired target site. A single therapeutic agent can be coupled to a single glycosphingolipid molecule, or it may be attached (coupled)

to more than one glycosphingolipid molecules. "Therapeutic agent" refers to eukaryotic and procaryotic cells, viruses, vectors, proteins, peptides, nucleic acids, polysaccharides and carbohydrates, lipids, glycoproteins, and combinations thereof, and synthetic organic and inorganic drugs exerting a biological effect when administered to an individual.

Isoforms of GM1 containing the fluorophore ALEXA 568-coupled to the GM1 oligosaccharide head-group and with the following fatty acids in the ceramide domain: C12:0, C16:0, C16:1 C18/20:0 are synthesized (FIG. 1). The ALEXA labeled gangliosides are introduced into human epithelial A431 cells expressing eGFP-proteins localized to specific intracellular compartments and the trafficking of the ganglioside is followed in live cells by confocal microscopy in 5-dimensions (3-D space, time, and color). GM1 with short chain C12:0 and "kinked chain" C16:1 ceramides localized to the recycling endosome, plasma membrane, and trans Golgi network (TGN) (FIGS. 2A, 2B, 3, 4A, 4B, and 12-14). The fully saturated long chain C18 and C16:0 gangliosides localized to the late endosome/lysosome (FIGS. 2A, 2B, 3, 4A, 4B, and 12-14, C20 not shown). Thus, the "kinked" or short chain shape of the lipid allows for movement across the sharp bends and curves of sorting tubules and vesicles so as to allow the lipid to escape the degradative late endosome pathway and enter other trafficking pathways (Maxfield and McGraw, 2004; Mukherjee et al., 1999), including the recycling endosome and TGN; and possibly the transcytotic route via the apical recycling endosome (ARE, Lencer and Tzaban, unpublished data, FIG. 28).

The significance of the instant invention is particularly evident for therapeutic drug development. It addresses two major problems in the field: macromolecular transport across mucosal barriers and drug half-life. Most protein therapeutics cannot be absorbed across mucosal surfaces (such as the intestine), rendering them clinically ineffective by oral administration and restricted to parenteral forms of drug delivery. This technology overcomes these problems. The technology also offers a way to target therapeutic molecules to mucosal surfaces by local (topical) administration so as to treat mucosal diseases, such as inflammatory bowel disease, without systemic toxicities. The ceramide chain fused to recombinant IL-10 or adenosine are examples of therapeutics to calm inflammatory diseases with predicted efficacy when applied to mucosal surfaces by topical or oral administration. Another application is to fuse the ceramide to a clotting factor or factors, such as factor VIII and/or factor IX so as to prolong its half-life when it is administered parenterally, such as for treatment for hemophilia. The composition and methods described herein can also be used as a delivery vehicle for novel or re-engineered mucosal vaccines. The technology represents a platform for drug delivery with many other potential applications, including the re-design of small molecule and protein therapeutics already in use clinically (e.g., antibodies against TNF-α or the interferons; clotrimazole, vasoactive intestinal peptide (VIP) and other ligands for G-protein coupled receptors linked to activation of cAMP, EGF-receptor ligands.

Inducing Mucosal Immunity by Creating a Novel Platform to Transport Vaccine Antigens and Adjuvants Across Epithelial Barriers Mucosal vaccination can be reinforced by harnessing the intracellular machinery that delivers molecules across the epithelial barrier lining mucosal surfaces in order to stimulate cells of the adaptive immune system. The technology represents a novel platform comprised of specific ceramide-based lipids that will act as molecular carriers capable of delivering a wide range of vaccine antigens and Toll-like receptor (TLR) ligands (as adjuvants) across epithelial barriers to induce mucosal immunization. The technology can be used to deliver protein or peptide antigens for mucosal vaccination and TLR-agonists as adjuvants. Ova as a model antigen, or the SIINFEKL MHC Class I ova peptide, can be used for fusion to the relevant ceramide lipids. In this system, testing for utility in mucosal delivery is enhanced by using mice already sensitized to OVA or adoptively transplanted with T cells expressing receptors for the SIINFEKL peptide.

Mucosal surfaces represent vast areas where host tissues are separated from the environment solely by a delicate but highly effective single layer of columnar epithelial cells. Under the epithelium, the connective tissue is patrolled by antigen-presenting cells and armed with effector and memory lymphocytes responsible for local mucosal protection and rapid-recall responses to pathogen challenge.

Protective mucosal immunity is best induced by direct mucosal delivery of vaccine antigens. In recent years there has been an explosion of interest in enhancing uptake of vaccine antigens across the intestinal epithelial barrier via the specialized M cells that lie over organized mucosal lymphoid tissues (such as Peyer's patches); this is where many initial inductive events that lead to mucosal immune responses are thought to occur. However, the technology focuses on a different and potentially more efficient and effective method to induce immunity—through actions directed at absorptive enterocytes, which cover the vast majority of the mucosal surface. Enterocytes are also capable of antigen transport. These cells play complex roles in both innate and adaptive immunity, providing a constant stream of information to subepithelial cells to optimize mucosal immune protection (Shang 2008). Importantly, epithelial cells express Toll-like receptors (TLRs) that recognize common molecular components unique to microorganisms; they respond to luminal microbes and microbe products by releasing cytokine and chemokine signals that trigger innate, nonspecific defenses and promote adaptive immune responses and tolerance inhibition (Backhed 2005; Rakoff-Nahoum 2008).

To prevent unwanted reactions against luminal microbes and other potential antigens, however, the epithelial barrier is organized so as to restrict access to the TLRs and cells of the adaptive immune system; these cells are located on the opposite, basolateral side of the epithelial barrier. Thus, if the transport of vaccine antigens together with TLR ligands (as adjuvants) across epithelial barriers can be enhanced, protective mucosal immune responses could be greatly amplifed. A novel approach for accomplishing this goal is to adapt the strategy used by cholera toxin as it invades intestinal epithelial cells to cause the massive diarrhea seen in cholera. Cholera toxin is probably the most effective adjuvant for mucosal vaccination and the most frequently used in experimental mucosal vaccine models. GM1 is the vehicle that carries the toxin into and across the intestinal barrier epithelium. GM1-ceramides containing "short chain" C12:0 or "kinked chain" unsaturated C16:1 fatty acids enter the recycling endosome, a compartment where membranes are "sorted" into other pathways, including for transport across the cell to the basolateral membrane by transcytosis (absorption). Short or "kinked chain" ceramides completely avoid transport into the lysosome, the degradative compartment. In contrast, the GM1-ceramides with long, fully saturated fatty acid chains (C18:0 or C16:0) are only transported into the lysosome. Thus, ceramides of specific structure may be used to direct vaccine antigens and TLR-based adjuvants into the transcytotic (absorptive) pathway and thereby avoid lysosomal transport. Specific ceramides may be enlisted to deliver these molecules across mucosal barriers to enhance adaptive immunity. The approach targets the vast numbers of epithelial cells lining the majority of the intestine and airway—not just M cells, the primary focus for vaccine delivery so far. The technology can be applied to prevent diarrheal diseases, TB, HIV, respiratory illness, and many other diseases that claim the lives of millions of children.

Accordingly, the instant invention encompasses the targeted delivery of the following classes of biologically active compounds:

Antineoplastic Compounds. Nitrosoureas, e.g., carmustine, lomustine, semustine, strepzotocin; Methylhydrazines, e.g., procarbazine, dacarbazine; steroid hormones, e.g., glucocorticoids, estrogens, progestins, androgens, tetrahydrodesoxycaricosterone, cytokines and growth factors; Asparaginase.

Immunoactive Compounds. Immunosuppressives, e.g., pyrimethamine, trimethopterin, penicillamine, cyclosporine, azathioprine; immunostimulants, e.g., levamisole, diethyl dithiocarbamate, enkephalins, endorphins.

Antimicrobial Compounds. Antibiotics, e.g., beta lactam, penicillin, cephalosporins, carbapenims and monobactams, beta-lactamase inhibitors, aminoglycosides, macrolides, tetracyclins, spectinomycin; Antimalarials, Amebicides, Antiprotazoal, Antifungals, e.g., amphotericin beta, Antiviral, e.g., acyclovir, idoxuridine, ribavirin, trifluridine, vidarbine, gancyclovir.

Parasiticides, Antihalmintics, Radiopharmaceutics, gastrointestinal drugs.

Hematologic Compounds. Immunoglobulins; blood clotting proteins; e.g., lintihemophilic factor, factor IX complex; anticoagulants, e.g., dicumarol, heparin Na; fibrolysin inhibitors, tranexamic acid.

Cardiovascular Drugs. Peripheral antiadrenergic drugs, centrally acting antihypertensive drugs, e.g., methyldopa, methyldopa HCl; antihypertensive direct vasodilators, e.g., diazoxide, hydralazine HCl; drugs affecting renin-angiotensin system; peripheral vasodilators, phentolamine; antianginal drugs; cardiac glycosides; inodilators; e.g., amrinone, milrinone, enoximone, fenoximone, imazodan, sulmazole; antidysrhythmic; calcium entry blockers; drugs affecting blood lipids; ranitidine, bosentan, rezulin.

Respiratory Drugs. Sypathomimetic drugs: albuterol, bitolterol mesylate, dobutamine HCl, dopamine HCl, ephedrine SO, epinephrine, fenfluramine HCl, isoproterenol HCl, methoxamine HCl, norepinephrine bitartrate, phenylephrine HCl, ritodrine HCl; cholinomimetic drugs, e.g., acetylcholine Cl; anticholinesterases, e.g., edrophonium Cl; cholinesterase reactivators; adrenergic blocking drugs, e.g., acebutolol HCl, atenolol, esmolol HCl, labetalol HCl, metoprolol, nadolol, phentolamine mesylate, propanolol HCl; antimuscarinic drugs, e.g., anisotropine methylbromide, atropine SO4, clinidium Br, glycopyrrolate, ipratropium Br, scopolamine HBr.

Neuromuscular Blocking Drugs. Depolarizing, e.g., atracurium besylate, hexafluorenium Br, metocurine iodide, succinylcholine Cl, tubocurarine Cl, vecuronium Br; centrally acting muscle relaxants, e.g., baclofen.

Neurotransmitters and neurotransmitter Agents. Acetylcholine, adenosine, adenosine triphosphate, amino acid neurotransmitters, e.g., excitatory amino acids, GABA, glycine; biogenic amine neurotransmitters, e.g., dopamine, epinephrine, histamine, norepinephrine, octopamine, serotonin, tyramine; neuropeptides, nitric oxide, K+ channel toxins, Antiparkinson Drugs. amaltidine HCl, benztropine mesylate, e.g., carbidopa.

Diuretic Drugs. Dichlorphenamide, methazolamide, bendroflumethiazide, polythiazide.

Uterine, Antimigraine Drugs. Carboprost tromethamine, mesylate, methysergide maleate.

Hormones. Pituitary hormones, e.g., chorionic gonadotropin, cosyntropin, menotropins, somatotropin, iorticotropin, protirelin, thyrotropin, vasopressin, lypressin; adrenal hormones, e.g., beclomethasone dipropionate, betamethasone, dexamethasone, triamcinolone; pancreatic hormones, e.g., glucagon, insulin; parathyroid hormone, e.g., dihydrochysterol; thyroid hormones, e.g., calcitonin etidronate disodium, levothyroxine Na, liothyronine Na, liotrix, thyroglobulin, teriparatide acetate; antithyroid drugs; estrogenic hormones; progestins and antagonists, hormonal contraceptives, testicular hormones; gastrointestinal hormones: cholecystokinin, enteroglycan, galanin, gastric inhibitory polypeptide, epidermal growth factor-urogastrone, gastric inhibitory polypeptide, gastrin-releasing peptide, gastrins, pentagastrin, tetragastrin, motilin, peptide YY, secretin, vasoactive intestinal peptide, sincalide.

Enzymes. Hyaluronidase, streptokinase, tissue plasminogen activator, urokinase, PGE-adenosine deaminase.

Intravenous Anesthetics. Droperidol, etomidate, fetanyl citrate/droperidol, hexobarbital, ketamine HCl, methohexital Na, thiamylal Na, thiopental Na.

Antiepileptics. Carbamazepine, clonazepam, divalproex Na, ethosuximide, mephenytoin, paramethadione, phenytoin, primidone.

Peptides and proteins. The glycosphingolipids may be attached to peptides or polypeptides, e.g., ankyrins, arrestins, bacterial membrane proteins, clathrin, connexins, dystrophin, endothelin receptor, spectrin, selectin, cytokines; chemokines; growth factors, insulin, erythropoietin (EPO), tumor necrosis factor (TNF), neuropeptides, neuropeptide Y, neurotensin, transforming growth factor .alpha., transforming growth factor .beta., interferon (IFN), and hormones, growth inhibitors, e.g., genistein, steroids etc; glycoproteins, e.g., ABC transporters, platelet glycoproteins, GPIb-IX complex, GPIIb-IIIa complex, vitronectin, thrombomodulin, CD4, CD55, CD58, CD59, CD44, lymphocye function-associated antigen, intercellular adhesion molecule, vascular cell adhesion molecule, Thy-1, antiporters, CA-15-3 antigen, fibronectins, laminin, myelin-associated glycoprotein, GAP, GAP-43.

Figure 11:
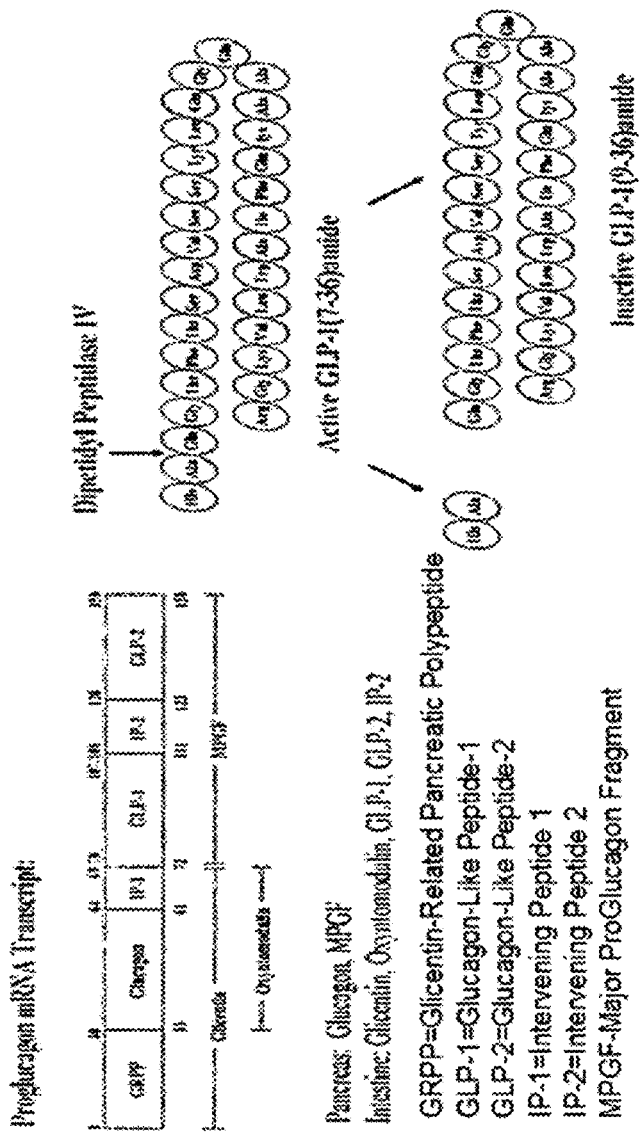
FIG. 11: GLP1 is derived from proglucagon by post-translational cleavage to the active peptide.
Figure 12:
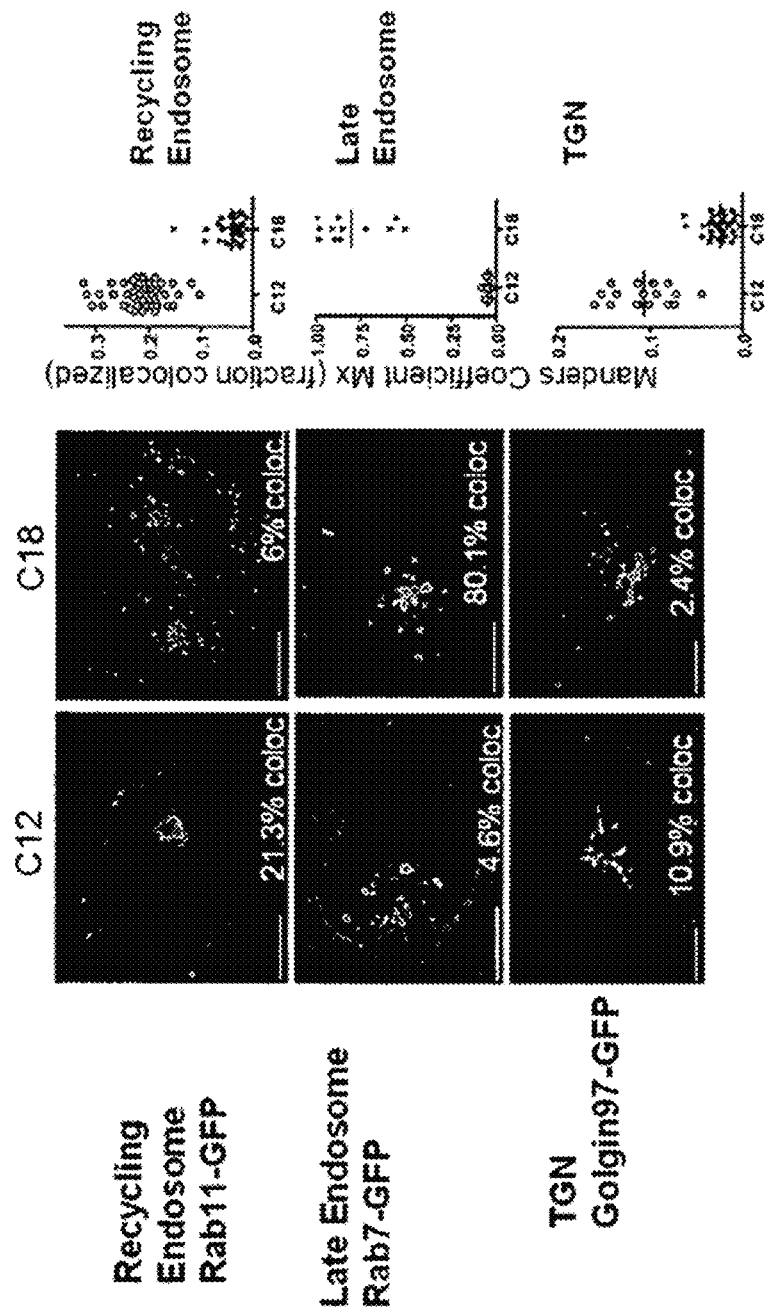
FIG. 12 shows live cells incubated with the short chain C12:0 ganglioside (left panel) and with long chain GM1 (right panel). The cells are stably expressing EGFP-labeled Rab11a, Rab7, and Golgin97 to mark the recycling endosome, the late endosome, and the trans Golgi (TGN). Short chain ceramides co-localize with the recycling endosome, PM, and trans Golgi—but the long chain ceramides localize with the late endosome. The morphologic data are quantified in the histograms on the right and in the lower right hand section of each panel.
Figure 12:
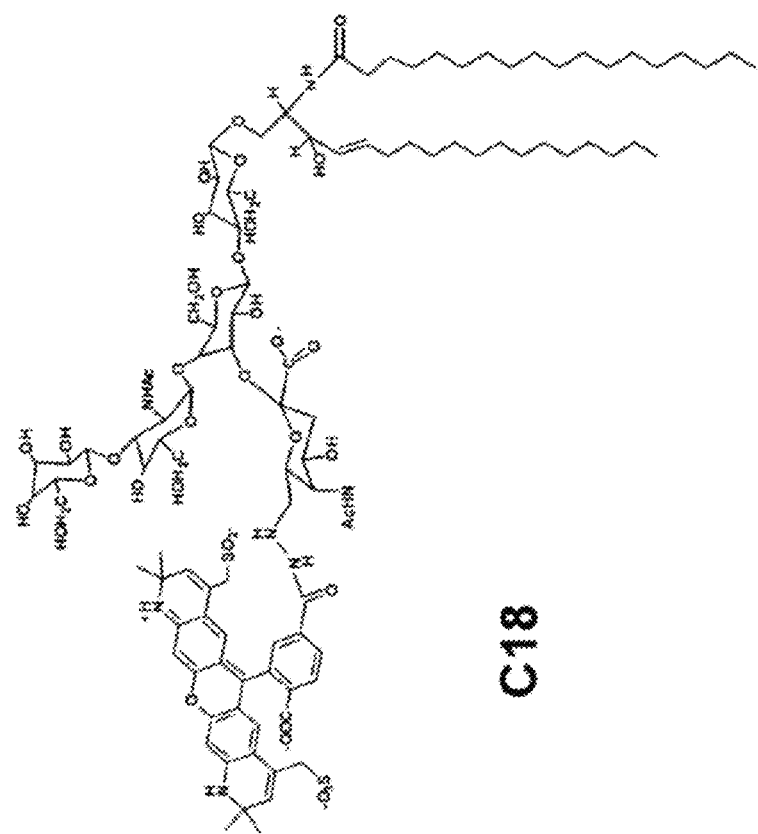
Figure 12:
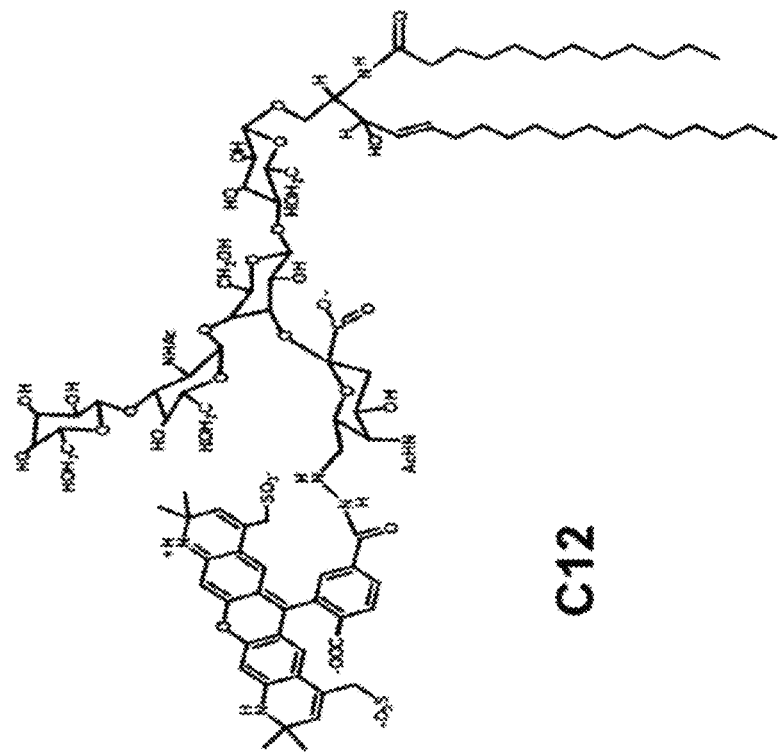
Figure 13:
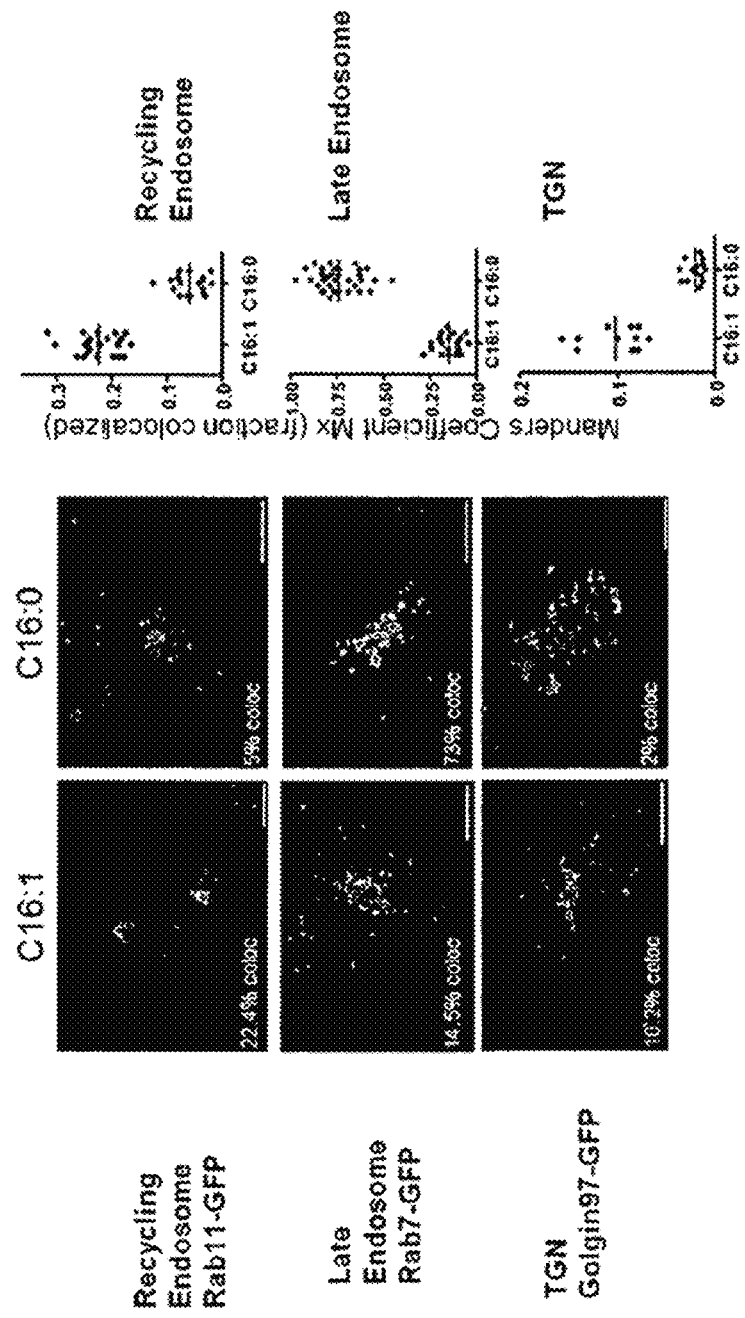
FIG. 13 shows that the unsaturated chain (C16:1) occupies the RE and the TGN avoiding the late endosome, while the saturated chain GM1 (C16:0) sorts predominantly into the late endosome. The tipping point is the presence of a double bond in the fatty acid of the ceramide chain.
Figure 13:
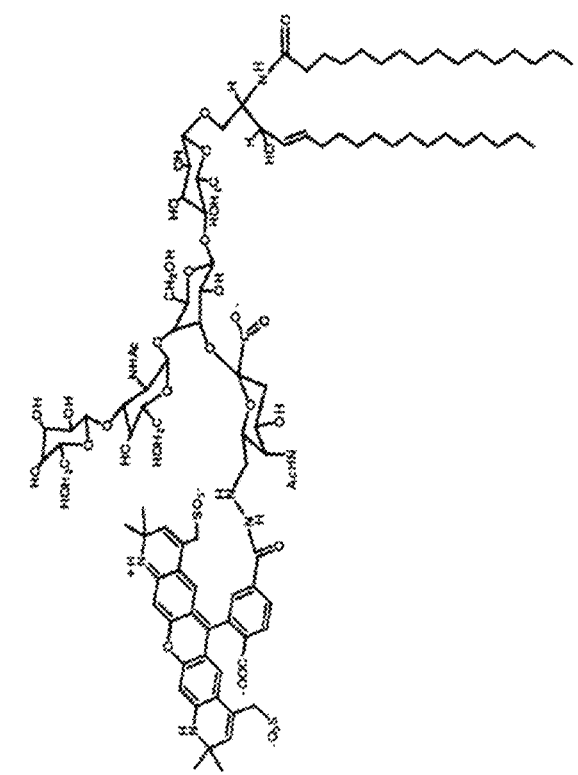
Figure 13:
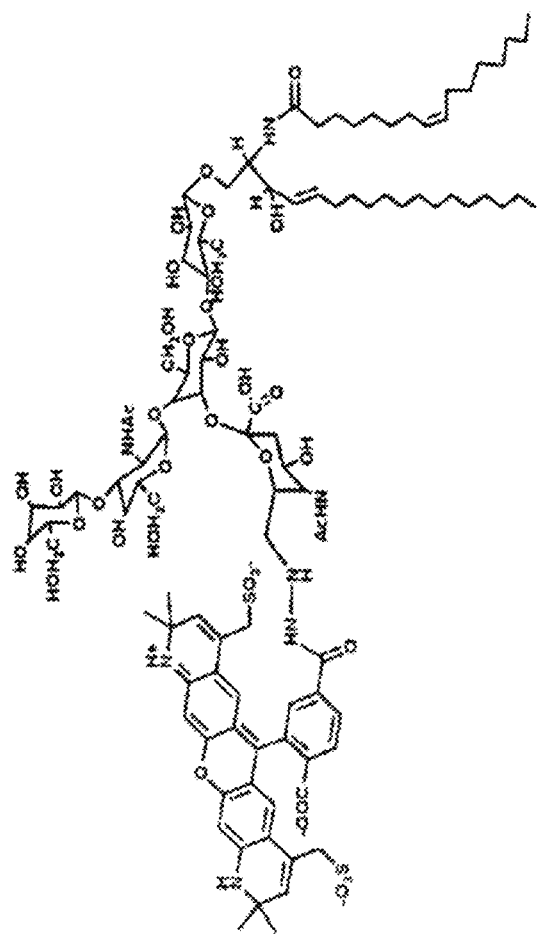
Figure 14:
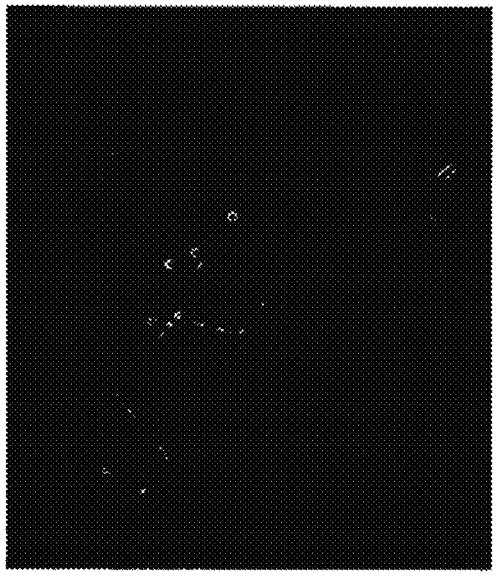
FIG. 14 shows that when applied together, the two ceramides (C12:0 and C18:0) are sorted differentially almost completely away from each other. Neither ceramide induces toxicity.
Figure 14:
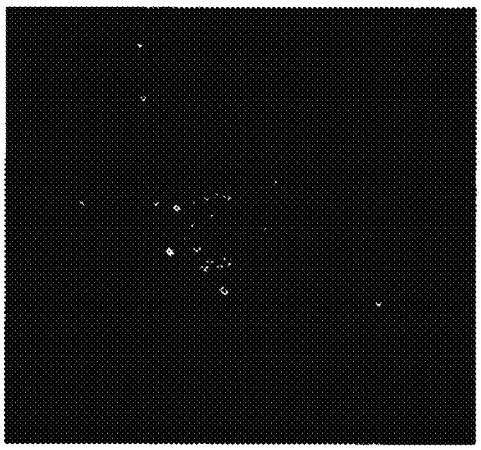
Figure 14:
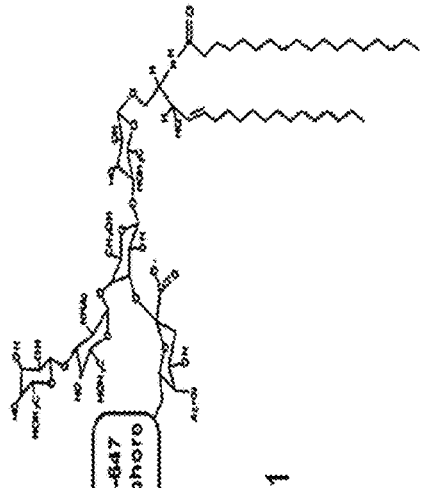
Figure 14:
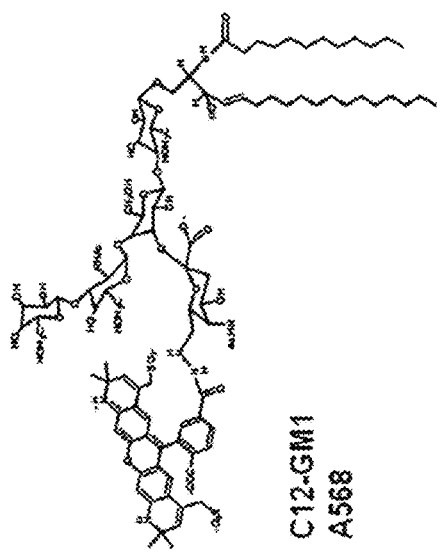

In some embodiments, the instant invention encompasses the targeted delivery of the peptide hormone GLP1. Human GLP1 is derived from the protein product known as proglucagon. The translated product of the proglucagon mRNA transcript is differentially processed in pancreatic or intestinal L-cclls (Panel A) (Kieffer and Habener, 1999). In intestinal cells, the gut specific prohormone convertase enzymes 1 and 3 produce two forms of GLP1 and both are secreted: GLP1(7-37) and GLP1(7-36)amide (FIG. 11). Both molecules are equally potent in vivo (Orskov et al., 1993). The majority of circulating active GLP1, however, is GLP1(7-36)amide. GLP1(7-36)amide denotes that the carboxylic acid of Arg at position 36 has been amidated while GLP1(7-37) contains a C-terminal Gly residue. The amidation is critical to preserve the half-life of the circulating peptide containing a penultimate C-terminal Arg residue. Bioactivity of the native peptides in vivo is terminated by dipeptidyl peptidase IV, which removes the N-terminal dipeptide His-Ala (Panel B above) (Sturm et al., 1998). Because the pro-hormone already contains post-translational cleavage sites at both N- and C-termini, these features can be utilized in a novel way to design "native" reversible linkages to the carrier lipid that will release the native peptides, GLP1(7-37) or GLP1(7-36)amide, upon absorption into or across the intestine.

Human GLP1 is a cleavage product of proglucagon produced in pancreatic or intestinal L-cells (Kieffer and Habener, 1999). Once in the circulation, GLP-1 has a half-life of less than 2 minutes, due to rapid degradation by the enzyme dipeptidyl peptidase-4. GLP-1 possesses several physiological properties that make it a potential treatment for diabetes mellitus, especially type II. The known physiological functions of GLP-1 include its ability to increase insulin secretion from the pancreas in a glucose-dependent manner; decrease glucagon secretion from the pancreas; and increase beta cells mass and insulin gene expression. GLP-1 is an attractive candidate for this study because of interest in its use as a therapeutic peptide, its short half-life, and the ease of bioassay for GLP-1 activity (serum glucose).

Certain aspects of the structure of GLP-1 and its biogenesis from proglucagon allow for the design of cleavage sites in the proposed fusion molecules for release of the native peptide from the GM1 lipid after or during absorption.

Significance: Normally, mucosal surfaces are impermeant to large molecules the size of GLP1. So far, this problem has prevented the application of therapeutic molecules for oral or pulmonary drug delivery or for mucosal vaccination. The technology presents a novel and simple approach to render a protein, peptide, or small molecule as substrate for transport through endogenous transcellular absorptive pathways that cross mucosal barriers (intestine, lung, oral mucosa, GU tract). This is predicted to lead to topical or systemic drug/antigen delivery, or both; and for enhancement of drug half-life by trafficking away from the degradative lysosome compartments.

The need for such non-parenteral routes of administration for therapeutic proteins and vaccine antigens is great. Especially for mucosal vaccines, such a route of absorption across epithelial barriers is predicted to enhance immunizations against oral and respiratory pathogens that invade via mucosal surfaces.

Also, the technology allows for topical delivery of potent anti-inflammatory agents that have significant toxicity when they are delivered systemically. A good example where such an application would have great utility is inflammatory bowel disease.

Cytokines and Cytokine Receptors. Examples of cytokines and receptors thereof which may be delivered by coupling to a glycosphingolipid with defined ceramide structure in accordance with the present invention, include, but are not limited to: Interleukin-1 (IL-1), IL-2, IL-3, IL-4, IL-5, IL-6, IL-7, IL-8, IL-9, IL-10, IL-11, IL-12, IL-13, IL-14, IL-15, IL-16, IL-17, IL-18, IL-1 receptor, IL-2 receptor, IL-3 receptor, IL-4 receptor, IL-5 receptor, IL-6 receptor, IL-7 receptor, IL-8 receptor, IL-9 receptor, IL-10 receptor, IL-11 receptor, IL-12 receptor, IL-13 receptor, IL-14 receptor, IL-15 receptor, IL-16 receptor, IL-17 receptor, IL-18 receptor, lymphokine inhibitory factor, macrophage colony stimulating factor, platelet derived growth factor, stem cell factor, tumor growth factor .beta., tumor necrosis factor, lymphotoxin, Fas, granulocyte colony stimulating factor, granulocyte macrophage colony stimulating factor, interferon .alpha., interferon .beta., interferon .gamma.

Growth Factors and Protein Hormones. Examples of growth factors and receptors thereof and protein hormones and receptors thereof which may be delivered by coupling to a glycosphingolipid with defined ceramide structure in accordance with the present invention, include, but are not limited to: erythropoietin, angiogenin, hepatocyte growth factor, fibroblast growth factor, keratinocyte growth factor, nerve growth factor, tumor growth factor .alpha., thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II.

Chemokines. Examples of chemokines and receptors thereof which may be delivered by coupling to a glycosphingolipid with defined ceramide structure in accordance with the present invention, include, but are not limited to: ENA-78, ELC, GRO-alpha, GRO-beta, GRO-gamma, HRG, LIF, IP-10, MCP-1, MCP-2, MCP-3, MCP-4, MIP-1 alpha, MIP-1 beta, MIG, MDC, NT-3, NT-4, SCF, LIF, leptin, RANTES, lymphotactin, eotaxin-1, eotaxin-2, TARC, TECK, WAP-1, WAP-2, GCP-1, GCP-2, alpha-chemokine receptors: CXCR1, CXCR2, CXCR3, CXCR4, CXCR5, CXCR6, CXCR7 beta-chemokine receptors: CCR1, CCR2, CCR3, CCR4, CCR5, CCR6, CCR7.

Chemotherapeutics. The glycosphingolipid with defined ceramide structure may also be conjugated to chemotherapy or anti-tumor agents that are effective against various types of human cancers (including leukemia, lymphomas, carcinomas, sarcomas, myelomas), such as, doxorubicin, mitomycin, cisplatin, daunorubicin, bleomycin, actinomycin D, neocarzinostatin.

Antibodies. The glycosphingolipid with defined ceramide structure of the present invention may be conjugated to antibodies including, but not limited to: (a) anti-cluster of differentiation antigen CD-1 through CD-166 and the ligands or counter receptors for these molecules; (b) anti-cytokine antibodies, e.g., anti-IL-1 through anti-IL-18 and the receptors for these molecules; (c) anti-immune receptor antibodies, antibodies against T cell receptors, major histocompatibility complexes I and II, B cell receptors, selectin killer inhibitory receptors, killer activating receptors, OX-40, MadCAM-1, Gly-CAM1, integrins, cadherens, sialoadherens, Fas, CTLA-4, Fc gamma-receptors, Fc alpha-receptors, Fc epsilon-receptors, Fc mu-receptors, and their ligands; (d) anti-metalloproteinase antibodies, e.g., collagenase, MMP-1 through MMP-8, TIMP-1, TIMP-2; anti-cell lysis/proinflammatory molecules, e.g., perforin, complement components, prostanoids, nitron oxide, thromboxanes; and (e) anti-adhesion molecules, e.g., carcioembryonic antigens, lamins, fibronectins.

Antiviral Agents. The glycosphingolipid with defined ceramide structure may be conjugated to antiviral agents such as reverse transcriptase inhibitors and nucleoside analogs, e.g. ddI, ddC, 3TC, ddA, AZT; protease inhibitors, e.g., Invirase, ABT-538; inhibitors of in RNA processing, e.g., ribavirin.

Specific examples of known therapeutics which may be delivered by coupling to a glycosphingolipid with defined ceramide structure include, but are not limited to:

(a) Capoten, Monopril, Pravachol, Avapro, Plavix, Cefzil, Duricef/Ultracef, Azactam, Videx, Zerit, Maxipime, VePesid, Paraplatin, Platinol, Taxol, UFT, Buspar, Serzone, Stadol NS, Estrace, Glucophage (Bristol-Myers Squibb);

(b) Ceclor, Lorabid, Dynabac, Prozac, Darvon, Permax, Zyprexa, Humalog, Axid, Gemzar, Evista (Eli Lily);

(c) Vasotec/Vaseretic, Mevacor, Zocor, Prinivil/Prinizide, Plendil, Cozaar/Hyzaar, Pepcid, Prilosec, Primaxin, Noroxin, Recombivax HB, Varivax, Timoptic/XE, Trusopt, Proscar, Fosamax, Sinemet, Crixivan, Propecia, Vioxx, Singulair, Maxalt, Ivermectin (Merck & Co.);

(d) Diflucan, Unasyn, Sulperazon, Zithromax, Trovan, Procardia XL, Cardura, Norvasc, Dofetilide, Feldene, Zoloft, Zeldox, Glucotrol XL, Zyrtec, Eletriptan, Viagra, Droloxifene, Aricept, Lipitor (Pfizer);

(e) Vantin, Rescriptor, Vistide, Genotropin, Micronase/Glyn./Glyb., Fragmin, Total Medrol, Xanax/alprazolam, Sermion, Halcion/triazolam, Freedox, Dostinex, Edronax, Mirapex, Pharmorubicin, Adriamycin, Camptosar, Remisar, Depo-Provera, Caverject, Detrusitol, Estring, Healon, Xalatan, Rogaine (Pharmacia & Upjohn);

(f) Lopid, Accrupil, Dilantin, Cognex, Neurontin, Loestrin, Dilzem, Fempatch, Estrostep, Rezulin, Lipitor, Omnicef, FemHRT, Suramin, Clinafloxacin (Warner Lambert).

(g) Rotavirus VP6 and VP7 capsid proteins: These refer to the art-recognized major viral proteins of the inner and outer capsid from any species or strain within the genus Rotavirus. Examples of rotavirus strains from which the VP6 protein and the VP7 protein can be isolated and employed in the present invention include, but are not limited to, Simian SA-11, human D rotavirus, bovine UK rotavirus, human Wa or W rotavirus, human DS-1 rotavirus, rhesus rotavirus, the "0" agent, bovine NCDV rotavirus, human K8 rotavirus, human KU rotavirus, human DB rotavirus, human S2 rotavirus, human KUN rotavirus, human 390 rotavirus, human P rotavirus, human M rotavirus, human Walk 57/14 rotavirus, human Mo rotavirus, human Ito rotavirus, human Nemoto rotavirus, human YO rotavirus, human McM2 rotavirus, rhesus monkey MMU18006 rotavirus, canine CU-1 rotavirus, feline Taka rotavirus, equine H-2 rotavirus, human St. Thomas No. 3 and No. 4 rotaviruses, human Hosokawa rotavirus, human Hochi rotavirus, porcine SB-2 rotavirus, porcine Gottfried rotavirus, porcine SB-1A rotavirus, porcine OSU rotavirus, equine H-1 rotavirus, chicken Ch.2 rotavirus, turkey Ty.1 rotavirus, and bovine C486 rotavirus. Thus, the present invention encompasses the use of VP6 and VP7 from any rotavirus strain, whether from subgroup I, subgroup II, or any as yet unidentified subgroup, as well as from any of the serotypes 1-7, as well as any as yet unidentified serotypes.

(h) Clotrimazole (i) TLR-based adjuvants (including flagellin, polysaccharides, ssRNA, dsRNA) Further examples of therapeutic agents which may be delivered by the glycosphingolipid-therapeutic agent complex of the present invention may be found in: Goodman and Gilman's The Pharmacological Basis of Therapeutics. 9th ed. McGraw-Hill 1996, incorporated herein by reference in its entirety.

The compositions of matter and methods described herein can be used in many contexts and an individual in whom they can be used is, for example, a human or vertebrate animal, such as a dog, cat, horse, cow, pig, sheep, goat, chicken, monkey, rat or mouse. The ganglioside-therapeutic agent complexes may be administered to an individual who has, has had or is susceptible to developing one or more conditions/diseases that require or would benefit from treatment. For example, the compositions described herein may be used to treat, prevent or ameliorate immune system deficiencies, infectious diseases (viral, fungal, bacterial or parasitic), autoimmune diseases, blood disorders, cancers, metabolic disorders, allergies, inflammatory bowel disease and skin disorders. In addition, gangliosides attached to antigen can be administered to stimulate an individual's response to a vaccine. The antigen is selected from the group consisting of: an antigen that is characteristic of a pathogen, an antigen that is characteristic of an autoimmune disease, an antigen that is characteristic of an allergen and an antigen that is characteristic of a tumor.

Immune system deficiencies include any disease or disorder in which an individual's immune system is not functioning normally or in which it would be useful to boost the individual's immune response, for example to eliminate a tumor or cancer (e.g. tumors of the brain, lung (e.g. small cell and non-small cell), ovary, breast, prostate, colon, as well as other carcinomas and sarcomas) or an infection in an individual.

Examples of infectious virus include: Retroviridae e.g., human immunodeficiency viruses, such as HIV-1 (also referred to as HTLV-III, LAV or HTLV-III/LAV, or HIV-III) and other isolates, such as HIV-LP; Picornaviridae (e.g., polio viruses, hepatitis A virus; enteroviruses, human coxsackie viruses, rhinoviruses, echoviruses); Calciviridae (e.g., strains that cause gastroenteritis); Togaviridae (e.g., equine encephalitis viruses, rubella viruses); Flaviridac (e.g., dengue viruses, encephalitis viruses, yellow fever viruses); Coronaviridae (e.g., coronaviruses); Rhabdoviridae (e.g., vesicular stomatitis viruses, rabies viruses); Filoviridae (e.g., ehola viruses); Paramyxoviridae (e.g., parainfluenza viruses, mumps virus, measles virus, respiratory syncytial virus); Orthomyxoviridae (e.g., influenza viruses); Bungaviridae (e.g., Hantaan viruses, bunga viruses, phleboviruses and Nairo viruses); Arena viridae (hemorrhagic fever viruses); Reoviridae (e.g., reoviruses, orbiviruses and rotaviruses); Birnaviridae; Hepadnaviridae (Hepatitis B virus); Parvoviridae (parvoviruses); Papovaviridae (papilloma viruses, polyoma viruses); Adenoviridae (most adenoviruses); Herpesviridae (herpes simplex virus (HSV) 1 and 2, varicella zoster virus, cytomegalovirus (CMV), herpes viruses); Poxviridae (variola viruses, vaccinia viruses, pox viruses); and Iridoviridae (e.g., African swine fever virus); and unclassified viruses (e.g., the etiological agents of Spongiform encephalopathies, the agent of delta hepatitis (thought to be a defective satellite of hepatitis B virus), the agents of non-A, non-B hepatitis (class 1=internally transmitted; class 2=parenterally transmitted (i.e., Hepatitis C); Norwalk and related viruses, and astroviruses).

Examples of infectious bacteria include: *Helicobacter pyloris, Borelia burgdorferi, Legionella pneumophilia, Mycobacteria* spp. (e.g., *M. tuberculosis, M. avium, M. intracellulare, M. kansasii, M. gordonae*), *Staphylococcus aureus, Neisseria gonorrhoeae, Neisseria meningitidis, Listeria monocytogenes, Streptococcus pyogenes* (Group A *Streptococcus*), *Streptococcus agalactiae* (Group B *Streptococcus*), *Streptococcus* (*viridans* group), *Streptococcus faecalis, Streptococcus Bovis, Streptococcus* (anaerobic spp.), *Streptococcus pneumoniae*, pathogenic *Campylobacter* sp., *Enterococcus* sp., *Haemophilus influenzae, Bacillus anthracis, Corynebacterium diphtheriae, Corynebacterium* sp., *Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira*, and *Actinomyces israelli*.

Examples of infectious fungi include: *Cryptococcus neoformans, Histoplasma capsulatum, Coccidioides immitis, Blastomyces dermatitidis, Chlamydia trachomatis, Candida albicans*. Other infectious organisms (i.e., protists) include: *Plasmodium falciparum* and *Toxoplasma gondii*.

Examples of autoimmune diseases include: Addison's disease, diabetes mellitus (type 1), Graves' disease, interstitial cystitis, lupus erythematous, multiple sclerosis and Hashimoto's thyroiditis. Allergic conditions include eczema, allergic rhinitis or coryza, hay fever, bronchial asthma, urticaria (hives) and food allergies, and other atopic conditions.

An "effective amount" of a ganglioside-therapeutic agent complex is the amount necessary or sufficient to have a desired effect in an individual. The effective amount will vary with the particular condition being treated, the age and physical condition of the individual being treated, the severity of the condition, the duration of the treatment, the nature of the concurrent therapy (if any), the specific route of administration and other factors within the knowledge and expertise of the health care practitioner. For example, an effective amount could be that amount necessary to prevent a tumor or cancer, or bacterial, viral or fungal infection or reduce (partially or totally) the extent to which they occur. This amount will vary from individual to individual and can be determined empirically using known methods by one of ordinary skill in the art.

The delivery vehicles and the ganglioside-therapeutic agent complexes may be administered by any route. Routes of administration include enteral routes, such as oral and any other means by which the gastrointestinal tract is involved, and parenteral routes, such as by injection (subcutaneous, intravenous, intramuscular injection) or infusion (typically by intravenous route). The injection can be in a bolus or a continuous infusion.

When administered, the delivery vehicle or ganglioside-therapeutic agent(s) are typically administered as pharmaceutical preparations applied in pharmaceutically-acceptable amounts and in a pharmaceutically-acceptably composition. Such preparations may contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

The ganglioside-therapeutic agent/moiety complexes may be combined, optionally, with a pharmaceutically-acceptable (compatible) carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the compositions of the present invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride, chlorobutanol, parabens and thimerosal.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

The present invention is further illustrated by the following Examples which in no way should be construed as further limiting. The entire contents of all of the references (including literature references, issued patents, published patent applications, and co-pending patent applications) cited throughout this application are hereby expressly incorporated by reference.

EXAMPLES

Example 1

The fluorescently-labeled GM1 isoforms were applied to apical membranes of polarized epithelial cells at a concentration of 1.6 µm in hank's buffered saline solution (HBSS) with 0.034% defatted bovine serum albium (BSA) at 10 c for 1 hour. After washing away unincorporated GM1 from the apical membrane with cold HBSS, the cells were incubated at 37° C. for 90 minutes and then imaged by spinning disk confocal microscopy. The data shows that only the C12 isoform loads the basolateral membranes. The C18 isoform does not label the basolateral membranes and goes to late endosomes only as shown by concentrated puncta in non-polarized cells. (FIGS. 6-10).

Example 2

Construction of ganglioside-peptide complex. Chemically couple a small "reporter" peptide GKSKG-YPYDVPDYA (HA-tag)-GKSGC (SEQ ID NO.: 8) to the oligosaccharide head group of ganglioside GM1 containing ceramides with C12:0, C16:1, or C18:0 fatty acids.

Figure 1A:
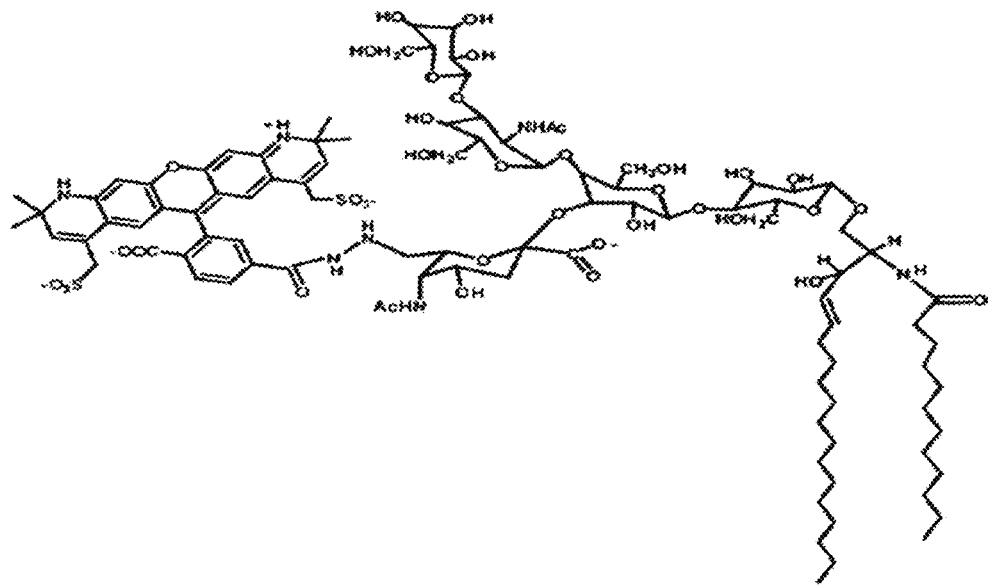
FIGS. 1A-1D depict GM1 isoforms containing the fluorophore ALEXA 568-coupled to the GM1 oligosaccharide head-group and with the following fatty acids in the ceramide domain.
Figure 1B:
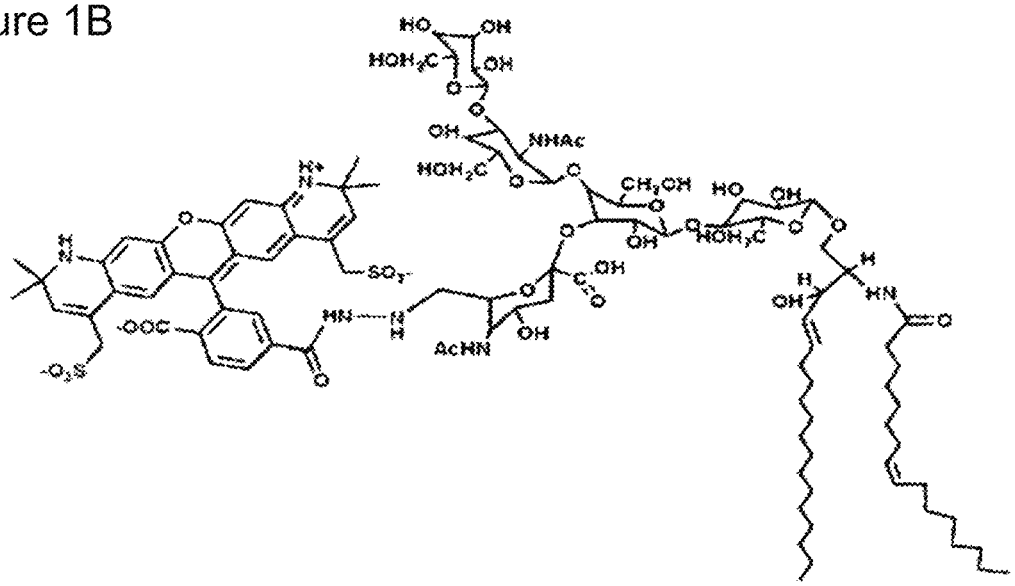
Figure 1C:
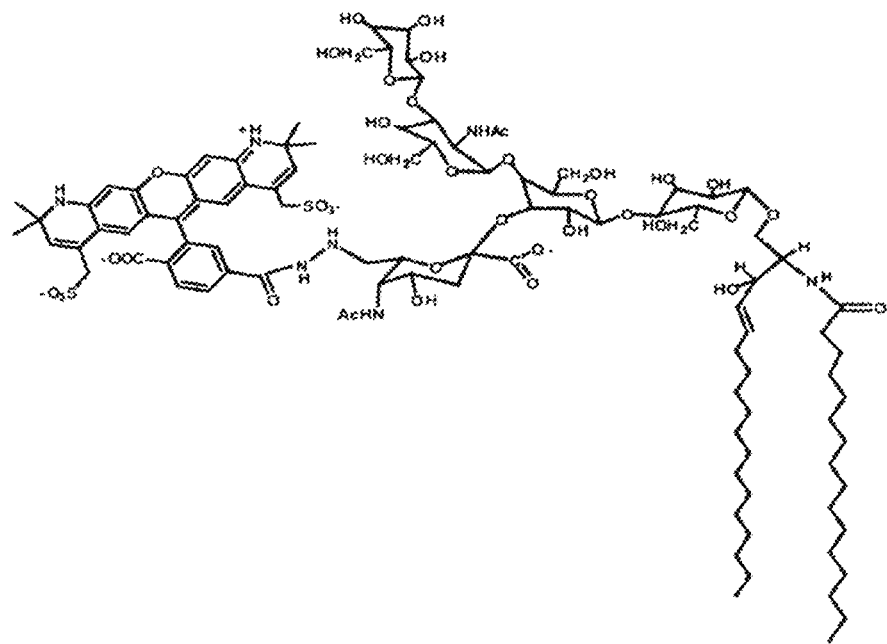
Figure 1D:
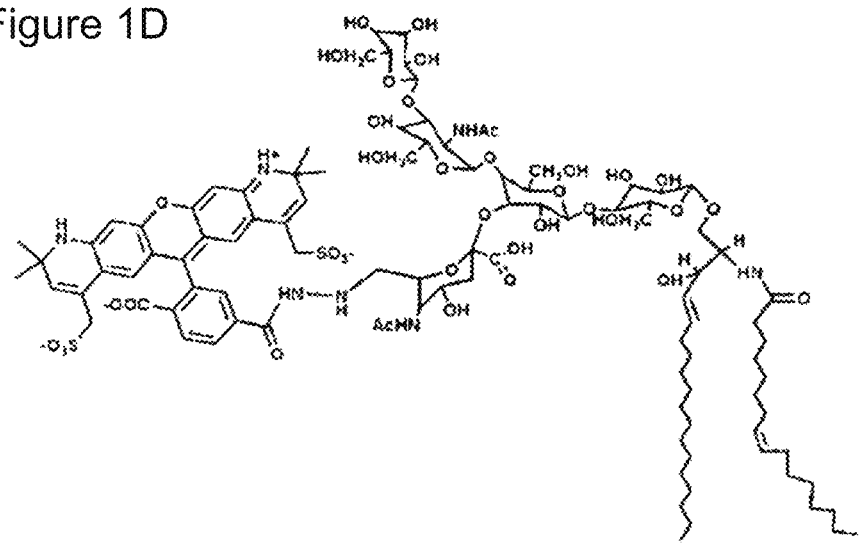
Figure 2A:
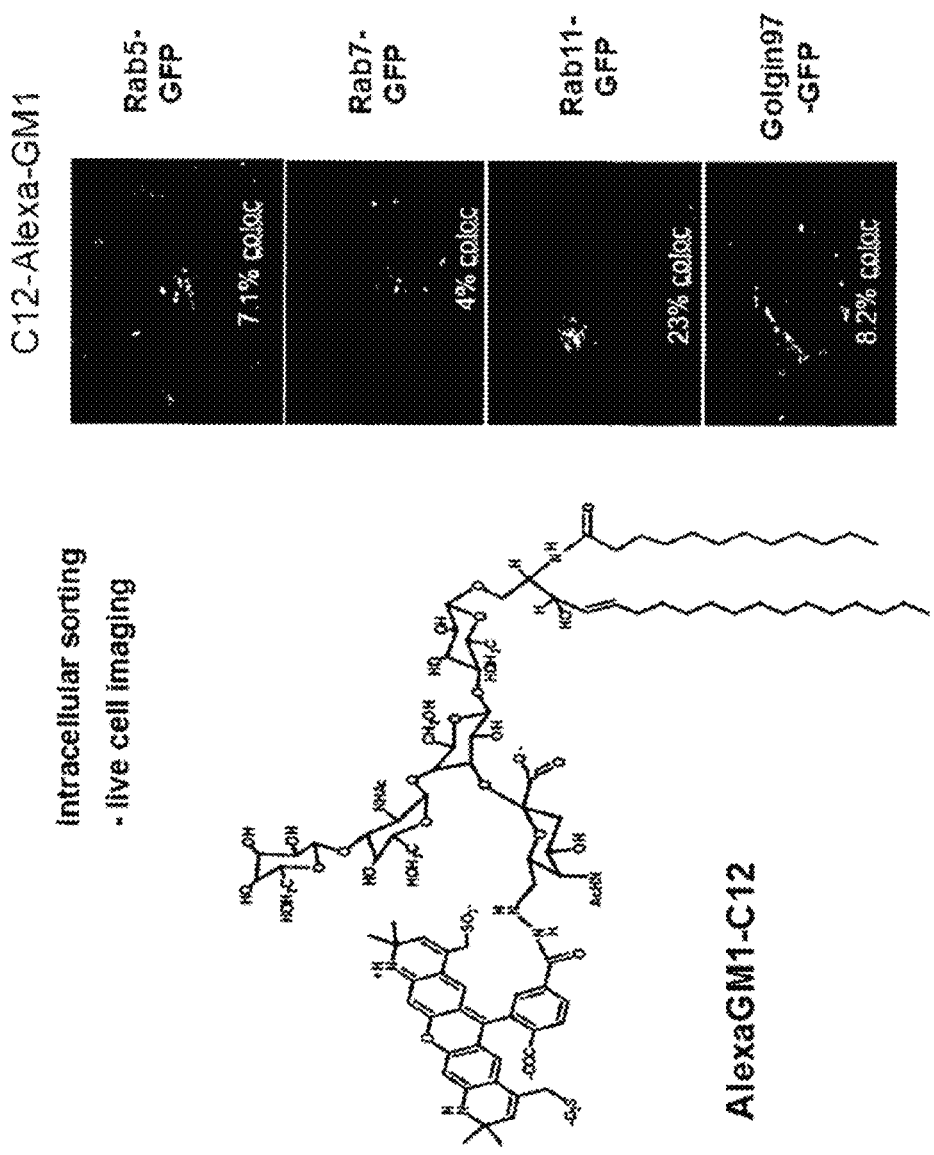
FIGS. 2A and 2B show live confocal imaging of A431 cells with Alexa-GM1-isoforms integrated into the plasma membrane at 37° C. for 1 h. GM1 with ceramide chains containing a short FA C12 (FIG. 2A) or long fatty acid C18 (FIG. 2B) were used. The results show that the short chain ceramide goes to the recycling endosome and trans Golgi network. The long chain ceramide goes to the late endosome rab7 compartment.
Figure 2B:
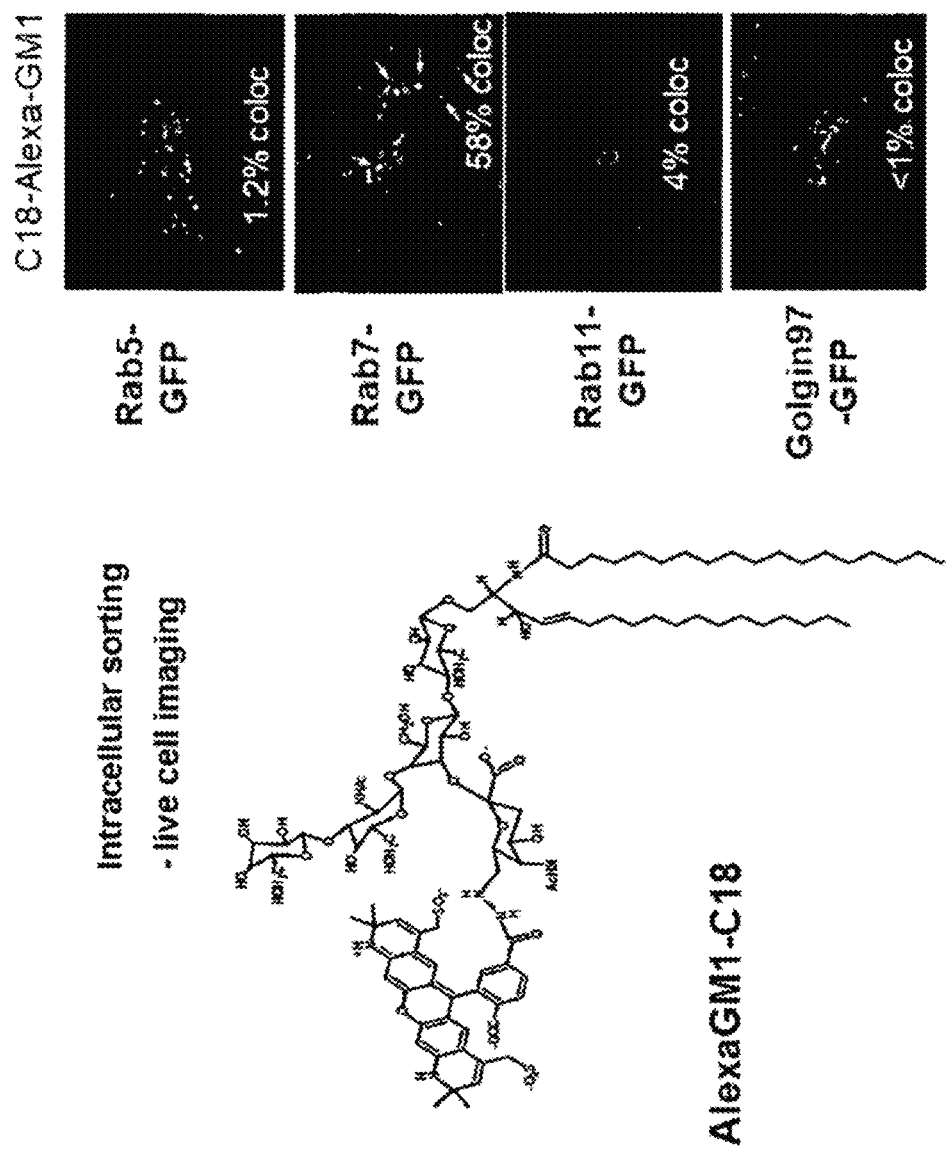
Figure 3:
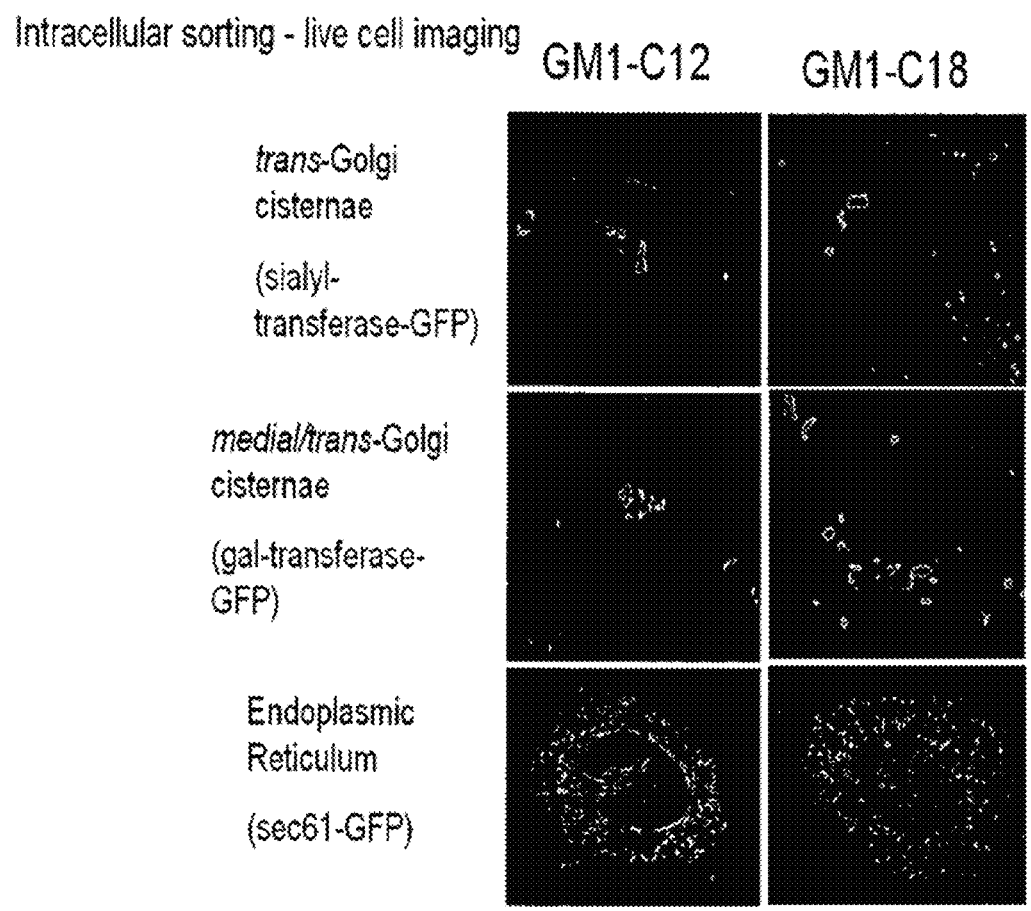
FIG. 3 shows show live confocal imaging of A431 cells with Alexa-GM1-isoforms integrated into the plasma membrane at 37° C. for 1 h. GM1 with ceramide chains containing a short FA C12; or long fatty acid C18 were used. Both GM1 isoforms do not enter the Golgi cisternae or endoplasmic reticulum in detectable quantities.
Figure 4A:
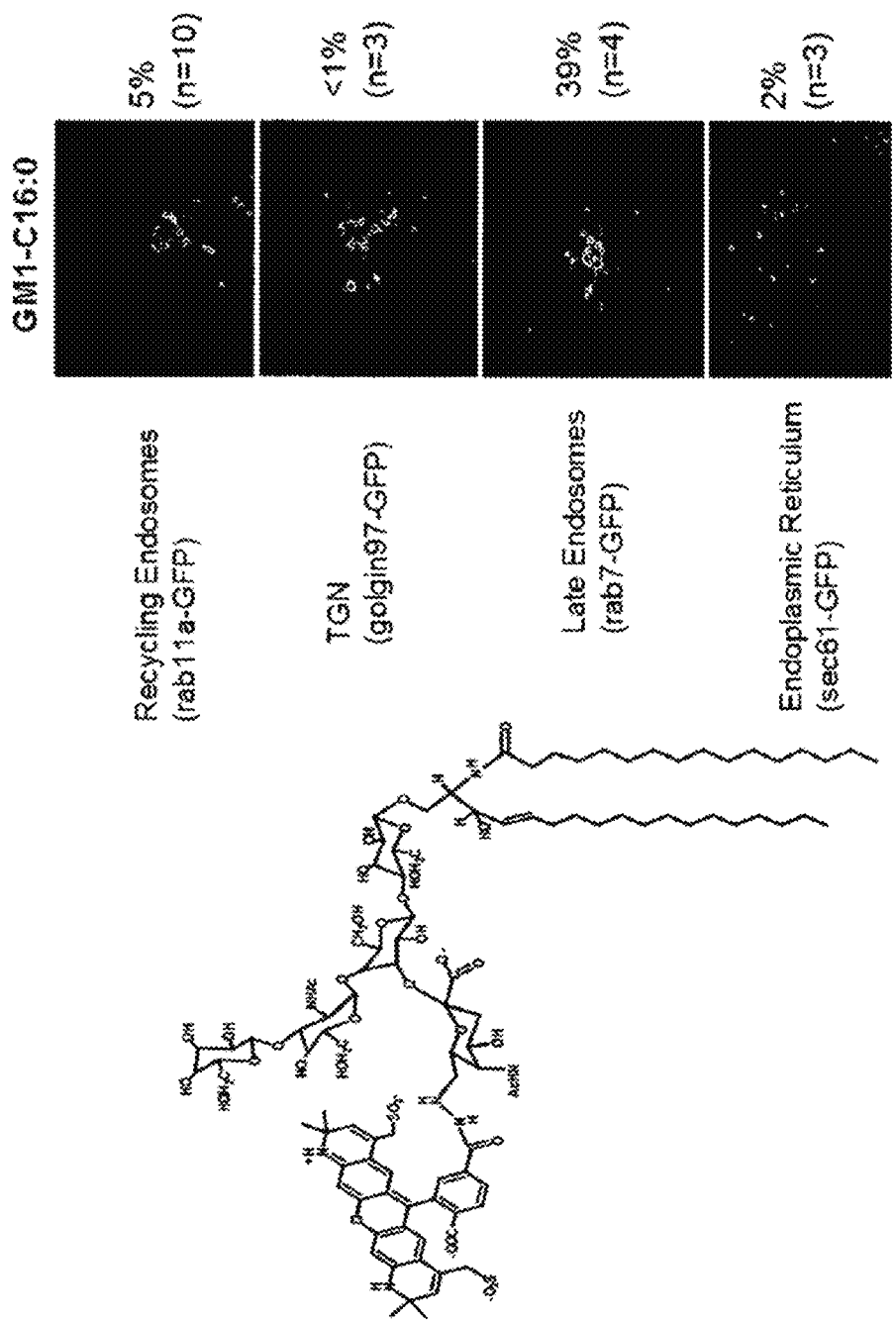
FIGS. 4A and 4B show live confocal imaging of A431 cells with Alexa-GM1-isoforms containing either C16:0 fatty acid (FIG. 4A) or C16:1 fatty acid (FIG. 4B). The fatty acid chains are linked by amide bond to sphingosine typically C18:1. The structural "tipping point" for ceramide structure dictating sorting into the recycling endosome/TGN is a single double bond.
Figure 4B:
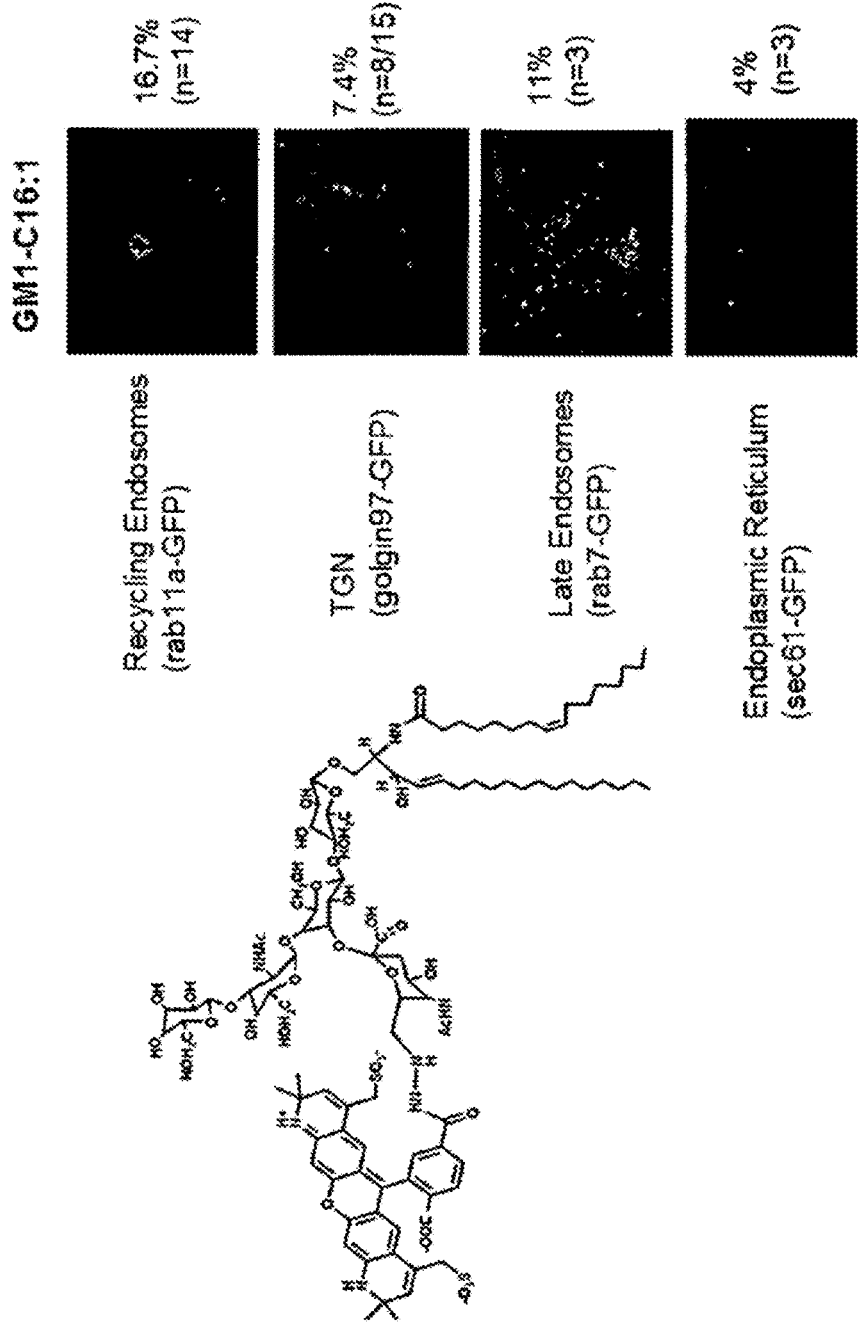
Figure 5:
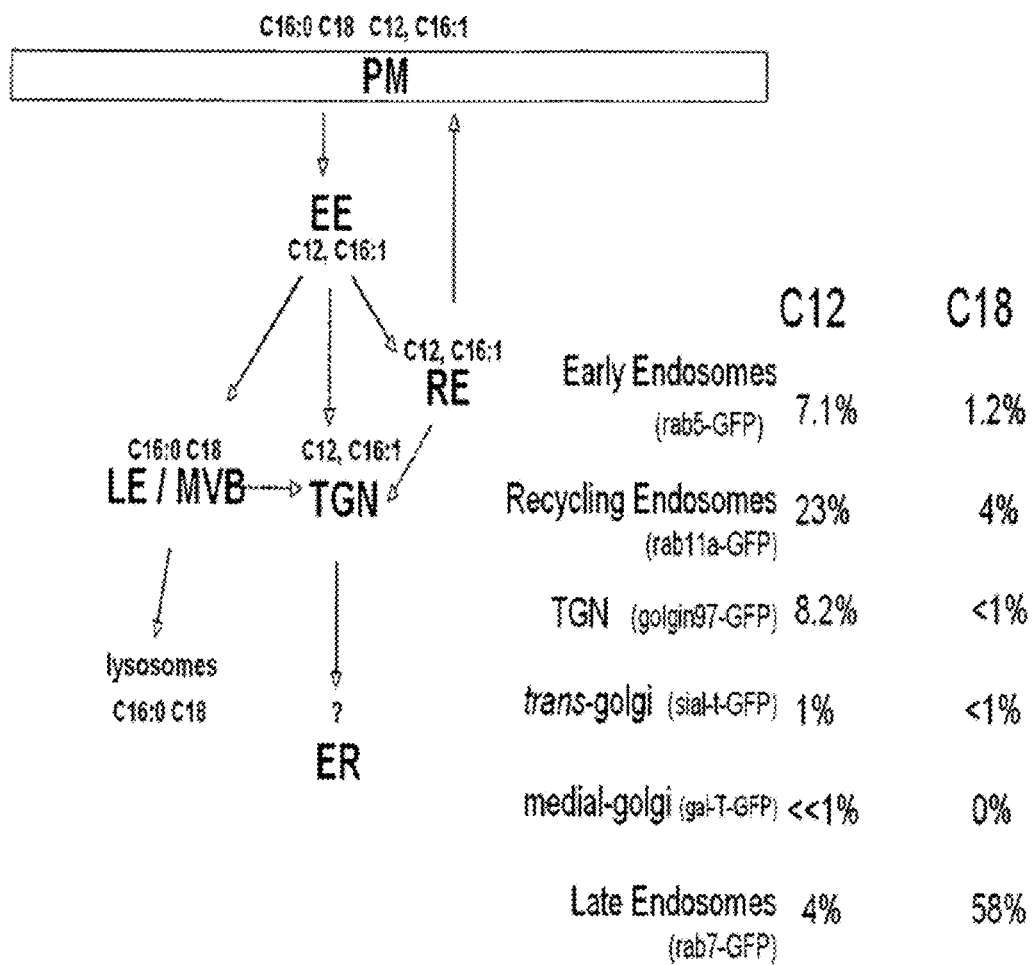
FIG. 5 is a depiction of the intracellular trafficking of ceramide isoforms comprising short chain fatty acid (C12), long chain fatty acid with one cis double bond (C16:1) or long chain saturated fatty acids (C16:0 and C18:0). Sorting occurs at the early endosome (EE). Short chain fatty acids and long chain fatty acids, with at least one cis double bond localize to the recycling endosome (RE) and trans Golgi (TGN), while saturated long fatty acid chains are directed to the lysosomal pathways. A summary of the sorting results at steady state is also presented.
Figure 6:
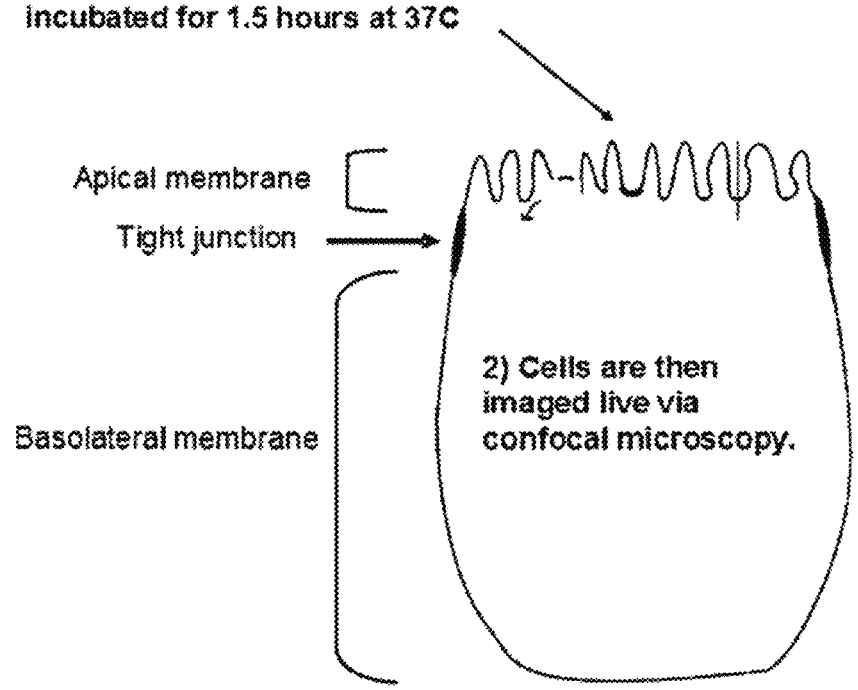
FIG. 6 is a depiction of transcytosis experiments. GM1 lipid comprising either short chain or long chain fatty acids is added to the apical membrane of polarized MDCK cells and incubated for 1.5 h at 37° C. The cells are then imaged live via confocal microscopy.
Figure 6:
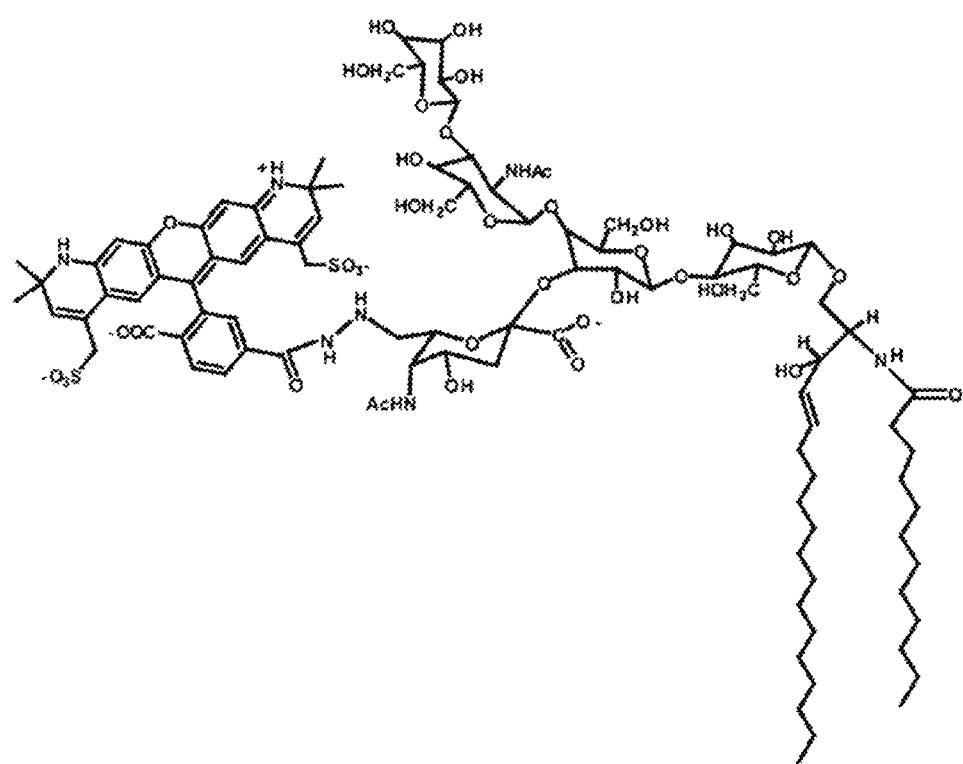
Figure 7:
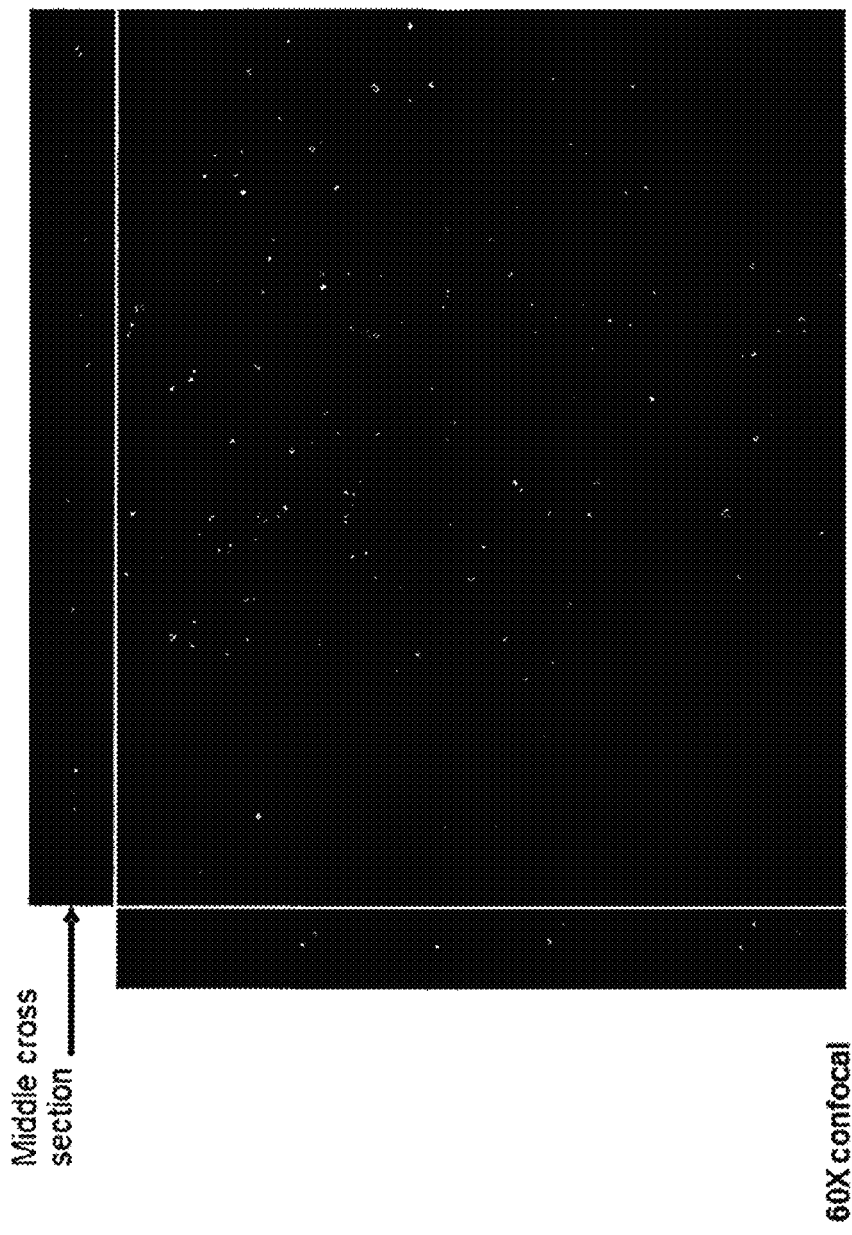
FIG. 7 shows the middle cross-section of MDCK cells with Alexa-GM1 containing short chain fatty acid (C12:0). Short chain C12-GM1 is transcytosed to the lateral membrane in the cells.
Figure 7:
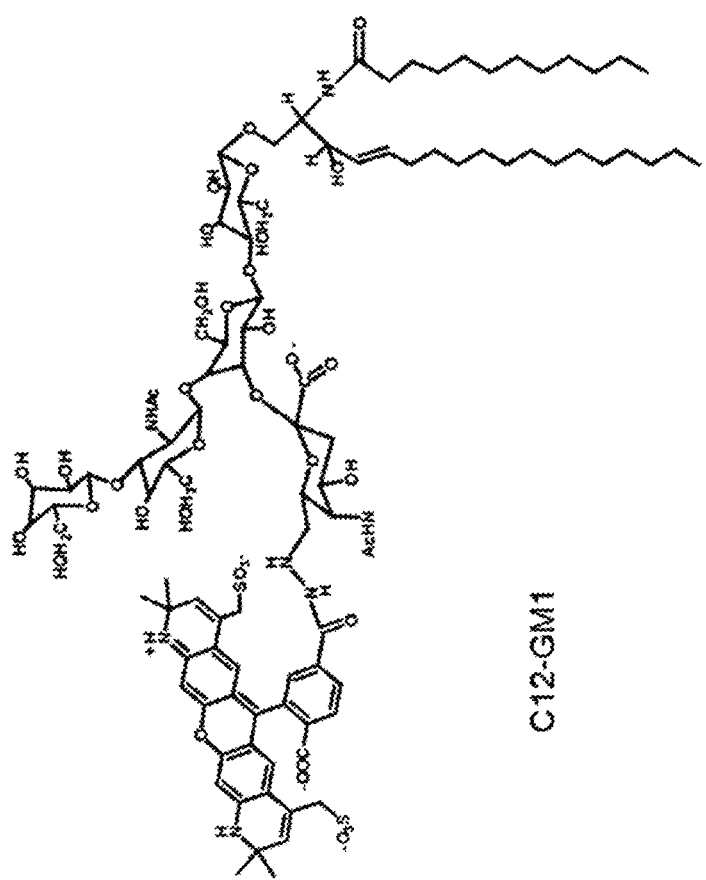
Figure 8:
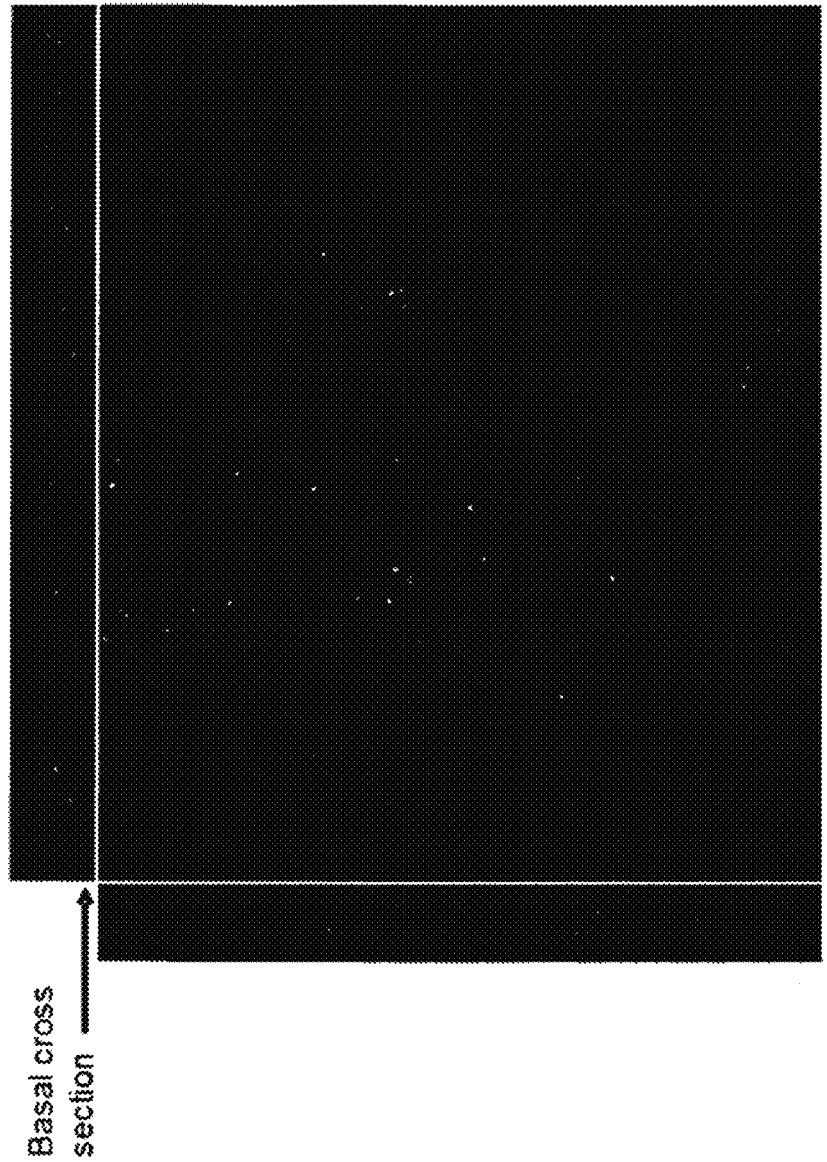
FIG. 8 shows the basal membrane cross-section of MDCK cells with Alexa-GM1 containing short chain fatty acid (C12:0). Short chain C12-GM1 is transcytosed to the basal membrane in the cells.
Figure 8:
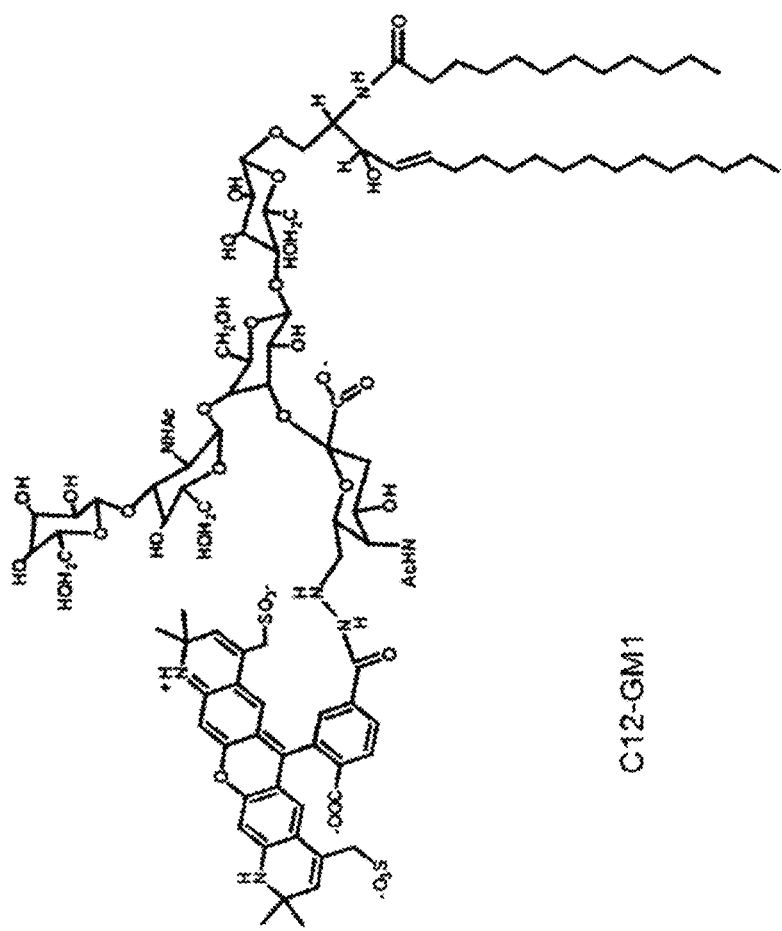
Figure 9:
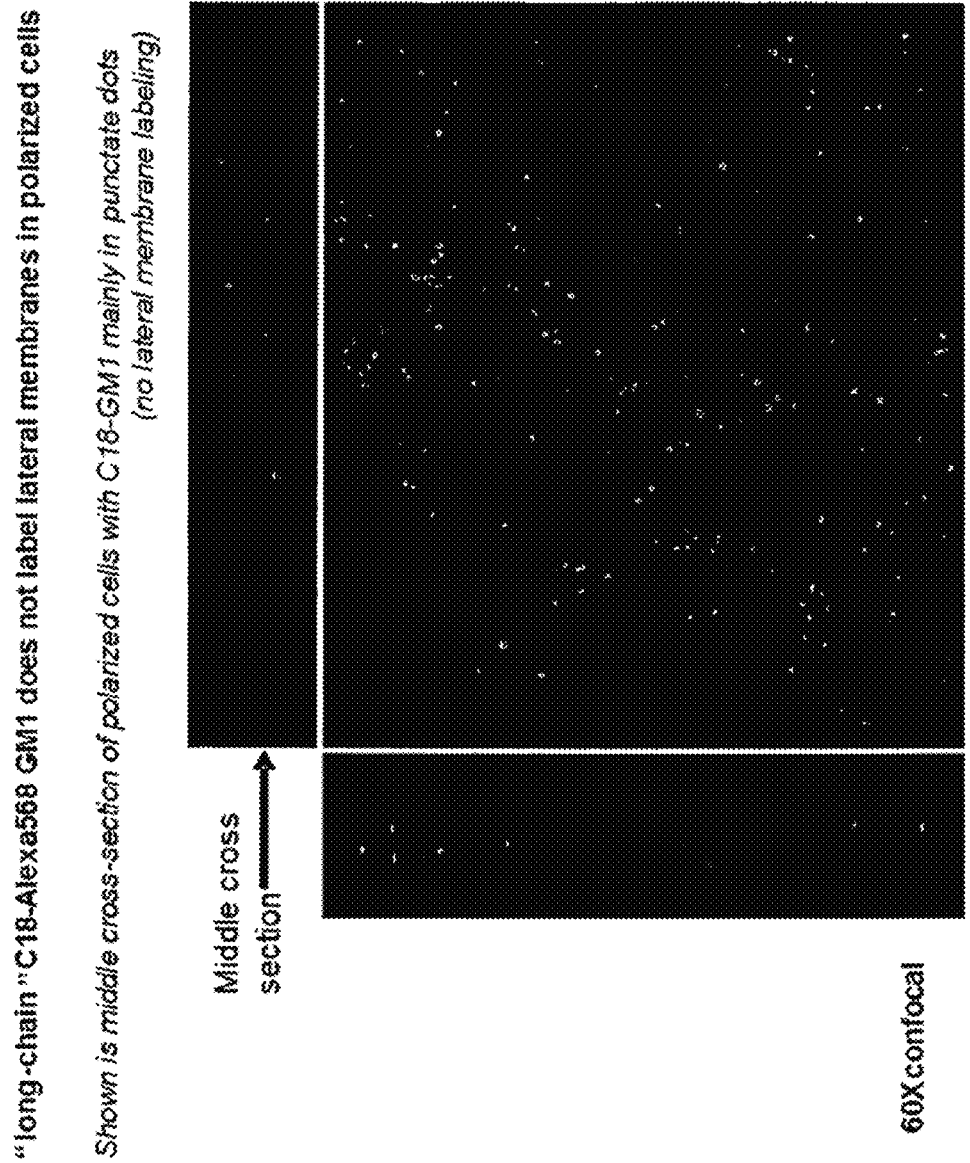
FIG. 9 shows the middle cross-section of MDCK cells with Alexa-GM1 containing long chain fatty acid (C18:0). Long chain C18-GM1 does not label the lateral membrane in the cells.
Figure 9:
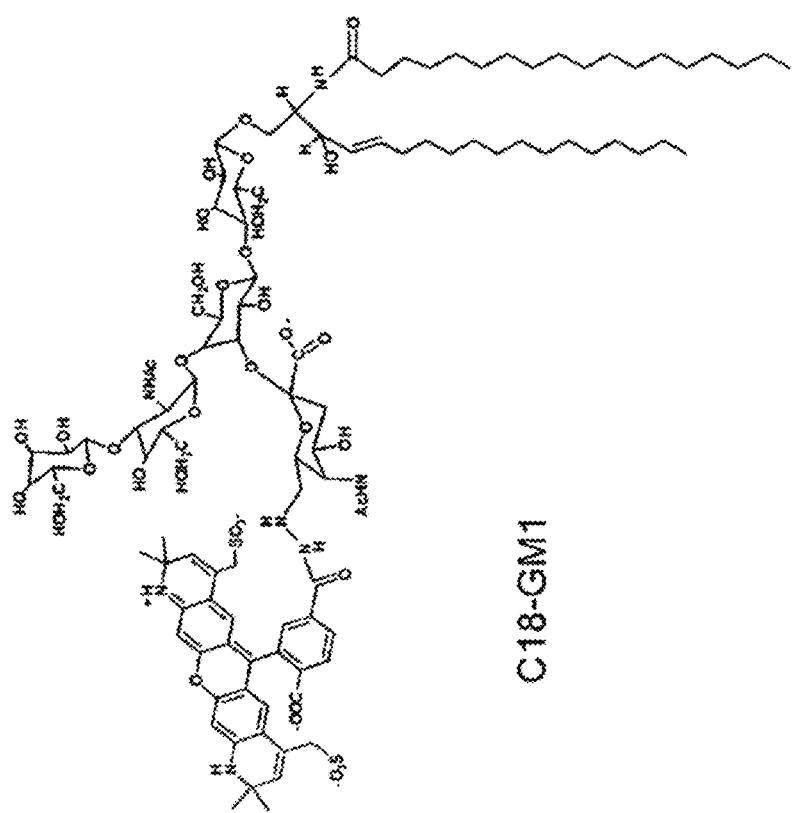
Figure 10:
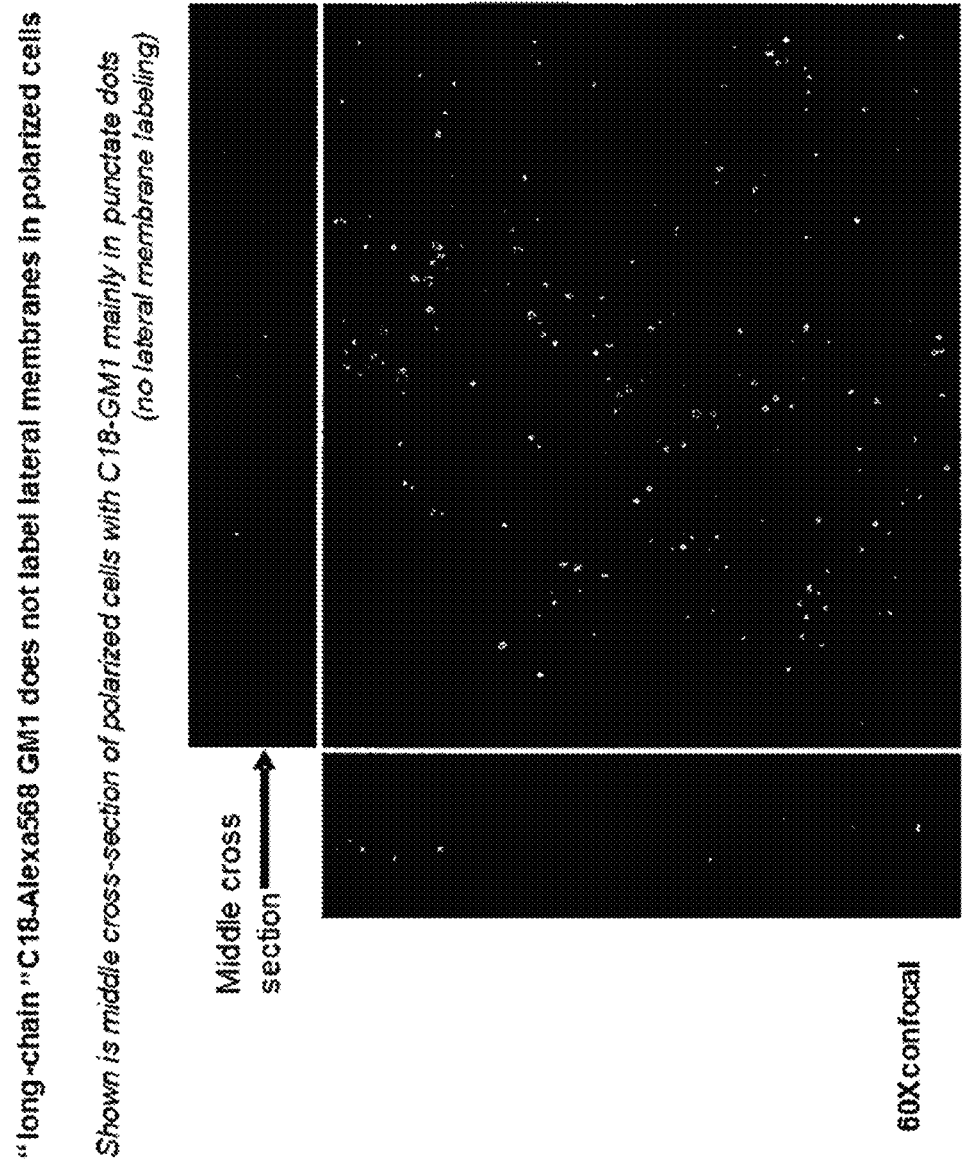
FIG. 10 shows the basal membrane cross-section of MDCK cells with Alexa-GM1 containing long chain fatty acid (C18:0). Long chain C18-GM1 does not label the basal membrane in the cells.
Figure 10:
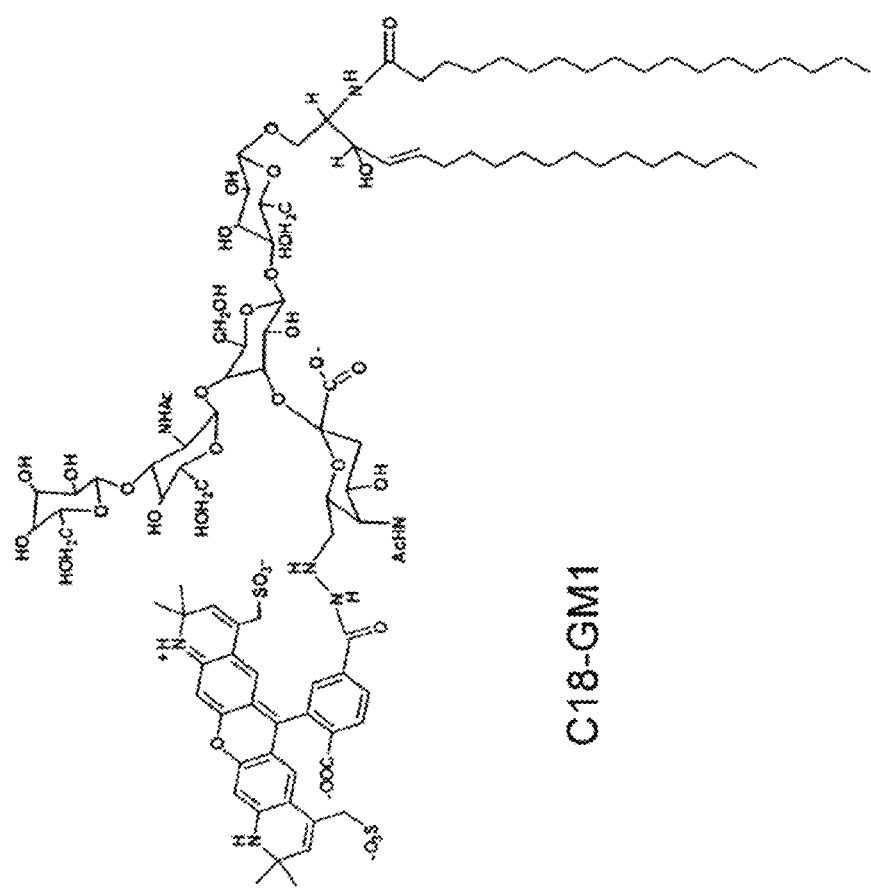

The chemistry for this is by use of a maleimide-hydrazide cross-linker to couple the peptide at its C-terminus to an aldehyde generated in glycerol chain in the sialic acid of the GM1 oligosaccharide by periodate oxidation. The ceramide isoforms are synthesized starting with lyso-GM1 and linking fatty acids of defined structure to the free amine by activation of the fatty acid carboxyl group with dicyclohexylcarbodiimide (DCC) or 1-ethyl-3-(3-dimethylaminopropyl)-carbodiimide (EDC) followed by addition of either N-hydroxysulfosuccinimide (sulfo-NHS) or N-hydroxysuccinimide (NHS) in dimethylsulfoxide (DMSO). Purification is by reverse phase and ion-exchange chromatography FPLC followed by structural confirmation with mass spectroscopy. Lipids synthesized in this way are depicted in FIGS. 1A and 1B.

Example 3

Assessment In Vitro

The novel lipo-peptides prepared above are tested for transcellular transport across cultured polarized epithelial cell barriers in vitro; and for differential trafficking into the recycling or late endosomal/lysosome pathway in non-polarized cells. Only the short chain C12:0 and unsaturated C16:1 ceramides carry the peptide into the transcytotic pathway and away from the lysosome.

The lipo-peptides are introduced to the apical or basolateral membrane of polarized intestinal cells in monolayer culture at 10° C. After subsequent incubation at 37° C., transcytosis is assayed biochemically by selective cell surface biotinylation (the reporter molecule carries free amines providing the reactive group for coupling to biotin) and morphologically by confocal microscopy after fixation and immunostaining for the HA-tag also contained in the reporter peptide.

The control for non-specific paracellular transport is by clamping vesicular traffic in the monolayers at 4° C., and positive control for transcytosis will be by use of the cholera toxin B-subunit (Lencer et al., 1995). An additional positive control to show successful biotinylation of the lipo-peptide is by selective cell surface biotinylation of epithelial monolayers on the same cell surface as lipo-peptide administration and with vesicular traffic clamped at 4° C.

Methods for selective cell surface biotinylation, live and fixed cell confocal microscopy, and transepithelial solute transport are well established (Dickinson et al., 1999; Dickinson et al., 2008; Lencer et al., 1995; Spiekermann et al., 2002).

Example 4

Assessment in Mice In Vivo

The novel lipo-peptides are tested for absorption into or across mucosal surfaces and for enhanced circulating half-life in mice in vivo. Only the short chain C12:0 and unsaturated C16:1 ceramides carry the peptide into the subepithelial space of the exposed mucosal tissues or into the systemic circulation and increase half-life.

The lipo-peptides are introduced into isolated intestinal loops of mice and assayed for absorption and transcellular transport using confocal microscopy in tissue sections as described above. Dose response relationships are established, and positive results will be followed by intra-gastric administration of the lipo-peptides to non-surgically manipulated mice. Absorption into the intestinal mucosa is assessed by microscopy, and systemic absorption is assessed by ELISA developed against the GM1-coupled peptide. The conjunctiva, esophagus, colon, pulmonary tree, and oral mucosal are also tested by topical administration and assayed for absorption into the tissue by confocal microscopy.

To assay for effects on half-life, the novel lipo-peptides or the non-derivatized peptide are injected into mice by IV administration and circulating concentrations assayed by ELISA over time.

The lipo-peptides are assayed in tissue sections after immunolabeling using antibodies against the HA-tag or by direct confocal epifluorescence microscopy after labeling the lipo-peptides with fluorophores before administration.

The ELISA for assay of systemic absorption and half-life is a "sandwich" assay. Capture of the lipo-peptide is by immobilizing antibodies against the HA-epitope tag on 96 well plates. The affinity-captured lipo-peptide is detected by application of HRP-conjugated cholera toxin B-subunit that specifically recognizes the oligosaccharide head group of the derivatized GM1 (binding of toxin remains intact to the modified oligosaccharide, Lencer and Chinnapen unpublished results).

Example 5

Preparation of fusion molecules and in vivo assessment described in this example is preparation of fusion molecules, as exemplified by preparation of fusion molecules comprising insulin-like peptide hormone GLP1 and GM1 isoforms containing ceramide domains with fatty acids of either C18:0 or C12:0.

Prepare fusion molecules between the peptide hormone GLP1 and GM1 with ceramide domains containing fatty acids of either C18:0 or C12:0.

1) Peptide Design

Two basic forms of the active GLP1 peptide with linker-sequences (details described below) are synthesized and are attached to GM1 with short C12:0 (or unsaturated C16:1) chain ceramide domains or long C18:0 chain ceramide domains (as control). The GLP-1 peptides is synthesized with short peptide linkers positioned at the N- or C-terminus and with or without a motif for cleavage by furin. Furin is an intracellular protease localized to the recycling endosome and trans-Golgi network. Cleavage by furin releases the peptide from the ceramide after internalization by mucosal epithelial cells; this may be important to allow for systemic delivery.

Another way to allow for reversible fusion of the peptide to the GM1-carrier is to utilize the native peptide cleavage sites built into the proglucagon sequence (see Box 1 above). The reason for coupling GLP1 to GM1 at either its N- or C-terminus (GM1-GLP1 or GLP1-GM1) is that this allows us to improve the chances for 1) production of a functional fusion molecule, 2) sufficient spatial separation between the two elements to facilitate the biological activities of each, 3) sufficient membrane association/insertion of the GM1 element, and 4) sufficient opportunities for ultimate, but timely, separation of GM I from GLP1. There are also potential advantages to having a non-cleavable peptide-lipid fusion molecule. For example, this might allow for efficient absorption across mucosal barriers, but restrict the therapeutic molecule from going systemic by virtue of the ceramide chain retaining the molecule on the cell membrane; thus allowing for a localized "topical" therapeutic. Such a molecule could be useful for topical delivery of potent anti-inflammatory molecules to mucosal surfaces without systemic toxicity—as currently needed in the treatment of inflammatory bowel disease (IBD) and asthma.

Peptides Synthesized

The active forms of GLP1(7-36)amide and GLP1(7-37) are depicted in Bold. The linker peptides (cleavable and non-cleavable) are depicted in BLACK, and the cleavage sites in Italics.

For peptides in which the penultimate residue is (or will be after proteolytic processing) Arg, this residue is synthesized as Arg(amide) to protect from degradation and extend half-life of the peptide.

1) Coupled Set (CS): Peptide and GM1 Irreversibly Fused Together:

CS-AW-36

(Seq ID No: 1)

CAAWAAWAA-HAEGTFTSDVSSYLEGQAAKEFIAWLVKGR$_{(amide)}$-NH2;
(non-cleavable, coupling at N-terminus)

CS-36-AW (Seq ID No: 2)

HAEGTFTSDVSSYLEGQAAKEFIAWLVKGR-AAWAAWAAC;
(non-cleavable, coupling at C-terminus)

2) Uncoupled Set (US): Peptide Linked to GM1 by Furin-Cleavable Linker Sequence

US-36-FP (SEQ ID NO: 3)

HAEGTFTSDVSSYLEGQAAKEFIAWLVKGR$_{(amide)}$-*RTPRAAAC*;
(furin cleavable linker, coupling at C-terminus)

```
US-FP-36
                                    (SEQ ID NO: 4)
CAAARTPR-HAEGTFTSDVSSYLEGQAAKEFIAWLVKGR(amide)-NH2;
(furin cleavable linker, coupling at N-terminus)
```

3) Native Uncoupled Set (NUS): Peptide Linked to GM1 Allowing for Cleavage at Native Sites in Proglucagon Sequence (See Box 1 Above):

```
NUS-37-AW
                                    (SEQ ID NO: 5)
HAEGTFTSDVSSYLEGQAAKEFIAWLVKGR(amide)G-AAWAAWAAC;
(native C-terminal site for cleavage of pro-GLP1,
coupling at C-terminus)

NUS-PP(N)-36
                                    (SEQ ID NO: 6)
CKRDEFER-HAEGTFTSDVSSYLEGQAAKEFIAWLVKGR(amide)-NH2;
(native N-terminal site for cleavage of pro-GLP1,
coupling at N-terminus)
```

4) Alternative Linker Peptide for Groups 1 and 3 Above:

The linker peptide sequence CGGPGGPGG (GP) (SEQ ID NO.: 9) has different rotational mobility and allows for a second approach to optimize function of the GLP1 or ceramide domains or both.

Each peptide-lipid fusion is independently confirmed for structure and purity by mass spectrometry and for function in an in vitro assay for GLP1-induced cAMP response using CHO cells expressing the hGLP-1 receptor (R7 cells) (Xiao et al., 2001). The utility of GM1 fusions to the C- and N-terminus of GLP1 is assessed starting with with two peptides (CS N- and C-terminal linker pairs). Based on the activities of these fusion molecules in the R7 cell cAMP assay, the US and NUS peptides as C- or N-terminal fusions, or both, are prepared.

2) Fusion to GM1-Ceramide Isoforms

The coupling chemistry utilizes, a simple three-step process, that has been already verified in our studies on Alexa-GM1 isoforms described above and shown in Figures.

1) Aldehyde moieties are generated in the sialic acid residue in the GM1 headgroup with sodium periodate, which selectively oxidizes the C7 position of the glycerol side chain when performed on ice for one hour. The reaction proceeds to completion and periodate is quenched with excess free glycerol (Murray et al., 1989).

2) The newly generated aldehydes are reactive handles for nucleophilic-attack by a hydrazide-maleimide bi-functional reagent, namely 4-(4-N-Maleimidophenyl) Butyric Acid Hydrazide Hydrochloride (MPBH, Pierce). The aldehyde-hydrazide reaction is very efficient, and creates a hydrazone bond that can be specifically reduced with sodium cyanoborohydride to form a stable covalent linkage (Hermanson, 1996). The modified MPBH-coupled GM1 is then purified by preparative TLC.

3) The free sulfhydryl of the terminal Cys residues in each of the CS-, US-, and NUS-GLP1 peptides are then sites for covalent coupling to the maleimide reactive group on MPBH-GM1 (Hermanson, 1996). The final GLP1-GM1 conjugates will be purified by HPLC and structure verified by mass spectrometry.

Test the utility of GLP1-ceramide fusion molecules for mucosal absorption and extension of half-life in vivo using the ob/ob mouse.

The first step in analyzing the lipo-peptides described above in vivo is to verify the retention of the biological activity of GLP1. This is readily achieved by monitoring blood glucose levels (glucose tolerance curves) in diabetic (ob/ob) mice following intraperitoneal (IP) injection. Biologically-active GLP1 induces a release of insulin, inhibition of glucagon, and subsequent drop in blood sugar; basically providing for a regulation of orally or IP administered glucose (Doyle and Egan, 2001). Experimental details are described further below. Briefly, a nick in the tail of a mouse is made to attain 5 µl of whole blood, which is then placed directly on commercially-available test strips and read immediately using a glucometer. The instrumentation and assay for serum glucose is now very low technology, extremely easy to use, and highly robust. Time-points which have been successful for glucose monitoring of biological activity of GLP1 following IP injection are: 2 pre-dose values, 15, 30, 45 min, 1, 2, 3 and 4 hours post-dose. Since the half-life of GLP1 is very short and difficult to measure in the blood, this bioassay is the most sensitive and effective means to measure the presence of biologically active GLP1.

The next step is to test for the effect of lipid modification on half-life and absorption via the intestine and respiratory tract; using the same bioassay. The approach is exactly the same as used to test for receptor-mediated mucosal absorption and extension of half-life of erythropoietin fused to human Fc (by the Fc-receptor FcRn) (Spiekermann et al., 2002).

For testing absorption across the intestine, diabetic (ob/ob) mice are fasted overnight and after light $CO_2$ anesthesia intragastric-gavage fed the GLP1-GM1 fusion molecules (GM1-C12:0 fusion and GM1-C18:0 as control), no peptide, or the native GLP-1 not fused to GM1 in strongly $HCO_3$-buffered salt-glucose solution. Glucose monitoring is obtained from tail-nick (5 µl of whole blood) as described above: 2 pre-dose values, 15, 30, 45 min, 1, 2, 3 and 4 hours post-dose.

For testing absorption across the respiratory tract, diabetic (ob/ob) mice are fasted overnight and after light $CO_2$ anesthesia several drops of fusion peptides in phosphate-saline buffered solution dropped into the nose. This delivers the peptide to regions of both the upper and lower airways (Spiekermann et al., 2002). Glucose monitoring is obtained from tail-nick (5 µl of whole blood) as described above: 2 pre-dose values, 15, 30, 45 min, 1, 2, 3 and 4 hours post-dose.

The experimental design and logic are outlined in greater detail below.

Interpretation:

A drop in serum glucose occurs during glucose tolerance tests with the concurrent administration of GLP1-peptides fused to GM1 isoforms containing C12:0 or C16:1 ceramide chains, but no such drop in serum glucose occurs with GLP1-peptides fused to long-saturated C18:0 GM1 isoforms, is consistent with absorption by transcytosis of the short chain/unsaturated chain ceramides; and consistent with prolonged half-life. Such evidence provides proof of principle for the proposed technology and sets the stage for further analysis of the pathways involved and development of therapeutic applications.

Other potential applications include: ceramide chain fused to recombinant IL-10 as an example of a topical (locally acting) therapeutic to calm inflammatory mucosal diseases; and fusions of the ceramide to clotting factors VIII or IX so as to prolong half-life when administered parenterally as treatment for hemophilia.

The technology represents a platform for drug delivery with many other potential applications including the re-design of small molecule and protein therapeutics already in use clinically.

Alternative Approach:

Introduction of CS and US constructs into exposed loops of jejunum or ileum can be performed under general anesthetic in obese mice (as done before (Rufo et al., 1997)) with blood draws for blood glucose being taken after peptide administration over a 45 min to 1 hr time frame as proposed above; and prior to euthanasia and collection of intestinal and liver tissue samples. Bioassay for GLP1 absorption is performed by measuring blood glucose levels, as described above.

Detailed Methods for In Vivo Studies

Study 1: Test the Utility of N- Vs C-Terminal Fusions of the CS-GLP1-GM1, US-GLP1-GM1, and NUS-GLP1-GM1 Fusion Molecules (IP Injections);

Rationale: The functionality of the fusion molecules is tested in vivo.

Study design: Each fusion molecule is studied at 5 µM in separate experiments by IP injection into the treatment groups listed below. Because the glucose tolerance tests (GTT) in ob/ob mice after IP injection are so robust (>5-fold reduction in BS and highly reproducible), 5 mice in each group are used. Fusions to both the GM1-C12:0 and GM1-C18:0) isoforms are tested. Due to the size of this study, the experiment are carried out in segments, but always including groups 1 and 2 (negative and positive controls) as "2-point calibrations".
1) No peptide (negative control)—ob/ob mice show highly abnormal GTT
2) Native peptide (positive control—no fusion with lipid)—ob/ob mice show normalized GTT
3a) Long-chain N-terminal peptide fusion
3b) Short-chain N-terminal peptide fusion
4a) Long-chain C-terminal peptide fusion
4b) Short-chain C-terminal peptide fusion Method:
Fast animals overnight
Obtain 2 pre dose BS
Mouse upside down—Intraperitoneal injection of glucose (2 g/kg) in saline mixed together with GM1-peptide (5 µM)
Measure blood sugar (BS) in about 5 µl whole blood obtained from tail nick at 15, 30, 45 min and 1, 2, 3, 4 hours.
Allow recovery and recycle animal for other studies, or if this cannot be validated for reliable GTT in subsequent experiments, we will sacrifice the animal by $CO_2$ asphyxiation and use new animals for each experiment.

Results will show whether N- or C-terminal peptide fusions (or both) are functional in vivo and suggest a hierarchy of potencies.

Study 2: Probe the Dose-Dependency of Selected Peptide-GM1 Fusion Molecules—IP Injections, High Dose Peptides Rationale: These studies determine the ED50 for selected fusion molecules tested for utility in mucosal absorption.

Study design: Each fusion molecule is studied in separate experiments by IP injection into the treatment groups listed below. 5 mice will be used in each group.
1) No peptide (negative control—defines baseline abnormal GTT)
2) Selected peptide-GM1 fusion molecule (5 µM estimated highest dose); GM1(C12:0) and GM1(C18:0) pair.
3a-e) Selected peptide-GM1 fusion molecule (serial 0.5-log dilutions); GM1(C12:0) and GM1(C18:0) pairs Method: Same as for Study 1.

Results will determine the ED50 for selected GM1(C12:0) and GM1(C18:0) fusion molecules when administered parenterally. The E50 is used to determine the dosing for mucosal absorption studies (typically 30- to 50-fold higher than ED50 for IP administration).

Study 3: Test Oral Gastric Gavage (or Nasal Administration) of Selected Fusion Molecules.

Rationale: These studies determine the utility of fusing a therapeutic protein to the short or long isoforms of GM1 as a vehicle allowing for mucosal absorption.

Study design: Selected fusion molecules are studied based on potency as defined in Studies 1 and 2 above. Each fusion molecule (C12:0 and C18:0 pairs) and route of administration are studied in separate experiments using the treatment groups listed below. 5 mice are used for the no peptide negative control group and 10 mice are used for mucosal administration groups due to the predicted greater variability in response after mucosal administrations. Power calculations based on the predicted >5-fold effect size for treatment vs no treatment.
1) No peptide (negative control)—ob/ob mice show highly abnormal GTT
2) Selected peptide-GM1 fusion administered IP (positive control)
3a) Short-chain N/C-terminal peptide fusion administered by gastric gavage or intra-nasal (50-fold×ED50 IP dose)
3b) Long-chain N/C-terminal peptide fusion administered by gastric gavage or intra-nasal (same dose as for short-chain isoform, group 3a above)

Method:
Fast animals overnight
Obtain 2 pre dose BS
Isofluorane anesthesia (2-4% delivered by isoflurane machine in ARCH animal facility). The isoflurane anesthesia has no effect on GTT
Mouse upside down—inject glucose (2 gm/kg) in saline
Mouse upright—gavage peptide-GM1 fusions (or drop into nose)
Measure blood sugar (BS) in about 5 µl whole blood obtained from tail nick at 15, 30, 45, 60 min.
allow to wake up
Continue measures of blood sugar (BS) in about 5 µl whole blood obtained from tail nick at 2 h 3 h, 4 h
Allow recovery and recycle animal for other studies or sacrifice by $CO_2$ asphyxiation (as above—see Study 1).

Results will show whether that GM1-isoforms with short-chain ceramide domains will allow for mucosal absorption by acting as vehicles for transport across the epithelial cell by transcytosis.

Study 4: Direct Injection of Selected Peptide into Ileal Lumen (50× of ED50).

Rationale: If the gastric-gavage studies are negative for absorption, this result would suggest that the peptide-GM1 fusion molecules might be degraded by digestive enzymes. These studies will test the idea by by-passing the major sites of intestinal digestion via direct application to the Ileal mucosa.

Study design: Selected fusion molecules are studied as described in Study 3. Each fusion molecule (C12:0 and C18:0 pairs) are studied in separate experiments using the treatment groups listed below. 5 mice are used for the no peptide negative control group and 10 mice are used for intra-ileal administrations.

1) No peptide (negative control)—ob/ob mice show highly abnormal GTT
2) Selected peptide-GM1 fusion administered IP (positive control)

3a) Short-chain N/C-terminal peptide fusion intra-ileal (50-fold×ED50 IP dose)
3b) Long-chain N/C-terminal peptide fusion intra-ileal (same dose as for short-chain isoform, group 3a above)

Method:
Fast animals overnight
Obtain 2 pre dose BS
Isoflurane anesthesia (2-4% delivered by isoflurane machine in ARCH animal facility).
  clean, shave, open abdomen with animal on warming table
  isolate ileum
  $2^{nd}$ pre dose BS—two measures
  inject peptide-GM1 fusion into lumen of ileum
  immediately administer the IP dose of glucose in saline to peritoneal cavity
  close peritoneum
  Measure blood sugar (BS) in about 5 µl whole blood obtained from tail nick at 15, 30, 45, 60, 90, and 120 min.
  Sacrifice animal by $CO_2$ asphyxiation Results will show whether GM1-isoforms with short-chain ceramide domains will allow for mucosal absorption by acting as vehicles for transport across the epithelial cell by transcytosis.

Example 6

Delivery of TLR-Adjuvant Across an Epithelial Barrier In Vitro

The TLR5 agonist FliC (*salmonella* flagellin) is coupled to short-chain or long chain ceramides, and the fusion molecules are applied to apical membranes of polarized intestinal epithelial cells in monolayer culture. (FliC is still functional after fusions to either the N- or C-terminus.) Delivery across the monolayer is detected by activation of TLR5 on the basolateral membrane. The fusions to long or short chain ceramides provide control for each other by directing the molecule into the lysosome or transcytotic pathways respectively. FliC alone provides additional control. The TLR5 is assessed by measuring secretion of the cytokine IL8, the chemokine CCL20, and the B-cell activating factors BAFF and APRIL. These studies show if ceramide can direct the fusion molecules across epithelial barriers.

Next, delivery of antigen to professional antigen-presenting cells located in the sub-epithelial space is modeled. Here, the immunogenic OVA peptide (ovalbumin residues 323-339; ISQAVHAAHAEINEAGR; SEQ ID NO: 7) coupled to the ceramide lipids is used, with and without the additional fusion to FliC (antigen plus adjuvant in one molecule). The transport of the OVA peptide across the harrier is determined by applying the "conditioned" basolateral cell media to isolated dendritic cells and OT-II lymphocytes. The OT-II T-cell clone reacts specifically with the OVA peptide when presented on dendritic cells by proliferation, and this is detected by radioactive thymide incorporation assay. OVA peptide alone provides additional control.

The ability of the short or long (control) chain ceramides fused to FliC-OVA-peptide to carry the complex across mucosal barriers in the mouse intestine or respiratory tract to induce antigen-specific T cell responses is tested. Both these mucosal surfaces strongly restrict absorption of such molecules—a key reason mucosal vaccinations have been such a difficult challenge. Here, $10^7$ OT-II T cells are adoptively transferred into C57Bl/6 mice and the FliC-OVA-ceramide fusion molecules (or FliC-OVA alone as additional control) are applied intragastrically or intranasally in 1 to 3 doses. Five days after the last dose, CD4+ T cells from spleen or mesenteric lymph nodes are harvested, mixed with irradiated splenocytes pulsed with OVA peptide, and assayed for CD4+ T cell proliferation by radioactive thymidine incorporation assay. Differentiation of the CD4+ T cells into Th1, TH2, TH17 phenotypes is assayed by measuring INFγ, IL4, and IL17 respectively (ELISA). Measuring total luminal SIgA concentrations provides an indirect measure of induction of BAFF or APRIL through activation of basolateral TLR5.

Ceramide fusion molecules are reconstituted into liposomes, which might act as particles for targeting delivery to M-cells in the epithelium over Peyer's patches. As discussed above, targeting vaccine antigens to M cells has been the main focus of the field so far. Though this technology is different, it is predicted to enhance transport across the M cell pathway as well. Immune responses evoked by this formulation are compared with responses to the soluble ceramide complexes; and to the immune responses obtained after coupling the FliC-OVA to liposomes (or other inert particles) in the absence of the ceramide vehicle.

The technology represents a novel platform for mucosal vaccination against rotavirus (major cause of diarrhea), since protective antigens VP6 or VP7 are already identified. The technology can also be used for protective vaccines against other mucosal pathogens (TB, HIV, *salmonella, shigella, Vibrio*, intestinal parasites).

Example 7

To study the biology of the gangliosides, isoforms of GM1 were synthesized containing the fluorophore ALEXA 568 coupled to the GM1 oligosaccharide head-group (located outside the membrane) and with the following fatty acids in the ceramide domain: C12:0, C16:0, C16:1; C18/20:0 (FIGS. 1A and 1B). This allowed for structure function studies on the ceramide domain The ALEXA-labeled gangliosides were introduced into human epithelial A431 cells expressing eGFP-proteins localized to specific intracellular compartments (Rab11a, recycling endosome; Rab7, late endosome; Golgin97, TGN) and the trafficking of the ganglioside was followed in live cells by confocal microscopy in 4- or 5-dimensions (3-D space, time, and color) (see details below).

GM1 with short chain C12:0 and "kinked chain" C16:1 ceramides localized to the recycling endosome, plasma membrane, and trans-Golgi network (TGN) (See Figures). The fully saturated long chain C18/20:0 and C16:0 gangliosides localized to the late endosome/lysosome (see Figures). Our results are consistent with the hypothesis that the "kinked" or short chain shape of the lipid allows for movement across the sharp bends and curves of sorting tubules and vesicles so as to allow the lipid to escape the degradative late endosome/lysosome.

Trafficking of Short Chain and "Kinked" Chain GM1-Ceramide Isoforms into the Recycling Endosome Human A431 epithelial cells stably expressing Rab11a-GFP (green) to physiologically mark the recycling endosome were incubated with Alexa(red)-labeled GM1 isoforms for 60 min. After washing, the cells were imaged alive by confocal microscopy. The trafficking of GM1 into the Rab11a endosome in 3 dimensions at steady state was quantified by first identifying Rab11a-eGFP- and GM1-containing objects using an automatic threshold-finding algorithm (Volocity, Improvision Inc., (Costes et al., 2004), and analyzing the co-localization between Rab11a and GM1 using the Manders colocalization coefficient (termed $M_{target\ protein}$). The Manders coefficient measures the strength of colocalization on a scale from 0-1, with 0 indicating no colocalizing signals and 1 indicating perfect colocalization. The distribution of Manders coefficients for each object is displayed as a scatter plot using 3D data obtained from multiple cells and independent experiments as indicated.

Methods for Quantitative Measures of GM1 Trafficking and Co-Localization in Specific Endosomal Compartments.

Quantitation of the fraction of a given target protein in a 3D-masked endosomal compartment was determined by the following protocol: 1) object masks were created by segmenting the compartment's marker protein or lipid fluorescent intensity above the local background using an automatic and unbiased threshold finder (Volocity. (Costes et al., 2004)); 2) the colocalization coefficients (Manders 1992) were measured within the masked region using Volocity (Improvision, Coventry, England). These coefficients vary from 0 to 1, the former corresponding to non-overlapping images and the latter reflecting 100% colocalization between both images. 3) The fraction of a protein contained within a defined compartment (termed $M_{Target\ Protein}$) is defined as the ratio of the summed of pixels intensities ($M_{Target\ Protein}$) from the green image (e.g. target protein/lipid), for which the intensity in the red channel (compartment protein) is within the selected intensity thresholds, over the sum of all pixel intensities from the green image channel above background. Thus, $M_{Target\ Protein}$ is a good indicator of the proportion of the green signal coincident with a signal in the red channel over its total intensity.

Example 8

Real-Time Live Cell Imaging of A431 Epithelial Cells Trafficking Alexa-GM1 Isoforms: Only Short Chain Ceramides Enter Sorting Tubules Human A431 epithelial cells stably expressing Rab7-GFP (green) to physiologically mark the late endosome were incubated with Alexa(red)-labeled GM1 isoforms and imaged in real time by confocal microscopy in 5-dimensions. Only the short (C12, panel a) and 'kinked" (C16:1, not shown) GM1 isoforms entered sorting tubules of the endosomal compartment. This result is consistent with the hypothesis of lipid sorting by membrane curvature. The short chain ceramides escape the endosomal vesicle into sorting tubules that traffic the GM1 to the recycling endosome and into the transcytotic pathway. The long chain ceramides (panel b), however, are trapped in the large vesicle and this matures into the late endosome (see cartoon, panel c). This may explain how the structure of the ceramide domain acts to influence GM1 trafficking.

LITERATURE CITED

Brown, D. A. 2006. Lipid rafts, detergent-resistant membranes, and raft targeting signals. Physiology (Bethesda). 21:430-9.

Dickinson, B., K. Badizadegan, Z. Wu, J. C. Ahouse, X. Zhu, N. E. Simister, R. S. Blumberg, and W. I. Lencer. 1999. Bidirectional FcRn-dependent IgG transport in a polarized human intestinal cell line. J. Clin. Invest. 104:903-911.

Dickinson, B. L., S. M. Claypool, J. A. D'Angelo, M. L. Aiken, N. Venu, E. H. Yen, J. S. Wagner, J. A. Borawski, A. T. Pierce, R. Hershberg, R. S. Blumberg, and W. I. Lencer. 2008. Ca2+-dependent Calmodulin Binding to FcRn Affects Immunoglobulin G Transport in the Transcytotic Pathway. Mol Biol Cell. 19:414-423.

Lencer, W. I., S. Moe, P. A. Rufo, and J. L. Madara. 1995. Transcytosis of cholera toxin subunits across model human intestinal epithelia. Proc. Natl. Acad. Sci. USA. 92:10094-10098.

Lencer, W. I., and B. Tsai. 2003. The intracellular voyage of cholera toxin: going retro. Trends Biochem Sci. 28:639-45.

Maxfield, F. R., and T. E. McGraw. 2004. Endocytic recycling. Nat Rev Mol Cell Biol. 5:121-32.

Mukherjee, S., and F. R. Maxfield. 2000. Role of membrane organization and membrane domains in endocytic lipid trafficking. Traffic. 1:203-11.

Mukherjee, S., T. T. Soe, and F. R. Maxfield. 1999. Endocytic sorting of lipid analogues differing solely in the chemistry of their hydrophobic tails. J Cell Biol. 144.

Simons, K., and R. Ehehalt. 2002. Cholesterol, lipid rafts, and disease. J Clin Invest. 110:597-603.

Simons, K., and W. L. Vaz. 2004. Model systems, lipid rafts, and cell membranes. Annu Rev Biophys Biomol Struct. 33:269-95.

Spiekermann, G. M., P. W. Finn. E. S. Ward, J. Dumont, B. L. Dickinson, R. S. Blumberg, and W. I. Lencer. 2002. Receptor-mediated immunoglobulin G transport across mucosal barriers in adult life: functional expression of FcRn in the mammalian lung. J Exp Med. 196:303-10.

Tsai, B., C. Rodighiero, W. I. Lencer, and T. Rapoport. 2001. Protein disulfide isomerase acts as a redoxdependent chaperone to unfold cholera toxin. Cell. 104:937-948.

Brown, D. A. 2006. Lipid rafts, detergent-resistant membranes, and raft targeting signals. Physiology (Bethesda). 21:430-9.

Costes, S. V., D. Daelemans, E. H. Cho, Z. Dobbin, G. Pavlakis, and S. Lockett. 2004. Automatic and quantitative measurement of protein-protein colocalization in live cells. Biophys J. 86:3993-4003.

Doyle, M., and J. Egan. 2001. Glucagon-like peptide-1. Recent Prog Honn Resch. 56:377-99.

Hermanson, G. T. 1996. Bioconjugate Techniques. Academic Press, San Diego, Calif.

Kieffer, T. J., and J. F. Habener. 1999. The glucagon-like peptides. Endocr. Rev. 20:876-913.

Lencer, W. I., S. Moe, P. A. Rufo, and J. L. Madara. 1995. Transcytosis of cholera toxin subunits across model human intestinal epithelia. Proc. Natl. Acad. Sci. USA. 92:10094-10098.

Lencer, W. I., and B. Tsai. 2003. The intracellular voyage of cholera toxin: going retro. Trends Biochem Sci. 28:639-45.

Maxfield, F. R., and T. E. McGraw. 2004. Endocytic recycling. Nat Rev Mol Cell Biol. 5:121-32.

Mukherjee, S., and F. R. Maxfield. 2000. Role of membrane organization and membrane domains in endocytic lipid trafficking. Traffic. 1:203-11.

Mukherjee, S., T. T. Soe, and F. R. Maxfield. 1999. Endocytic sorting of lipid analogues differing solely in the chemistry of their hydrophobic tails. J Cell Biol. 144.

Murray, M. C., V. P. Bhavanandan, E. A. Davidson, and V. Reinhold. 1989. Modification of sialyl residues of glycoconjugates by reductive amination. Characterization of the modified sialic acids. Carbohydr Res. 186:255-65.

Orskov, C., A. Wettergren, and J. J. Hoist. 1993. Biological effects and metabolic rates of glucagonlike peptide-1 7-36 amide and glucagonlike peptide-1 7-37 in healthy subjects are indistinguishable. Diabetes. 42:658-61.

Rouille, Y., S. Martin, and D. F. Steiner. 1995. Differential processing of proglucagon by the subtilisin-like prohormone convertases PC2 and PC3 to generate either glucagon or glucagon-like peptide. J Biol Chem. 270:26488-96.

Rufo, P. A., D. Merlin, M. Riegler, M. Ferguson-Maltzman, B. Dickinson, C. Brugnara, S. L. Alper, and W. I. Lencer. 1997. The antifungal antibiotic clotrimazole inhibits chloride secretion by human T84 cells via blockade of distinct basolateral K+ conductances. J. Clin. Invest. 100:3111-3120.

Simons, K., and R. Ehehalt. 2002. Cholesterol, lipid rafts, and disease. J Clin Invest. 110:597-603.

Simons, K., and W. L. Vaz. 2004. Model systems, lipid rafts, and cell membranes. Annu Rev Biophys Biomol Struct. 33:269-95.

Spiekermann, G. M., P. W. Finn, E. S. Ward, J. Dumont, B. L. Dickinson, R. S. Blumberg, and W. I. Lencer. 2002. Receptor-mediated immunoglobulin G transport across mucosal barriers in adult life: functional expression of FcRn in the mammalian lung. J Exp Med. 196:303-10.

Sturm, N. S., Y. Lin, S. K. Burley, J. L. Krstenansky, J. M. Ahn, B. Y. Azizeh, D. Trivedi, and V. J. Hruby. 1998. Structure-function studies on positions 17, 18, and 21 replacement analogues of glucagon: the importance of charged residues and salt bridges in glucagon biological activity. J Med Chem. 41:2693-700.

Tsai, B., C. Rodighiero, W. I. Lencer, and T. Rapoport. 2001. Protein disulfide isomerase acts as a redox-dependent chaperone to unfold cholera toxin. Cell. 104:937-948.

Xiao, Q., J. Giguere, M. Parisien, W. Jeng, S. A. St-Pierre, P. L. Brubaker, and M. B.

Wheeler. 2001. Biological activities of glucagon-like peptide-1 analogues in vitro and in vivo. Biochemistry. 40:2860-9.

Kelsall, B. Mucosal Immunology (2008) 1:460-469

Shang et. al. Gastroenterology 2008; 135:529-38

Backhed, F. et. al. Science 307, 1915-1920 (2005);

Rakoff-Nahoum S et. al. Mucosal Immunology (2008) 1:S10-S14;

Cerutti A. Nat Rev Immunol. 2008 8:421-34;

Maxfield, F. R., and T. E. McGraw. 2004. Nat Rev Mol Cell Biol. 5:121-32.

What is claimed is:

1. A complex of a delivery vehicle and an agent to be delivered, wherein the delivery vehicle comprises a glycosphingolipid comprising a ceramide that consists of a sphingosine coupled with a saturated long chain fatty acid (C14-C28), and wherein the agent to be delivered is covalently attached to the oligosaccharide of the glycosphingolipid.

2. The complex of claim 1, wherein the glycosphingolipid comprises a cerebroside, a ganglioside, a globoside, lactosyl ceramide (lac-Cer), glucosyl ceramide, galactosyl ceramide, a GD2, a GDIa, a GDIb, or a GM1.

3. The complex of claim 2, wherein the glycosphingolipid comprises a ganglioside.

4. The complex of claim 3, wherein the ganglioside comprises a sialic acid.

5. The complex of claim 4, wherein the ganglioside is monosialotetrahexosylganglioside (GM1).

6. The complex of claim 1, wherein the glycosphingolipid comprises a globoside.

7. The complex of claim 6, wherein the globo side is globotriaosyl ceramide (Gb3).

8. The complex of claim 1, wherein the fatty acid is a saturated C16:0 fatty acid.

9. The complex of claim 1, wherein the fatty acid is a saturated C18:0 fatty acid.

10. The complex of claim 1, wherein the agent to be delivered is selected from the group consisting of proteins, peptides, nucleic acids, polysaccharides, carbohydrates, lipids, glycoproteins, synthetic organic or inorganic drugs exerting a biological effect when administered to a subject, and combinations of different agents thereof.

11. The complex of claim 1, wherein the agent to be delivered is a therapeutic agent.

12. The complex of claim 1, wherein the therapeutic agent is selected from the group consisting of anti-inflammatory agent, a vaccine antigen, an anti-cancer drug, a chemotherapeutic drug, a clotting factor, a hormone, a steroid, a cytokine, an antibiotic, and a drug for treating a cardiovascular disease, an infectious disease, an autoimmune disease, allergy, a blood disorder, a metabolic disorder, or a skin disease.

13. A glycosphingolipid-therapeutic agent complex comprising a glycosphingolipid attached to a therapeutic agent, wherein the glycosphingolipid comprises a ceramide that consists of a sphingosine coupled with a saturated long chain fatty acid (C14-C28), and wherein the therapeutic agent to be delivered is covalently attached to the oligosaccharide of the glycosphingolipid.

14. A composition comprising the complex of claim 1.

15. A method of delivering an agent to a late endosome of a cell, the method comprising contacting the cell with the complex of claim 1, under conditions appropriate for uptake of the delivery vehicle or the agent into the cell.

16. A method of delivering an agent to a late endosome of a cells in an individual, the method comprising administering to the individual the complex of claim 1.

17. A method of treating a disease or condition in an individual in need thereof, the method comprising administering to the individual the complex of claim 1.

18. The method of claim 16, wherein the glycosphingolipid-agent complex is administered parenterally or nonparenterally.

19. The method of claim 18, wherein the agent is delivered to a sorting endosome or recycling endosome.

* * * * *

UNITED STATES PATENT AND TRADEMARK OFFICE
CERTIFICATE OF CORRECTION

PATENT NO. : 10,806,793 B2
APPLICATION NO. : 15/817661
DATED : October 20, 2020
INVENTOR(S) : Wayne I. Lencer et al.

Page 1 of 1

It is certified that error appears in the above-identified patent and that said Letters Patent is hereby corrected as shown below:

In Claim 7, at Column 32, Line 9:
"...the globo side is..."
Should read:
--...the globoside is...--

Signed and Sealed this
Twenty-third Day of February, 2021

Drew Hirshfeld
*Performing the Functions and Duties of the*
*Under Secretary of Commerce for Intellectual Property and*
*Director of the United States Patent and Trademark Office*